United States Patent
McCafferty et al.

(10) Patent No.: US 9,585,850 B2
(45) Date of Patent: *Mar. 7, 2017

(54) METHODS OF TREATMENT USING ARYLCYCLOPROPYLAMINE COMPOUNDS

(71) Applicant: Duke University, Durham, NC (US)

(72) Inventors: Dewey G. McCafferty, Chapel Hill, NC (US); Julie A. Pollock, Champaign, IL (US); David M. Gooden, Durham, NC (US); Marc G. Caron, Hillsborough, NC (US); Raul R. Gainetdinov, Chapel Hill, NC (US); Tatyana D. Sotnikova, Chapel Hill, NC (US)

(73) Assignee: Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/513,488

(22) Filed: Oct. 14, 2014

(65) Prior Publication Data

US 2015/0258044 A1  Sep. 17, 2015

Related U.S. Application Data

(63) Continuation of application No. 13/723,971, filed on Dec. 21, 2012, now abandoned.

(Continued)

(51) Int. Cl.
*A61K 31/135*  (2006.01)
*C07D 317/58*  (2006.01)
(Continued)

(52) U.S. Cl.
CPC .......... *A61K 31/135* (2013.01); *A61K 31/198* (2013.01); *A61K 31/343* (2013.01);
(Continued)

(58) Field of Classification Search
CPC .. A61K 31/343; A61K 31/135; A61K 31/198; C07D 317/58; C07C 217/74; C07C 211/40; C07C 323/31; C07C 211/42
See application file for complete search history.

(56) References Cited

U.S. PATENT DOCUMENTS 5,260,291 A   11/1993  Lunt et al.
5,747,498 A   5/1998   Schnur et al.
(Continued)

FOREIGN PATENT DOCUMENTS

EP  0520722  12/1992
EP  0564409  10/1993
(Continued)

OTHER PUBLICATIONS

Quinn British Medical Journal, vol. 310, No. 6979 (Mar. 4, 1995), pp. 575-579.*
(Continued)

*Primary Examiner* — Savitha Rao
*Assistant Examiner* — Angela Brown-Pettigrew
(74) *Attorney, Agent, or Firm* — Michael Best & Friedrich LLP

(57) ABSTRACT

The present invention is directed to a method of treating Parkinson's disease using arylcyclopropylamine compounds. The arylcyclopropylamine compounds have the following formula (Continued)

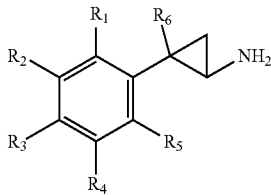

(I)

wherein $R_1$, $R_2$, $R_3$, $R_4$, $R_5$ and $R_6$ are described herein.

2 Claims, 9 Drawing Sheets

Related U.S. Application Data

(60) Provisional application No. 61/579,872, filed on Dec. 23, 2011.

(51) Int. Cl.
| | | |
|---|---|---|
| C07C 217/74 | (2006.01) | |
| C07C 211/40 | (2006.01) | |
| C07C 323/31 | (2006.01) | |
| C07C 211/42 | (2006.01) | |
| A61K 31/343 | (2006.01) | |
| A61K 31/198 | (2006.01) | |

(52) U.S. Cl.
CPC .......... *C07C 211/40* (2013.01); *C07C 211/42* (2013.01); *C07C 217/74* (2013.01); *C07C 323/31* (2013.01); *C07D 317/58* (2013.01)

(56) References Cited

U.S. PATENT DOCUMENTS

| 8,389,580 | B2 | 3/2013 | McCafferty et al. | |
|---|---|---|---|---|
| 2007/0027208 | A1 | 2/2007 | Caron et al. | |
| 2008/0139587 | A1 | 6/2008 | Huang et al. | |
| 2010/0324147 | A1* | 12/2010 | McCafferty ........... | C07C 217/74 514/647 |
| 2013/0178520 | A1 | 7/2013 | McCafferty et al. | |
| 2014/0343118 | A1 | 11/2014 | McCafferty et al. | |

FOREIGN PATENT DOCUMENTS

| EP | 0566226 | 10/1993 |
|---|---|---|
| EP | 0787722 | 8/1997 |
| EP | 0837063 | 4/1998 |
| WO | WO 96/33980 | 10/1996 |
| WO | WO 97/02266 | 1/1997 |
| WO | WO 97/22596 | 6/1997 |
| WO | WO 97/30034 | 8/1997 |
| WO | WO 97/30035 | 8/1997 |
| WO | WO 97/32856 | 9/1997 |
| WO | WO 97/38983 | 10/1997 |
| WO | WO 97/49688 | 12/1997 |
| WO | WO 98/13354 | 4/1998 |
| WO | WO 98/10767 | 8/1998 |
| WO | WO 98/35985 | 8/1998 |
| WO | WO 99/02166 | 1/1999 |
| WO | WO 99/03854 | 1/1999 |
| WO | WO 99/05143 | 2/1999 |
| WO | WO 00/40529 | 7/2000 |
| WO | WO 00/41669 | 7/2000 |
| WO | WO 00/47212 | 8/2000 |
| WO | WO 01/60814 | 8/2001 |
| WO | WO 01/92224 | 12/2001 |
| WO | WO 01/94341 | 12/2001 |
| WO | WO 02/04434 | 1/2002 |
| WO | WO 02/08213 | 1/2002 |
| WO | WO 02/22577 | 3/2002 |
| WO | WO 03/013541 | 2/2003 |

OTHER PUBLICATIONS

Youdim et al (British Journal of Pharmacology (2006) 147, S287-S296).*
Reynolds et al (Journal of the Royal Society of Medicine vol. 74 Sep. 1981 649).*
United States Patent Office Action for U.S. Appl. No. 14/210,848 dated Jul. 2, 2015 (14 pages).
"Parkinson's Disease: Molecular and Therapeutic Insights from Model Systems," Nass, R.; Przedborski, S., Eds.; Elsevier Inc.: Oxford, 2008.
Altman, R. A.; Buchwald, S. L., "Cu-catalyzed Goldberg and Ullmann reactions of aryl halides using chelating N- and O-based ligands." Nat. Protoc., 2007, 2, p. 2474-2479.
Arvidsson, L. et al., "N,N-Dialkylated Monophenolic trans-2-Phenylcyclopropylamines: Novel Central 5-Hydroxytryptamine Receptor Agonists" J. Med. Chem. (1988) 31:92-99.
BBC (2001) "Ecstacy & agony," http://www.bbc.co.uk/science/horizon/2000/ecstasyagony.shtml.
Berge et al., "Pharmaceutical Salts" J. Pharm. Sci. (1977) 66:1-19.
Binda, C. et al., "Insights into the mode of inhibition of human mitochondrial monoamine oxidase B from high-resolution crystal structures" Proc. Natl. Acad. Sci. USA (2003) 100:9750.
Binda, C., Valente, S., Romanenghi, M., Pilotto, S., Cirilli, R., Karytinos, A., Ciossani, G., Botrugno, O. A., Forneris, F., Tardugno, M., Edmonson, D. E., Minucci, S., Mattevi, A., Mai, A. "Biochemical, structural, and biological evolution of tranylcypromine derivatives as inhibitors of histone demethylases LSD1 and LSD2." J Am Chem Soc 132, 6827-6833 (2010).
Bishop, C., Taylor, J. L., Kuhn, D. M., Eskow, K. L., Park, J. Y., Walker, P. D. "MDMA and fenfluramine reduce L-DOPA-induced dyskinesia via indirect 5-HT1A receptor stimulation." Eur J Neurosci 23, 2669-2676 (2006).
Borowsky, B.; Adham, N.; Jones, K. A.; Raddatz, R.; Artymyshyn, R.; Ogozalek, K. L.; Durkin, M. M.; Lakhlani, P. P.; Bonini, J. A.; Pathirana, S.; Boyle, N.; Pu, X.; Kouranova, E.; Lichtblau, H.; Ochoa, F. Y.; Branchek, T. A.; Gerald, C., "Trace amines: identification of a family of mammalian G protein-coupled receptors." Proc. Natl. Acad. Sci. U.S.A., 2001, 98, p. 8966-8971.
Buchner, E.; Curtius, T., "Synthesis of b-keto esters from aldehydes and diazoacetic acid." Chem. Ber., 1885, 18, p. 2371-2377.
Bulinski et al., "Overexpression of MAP4 inhibits organelle motility and trafficking in vivo," (1997) J. Cell Sci. 110:3055-3064.
Burger et al., "Arylcycloalkylamines. III. 2-(3,4-Dimethoxyphenyl)-cyclopropylamine," Cobb Chemical Laboratory, University of Virginia, Charlottesville, Virginia, Received Feb. 4, 1952.
Burger, A. et al., "Arylcycloalkylamines. I. 2-Phenylcyclopropylamine" J. Am. Chem. Soc. (1948) 70:2198.
Ciaccio, J.A. et al., ""Instant Methylide" Modification of the Corey-Chaykovsky Cyclopropanation Reaction" Synth. Commun. (2006) 36:1333.
Cloos, P.A.C. et al., "The putative oncogene GASC1 demethylates tri- and dimethylated lysine 9 on histone H3" Nature (2006) 442:307.
Corey, E.J. et al., "Dimethyloxosulfonium Methylide ((CH3)2SOCH2) and Dimethylsulfonium Methylide ((CH3)2SCH2). Formation and Application to Organic Synthesis" J. Am. Chem. Soc. (1965) 87:1353.
Corey, E.J. et al., "Dimethylsulfoxonium Methylide" J. Am. Chem. Soc. (1962) 86:867.
Dallimore, J. E., Mickiewicz, A. L., Napier, T. C. (2006) "Intraventral pallidal glutamate antagonists block expression of morphine-induced place preference." Behav Neurosci 120:1103-1114.
Forneris, F. et al., "Histone demethylation catalysed by LSD1 is a flavin-dependent oxidative process" FEBS Lett. (2005) 579:2203.
Gainetdinov, R. R.; Wetsel, W. C.; Jones, S. R.; Levin, E. D.; Jaber, M.; Caron, M. G., "Role of serotonin in the paradoxical calming effect of psychostimulants on hyperactivity." Science, 1999, 283, p. 397-401.

(56) References Cited

OTHER PUBLICATIONS

Gerlach, M.; Riederer, P.,"Animal models of Parkinson's disease: an empirical comparison with the phenomenology of the disease in man." J. Neural. Transm., 1996, 103, p. 987-1041.

Giros, B.; Jaber, M.; Jones, S. R.; Wightman, R. M.; Caron, M. G., "Hyperlocomotion and indifference to cocaine and amphetamine in mice lacking the dopamine transporter." Nature, 1996, 379, p. 606-612.

Gooden, D.M. et al., "Facile synthesis of substituted trans-2-arylcyclopropylamine inhibitors of the human histone demethylase LSD1 and monoamine oxidases A and B," Biorg. Med. Chem. Lett. (2008) 18:3047-3051.

Guile et al. CAS: 130: 168386, 1999.

Hakimi, M-A. et al., "A Candidate X-linked Mental Retardation Gene Is a Component of a New Family of Histone Deacetylase-containing Complexes" J. Biol. Chem. (2003) 278:7234-7239.

He et al., "Regulation of Flowering Time by Histone Acetylation in *Arabidopsis*" Science (2003) 302:1751-1754.

He, S. et al., "Facile synthesis of site-specifically acetylated and methylated histone proteins: Reagents for evaluation of the histone code hypothesis" Proc. Natl. Acad. Sci. (2003) 100:12033-12038.

Heidenreich, B. A., Mailman, R.B., Nichols, D. E., Napier, T. C. (1995) "Partial and full dopamine D1 agonists produce comparable increases in ventral pallidal neuronal activity: Contribution of endogenous dopamine." J Pharmacol Exp Ther 273:516-525.

Heidenreich, B. A., Mitrovic, I., Battaglia, G., Napier, T. C. (2004) "Limbic pallidal adaptations following long-term cessation of dopaminergic transmission: lack of upregulation of dopamine receptor function." Exp Neurol 186:145-157.

Herrold, A. A., Shen, F., Graham, M. P., Harper, L. K., Specio, S. E., Tedford, C. E., Napier, T. C. (2009) "Mirtazapine treatment after conditioning with methamphetamine alters subsequent expression of place preference." Drug Alcohol Depend 99:231-239.

Herrold, A. A., Voigt, R. M., Napier, T. C. (2011) "Brain region selective cellular redistribution of mGlu5 but not GABAB receptors following methamphetamine-induced associative learning " Synapse, vol. 65, No. 12, 1333-1343.

Horner, L.; Hoffmann, H.; Wippel, H. G., "Phosphorus organic compounds. XII. Phosphine oxides as reagents for the olefin formation." Chem. Ber., 1958, 91, p. 61-63.

Hsu, A. et al. "Effect of the D3 dopamine receptor partial agonist BP897 [N-[4-(4-(2-methoxyphenyl)piperazinyl)butyl]-2-naphthamide] on L-3,4-Dihydroxyphenylalanine-induced dyskinesias and parkinsonism in squirrel monkeys." J Pharmacol Exp Ther 311, 770-7 (2004).

Huot, P., Johnston, T. H., Lewis, K. D. Koprich, J. B., Reyes, M. G., Fox, S. H., Piggott, M. J. and Brotchie, J. M. "Characterization of 3,4-Methylenedioxymethamphetamine (MDMA) enantiomers in vitro and in the MPTP-lesioned primate: R-MDMA reduces severity of dyskinesia, whereas SMDMA extends the duration of ON-time." J Neurosci 31, 7190-7198 (2001).

Hutton, H. M.; Schaefer, T., "Proton coupling constants in substituted cyclopropanes." Can. J. Chem., 1963, 41, p. 684-689.

Irviani, M. M., Jackson, M. J., Kuoppamaki, M., Smith, L. A., Jenner, P. "3,4-Methylenedioxymethamphetamine (ecstacy) inhibits dyskinesia expression and normalizes motor activity in 1-methyl-4-phenyl-1,2,3,6- tetrahydropryridine-treated primates." J Neurosci 23, 9107-9115 (2003).

Jemal, A.; Siegel, R.; Xu, J.; Ward, E., "Cancer Statistics, 2010." CA Cancer J. Clin., 2010, 60, p. 277-300.

Jones, S. R.; Gainetdinov, R. R.; Jaber, M.; Giros, B.; Wightman, R. M.; Caron, M. G., "Profound neuronal plasticity in response to inactivation of the dopamine transporter." Proc. Natl. Acad. Sci. U.S.A., 1998, 95, p. 4029-4034.

Klose, R.J. et al., "The transcriptional repressor JHDM3A demethylates trimethyl histone H3 lysine 9 and lysine 36" Nature (2006) 442:312-316.

Langston, J. W., Quik, M., Petzinger, G., Jakowec, M. & Di Monte, D. A. "Investigating levodopa-induced dyskinesias in the parkinsonian primate." Ann Neurol 47, S79-89 (2000).

Lee et al., "Histone H3 Lysine 4 Demethylation Is a Target of Nonselective Antidepressive Medications" Chem. Biol. (2006) 13:563-567.

Marcoux, J.; Doye, S.; Buchwald, S. L., "A general copper-catalyzed synthesis of diaryl ethers." J. Am. Chem. Soc., 1997, 119, p. 10539-10540.

McCafferty, D.G., "Synthesis and evaluation of trans-2-arylcyclopropylamine-based inhibiltors of lysine-specific demethylase 1" Division of Medicinal Chemistry Abstracts-235th ACS National Meeting, Apr. 6-10, 2008, http://www.acsmedchem.org/mediabstracts2008.pdf.

Mimasu, S., Umezawa, N., Sato, S., Higuchi, T., Umehara, T., Yokoyama, S. "Structurally-designed trans-2-phenylcyclopropylamine derivatives potently inhibit histone demethylase LSD/KDM1." Biochemistry 49, 6494-6503 (2010).

Molinoff, P. B.; Axelrod, J., "Biochemistry of catecholamines." Annu. Rev. Biochem., 1971, 40, p. 465-500.

Muhlradt et al., "Epothilone B Stabilizes Microtubuli of Macrophanges Like Taxol without Showing Taxol-like Endotoxin Activity," (1997) Cancer Res. 57:3344-3346.

Napier, T. C., Riddle, J. L., Rokosik, S. L. (2010). "Pramipexole induces a conditioned place preference in parkinsonian-like rats." 14th International Congress of Parkinson's Disease and Movement Disorders. Movement Disorders 25(7):S283, 2010.

Nicolaou et al., "Synthesis of epothilones A and B in solid and solution phase,"(1997) Nature 387:268-272.

Olsson, M., Nikkhah, G., Bentlage, C., Bjorklund, A. (1995) "Forelimb akinesia in the rat Parkinson model: differential effects of dopamine agonists and nigral transplants as assessed by a new stepping test." J Neurosci 15:3863-3875.

Pal, M.; Parasuraman, K.; Yeleswarapu, K. R., "Palladium-catalyzed cleavage of O/Npropargyl protecting groups in aqueous media under a copper-free condition." Org. Lett., 2003, 5, p. 349-352.

Panda et al., "Stabilization of microtubule dynamics by estramustine by binding to a novel site in tubulin: A possible mechanistic basis for its antitumor action," (1997) Proc. Natl. Acad. Sci. USA 94:10560-10564.

Panda et al., "Differential Effects of Vinblastine on Polymerization and Dynamics at Opposite Microtubule Ends," (1996) J. Biol. Chem. 271:29807-29812.

Pannala et al., "Synthesis and structure—activity relationship of 4-(2-aryl-cyclopropylamino)-quinoline-3-carbonitriles as EGFR tyrosine kinase inhibitors," Bioorganic & Medicinal Chemistry Letters, 2007, vol. 17, pp. 5978-5982.

Pollock et al., "Synthesis and characterization of small molecule inhibitors of human histone demethylase LSD1," 2009 poster presentation, 11 pages.

Quik, M. et al., "Nicotine reduces levodopa-induced dyskinesias in lesioned monkeys." Ann Neurol 62, 588-96 (2007).

Riederer, P.; Laux, G., "MAO-inhibitors in Parkinson's Disease." Exp. Neurobiol., 2011, 20, p. 1-17.

Rokosik, S. L. , Napier ,T. C. (2011) "Intracranial self-stimulation as a positive reinforcer to study impulsivity in a probability discounting paradigm." J Neurosci Methods 198:260-269.

Rokosik, S. L. , Napier, T. C. (2010). "Pramipexole-induced risky behavior in a rat model of Parkinson's disease. 14th International Congress of Parkinson's Disease and Movement Disorders." Movement Disorders 25(7):S285.

Rosen, T. et al., "Fluorinated Phenylcyclopropylamines. 2. Effects of Aromatic Ring Substitution and of Absolute Configuration on Inhibition of Microbial Tyramine Oxidase" J. Med. Chem. (2004) 47:5860.

Schmidt, D.M.Z. et al., "trans-2-Phenylcyclopropylamine Is a Mechanism-Based Inactivator of the Histone Demethylase LSD1" Biochem. (2007) 46:4408-4416.

Schultz, W., "Depletion of dopamine in the striatum as an experimental model of Parkinsonism: direct effects and adaptive mechanisms." Prog. Neurobiol., 1982, 18, p. 121-66.

Shen, F., Meredith, G. E., Napier, T. C. (2006) "Amphetamine-induced place preference and conditioned motor sensitization requires activation of tyrosine kinase receptors in the hippocampus." J Neurosci 26:11041-11051.

(56) References Cited

OTHER PUBLICATIONS

Sherry, R. L. Rauw, G., McKenna, K. F., Paetsch, P. R., Coutts, R. T., Baker, G. B. (2000) "Failure to detect amphetamine or 1-amino-3-phenlypropane in humans or rats receiving the MAO inhibitor tranylcypromine," J Affective Disorders 61: 23-29.
Shi, Y. et al., "Histone Demethylation Mediated by the Nuclear Amine Oxidase Homolog LSD1" Cell (2004) 119:941-953.
Sonitkova, T. D., Beaulieu, J. M., Sespinoza, S., Masri, B., Zhang, X., Salahpour, A., Barak, L. S., Caron, M. G., Gainetdinov, R. R. "The dopamine metabolite 3-methoxytyramine is a neuromodulator." PLoS Biol 5, e13452 (2010).
Sonitkova, T. D., Caron, M. G., Gainetdinov, R. R. "DDD mice, a novel acute mouse model of Parkinson's disease." Neurology 67, S12-S17 (2006).
Sotnikova, T. D.; Beaulieu, J. M.; Barak, L. S.; Wetsel, W. C.; Caron, M. G.; Gainetdinov, R. R., "Dopamine-independent locomotor actions of amphetamines in a novel acute mouse model of Parkinson disease." PLoS Biol., 2005, 3, p. e271.
Sotnikova, T. D.; Caron, M. G.; Gainetdinov, R. R., "Trace amine-associated receptors as emerging therapeutic targets." Mol. Pharmacol., 2009, 76, p. 229-235.
Stern et al., "Overview of monoclonal antibodies in cancer therapy: present and promise" Critical reviews in oncology/haematology, (2005) 54:11-29.
Szewczuk, L. et al., "Mechanistic Analysis of a Suicide Inactivator of Histone Demethylase LSD1" Biochem. (2006) 46:6892.
Tichilibon, S. et al., "Exploring distal regions of the A3 adenosine receptor binding site: sterically constrained N6-(2-phenylethyl)adenosine derivatives as potent ligands" Bioorg. Med. Chem. (2004) 12:2021.
Togasaki, D. M. et al. "Levodopa induces dyskinesias in normal squirrel monkeys." Ann Neurol 50, 254-7 (2001).
Togasaki, D. M. et al., "Dyskinesias in normal squirrel monkeys induced by nomifensine and levodopa." Neuropharmacology 48, 398-405 (2005).
Tsukada, Y. et al., "Histone demethylation by a family of JmjC domain-containing proteins" Nature (2006) 439:811.
Turner, M. S., Gray, T. S., Mickiewicz, A. L., Napier, T. C. (2008) "Fos expression following activation of the ventral pallidum in normal rats and in a model of Parkinson's Disease: implications for limbic system and basal ganglia interactions." Brain Struct Funct 213:197-213.
Turner, M. S., Mignon, L., Napier, T. C. (2002) "Alterations in responses of ventral pallidal neurons to excitatory amino acids after long-term dopamine depletion." J Pharmacol Exp Ther 301:371-381.
Ullmann, F.; Bielecki, J.,"Synthesis in the biphenyl series." Ber, 1901, 34, p. 2174-2185.
Vallgarda, J. et al., "trans-2-Aryl-N,N-dipropylcyclopropylamines: Synthesis and Interactions with 5-HT1A Receptors" J. Med. Chem. (1996) 39: pp. 1485-1493.
Vasquez et al., "Nanomolar Concentrations of Nocodazole Alter Microtubule Dynamic Instability In Vivo and In Vitro," (1997) Mol. Biol. Cell. 8:973-985.
Voigt, R. M., Herrold, A. A., Napier, T. C. (2011a) "Baclofen facilitates the extinction of methamphetamine-induced conditioned place preference in rats." Behav Neurosci 125:261-267, 2011.
Voigt, R. M., Herrold, A. A., Riddle, J. L., Napier, T. C. (2011b) "Administration of GABA(B) receptor positive allosteric modulators inhibit the expression of previously established methamphetamine-induced conditioned place preference." Behav Brain Res 216:419-423.
Wadsworth, W. S., Jr.; Emmons, W. D., "The utility of phosphonate carbanions in olefin synthesis." J. Am. Chem. Soc., 1961, 83, p. 1733-1738.
Whetstine, J.R. et al., "Reversal of Histone Lysine Trimethylation by the JMJD2 Family of Histone Demethylases" Cell (2006) 125:467.
Yamane, K. et al., "JHDM2A, a JmjC-Containing H3K9 Demethylase, Facilitates Transcription Activation by Androgen Receptor" Cell (2006) 125:483.
Yang, M. et al., "Structural Basis for the Inhibition of the LSD1 Histone Demethylase by the Antidepressant trans-2-Phenylcyclopropylamine" Biochemistry (2007) 46:8058.
Zhang, Y. et al., "Transcription regulation by histone methylation: interplay between different covalent modifications of the core histone tails" Genes Dev. (2001) 15:2343.
United States Patent Office Action for U.S. Appl. No. 13/723,971 dated Apr. 16, 2014 (15 pages).
Nial Quinn, British Medical Journal, vol. No. 310, No. 6979 (1995), pp. 575-579.
Costall et al., "Design of agents for stimulation of neostriatal dopaminergic mechanisms" J. Pharm. Pharmac., 1974, 26, 753-762.
Bannister, A. J., and Kouzarides, T. (2004) Histone methylation: recognizing the methyl mark, Methods Enzymol. 376, 269-288.
Bannister, A. J., and Kouzarides, T. (2005) Reversing histone methylation, Nature 436, 1103-1106.
Benelkebir, H., Hodgkinson, C., Duriez, P. J., Hayden, A. L., Bulleid, R. A., Crabb, S. J., Packham, G., and Ganesan, A. (2011) Enantioselective synthesis of tranylcypromine analogues as lysine demethylase (LSD1) inhibitors, Bioorg. Med. Chem. 19, 3709-3716.
Cosman, F., and Lindsay, R. (1999) Selective estrogen receptor modulators: clinical spectrum, Endocr. Rev. 20, 418-434.
Culhane, J. C., Wang, D., Yen, P. M., and Cole, P. A. (2010) Comparative analysis of small molecules and histone substrate analogues as LSD1 lysine demethylase inhibitors, J. Am. Chem. Soc. 132, 3164-3176.
Frasor, J., Danes, J. M., Komm, B., Chang, K. C., Lyttle, C. R., and Katzenellenbogen, B. S. (2003) Profiling of estrogen up- and down-regulated gene expression in human breast cancer cells: insights into gene networks and pathways underlying estrogenic control of proliferation and cell phenotype, Endocrinol. 144, 4562-4574.
Garcia-Bassets, I., Kwon, Y. S., Telese, F., Prefontaine, G. G., Hutt, K. R., Cheng, C. S., Ju, B. G., Ohgi, K. A., Wang, J., Escoubet-Lozach, L., Rose, D. W., Glass, C. K., Fu, X. D., and Rosenfeld, M. G. (2007) Histone methylation-dependent mechanisms impose ligand dependency for gene activation by nuclear receptors, Cell 128, 505-518.
Gaweska, H., Henderson Pozzi, M., Schmidt, D. M., McCafferty, D. G., and Fitzpatrick, P. F. (2009) Use of pH and kinetic isotope effects to establish chemistry as rate-limiting in oxidation of a peptide substrate by LSD1, Biochemistry 48, 5440-5445.
Gentleman, R. C., Carey, V. J., Bates, D. M., Bolstad, B., Dettling, M., Dudoit, S., Ellis, B., Gautier, L., Ge, Y., Gentry, J., Hornik, K., Hothorn, T., Huber, W., Iacus, S., Irizarry, R., Leisch, F., Li, C., Maechler, M., Rossini, A. J., Sawitzki, G., Smith, C., Smyth, G., Tierney, L., Yang, J. Y., and Zhang, J. (2004) Bioconductor: open software development for computational biology and bioinformatics, Genome Biol. 5, R80.
Hoeflich, K. P., O'Brien, C., Boyd, Z., Cavet, G., Guerrero, S., Jung, K., Januario, T., Savage, H., Punnoose, E., Truong, T., Zhou, W., Berry, L., Murray, L., Amler, L., Belvin, M., Friedman, L. S., and Lackner, M. R. (2009) In vivo antitumor activity of MEK and phosphatidylinositol 3-kinase inhibitors in basal-like breast cancer models, Clin. Cancer Res. 15, 4649-4664.
Hu, Q., Kwon, Y. S., Nunez, E., Cardamone, M. D., Hutt, K. R., Ohgi, K. A., Garcia-Bassets, I., Rose, D. W., Glass, C. K., Rosenfeld, M. G., and Fu, X. D. (2008) Enhancing nuclear receptor-induced transcription requires nuclear motor and LSD1-dependent gene networking in interchromatin granules, Proc. Natl. Acad. Sci. U.S.A. 105, 19199-19204.
Huang, J., Sengupta, R., Espejo, A. B., Lee, M. G., Dorsey, J. A., Richter, M., Opravil, S., Shiekhattar, R., Bedford, M. T., Jenuwein, T., and Berger, S. L. (2007) p53 is regulated by the lysine demethylase LSD1, Nature 449, 105-108.
Huang, Y., Greene, E., Murray Stewart, T., Goodwin, A. C., Baylin, S. B., Woster, P. M., and Casero, R. A., Jr. (2007) Inhibition of

(56) References Cited

OTHER PUBLICATIONS lysine-specific demethylase 1 by polyamine analogues results in reexpression of aberrantly silenced genes, Proc. Natl. Acad. Sci. U.S.A. 104, 8023-8028.

Huang, Y., Stewart, T. M., Wu, Y., Baylin, S. B., Marton, L. J., Perkins, B., Jones, R. J., Woster, P. M., and Casero, R. A., Jr. (2009) Novel oligoamine analogues inhibit lysine-specific demethylase 1 and induce reexpression of epigenetically silenced genes, Clin. Cancer Res. 15, 7217-7228.

Huang, Y., Vasilatos, S. N., Boric, L., Shaw, P. G., and Davidson, N. E. (2011) Inhibitors of histone demethylation and histone deacetylation cooperate in regulating gene expression and inhibiting growth in human breast cancer cells, Breast Cancer Res. Treat.

Ivshina, A. V., George, J., Senko, O., Mow, B., Putti, T. C., Smeds, J., Lindahl, T., Pawitan, Y., Hall, P., Nordgren, H., Wong, J. E., Liu, E. T., Bergh, J., Kuznetsov, V. A., and Miller, L. D. (2006) Genetic reclassification of histologic grade delineates new clinical subtypes of breast cancer, Cancer Res. 66, 10292-10301.

Karytinos, A., Forneris, F., Profumo, A., Ciossani, G., Battaglioli, E., Binda, C., and Mattevi, A. (2009) A novel mammalian flavin-dependent histone demethylase, J. Biol. Chem. 284, 17775-17782.

Kelly, W. K., O'Connor, O. A., and Marks, P. A. (2002) Histone deacetylase inhibitors: from target to clinical trials, Expert Opin. Investig. Drugs 11, 1695-1713.

Liang, Y., Vogel, J. L., Narayanan, A., Peng, H., and Kristie, T. M. (2009) Inhibition of the histone demethylase LSD1 blocks alpha-herpesvirus lytic replication and reactivation from latency, Nat. Med. 15, 1312-1317.

Lim, S., Janzer, A., Becker, A., Zimmer, A., Schule, R., Buettner, R., and Kirfel, J. (2010) Lysine-specific demethylase 1 (LSD1) is highly expressed in ER-negative breast cancers and a biomarker predicting aggressive biology, Carcinogenesis 31, 512-520.

Metzger, E., Wissmann, M., Yin, N., Muller, J. M., Schneider, R., Peters, A. H., Gunther, T., Buettner, R., and Schule, R. (2005) LSD1 demethylates repressive histone marks to promote androgen-receptor-dependent transcription, Nature 437, 436-439.

Mimasu, S., Sengoku, T., Fukuzawa, S., Umehara, T., and Yokoyama, S. (2008) Crystal structure of histone demethylase LSD1 and tranylcypromine at 2.25 A, Biochemical and biophysical research communications 366, 15-22.

Sambucetti, L. C., Fischer, D. D., Zabludoff, S., Kwon, P. O., Chamberlin, H., Trogani, N., Xu, H., and Cohen, D. (1999) Histone deacetylase inhibition selectively alters the activity and expression of cell cycle proteins leading to specific chromatin acetylation and antiproliferative effects, J. Biol. Chem. 274, 34940-34947.

Schreiber, S. L., and Bernstein, B. E. (2002) Signaling network model of chromatin, Cell 111, 771-778.

Scoumanne, A., and Chen, X. (2007) The lysine-specific demethylase 1 is required for cell proliferation in both p53-dependent and -independent manners, J. Biol. Chem. 282, 15471-15475.

Shi, Y. J., Matson, C., Lan, F., Iwase, S., Baba, T., and Shi, Y. (2005) Regulation of LSD1 histone demethylase activity by its associated factors, Mol. Cell 19, 857-864.

Siegel, R., Ward, E., Brawley, O., and Jemal, A. (2011) Cancer statistics, 2011: the impact of eliminating socioeconomic and racial disparities on premature cancer deaths, CA Cancer J. Clin. 61, 212-236.

Strahl, B. D., and Allis, C. D. (2000) The language of covalent histone modifications, Nature 403, 41-45.

Tan, J., Cang, S., Ma, Y., Petrillo, R. L., and Liu, D. (2010) Novel histone deacetylase inhibitors in clinical trials as anti-cancer agents, J. Hematol. Oncol. 3, 5-17.

Team, R. D. C. (2011) A language and environment for statistical computing, In R Foundation for Statistical Computing, Vienna, Austria.

Wang, J., Hevi, S., Kurash, J. K., Lei, H., Gay, F., Bajko, J., Su, H., Sun, W., Chang, H., Xu, G., Gaudet, F., Li, E., and Chen, T. (2009) The lysine demethylase LSD1 (KDM1) is required for maintenance of global DNA methylation, Nat. Genet. 41, 125-129.

Wang, J., Scully, K., Zhu, X., Cai, L., Zhang, J., Prefontaine, G. G., Krones, A., Ohgi, K. A., Zhu, P., Garcia-Bassets, I., Liu, F., Taylor, H., Lozach, J., Jayes, F. L., Korach, K. S., Glass, C. K., Fu, X. D., and Rosenfeld, M. G. (2007) Opposing LSD1 complexes function in developmental gene activation and repression programmes, Nature 446, 882-887.

Warnes, G. R., Bolker, B., Bonebakker, L., Gentleman, R., Huber, W., Liaw, A., Lumley, T., Maechler, M., Magnusson, A., Moeller, S., Schwartz, M., and Venables, B. (2010) gplots: Various R programming tools for plotting data., 2.8.0 ed., p R. package.

Zhu, Q., Huang, Y., Marton, L. J., Woster, P. M., Davidson, N. E., and Casero, R. A., Jr. (2011) Polyamine analogs modulate gene expression by inhibiting lysine-specific demethylase 1 (LSD1) and altering chromatin structure in human breast cancer cells, Amino Acids, 887-898.

United States Patent Office Final Action for U.S. Appl. No. 14/210,848 dated Nov. 16, 2015 (13 pages).

* cited by examiner

METHODS OF TREATMENT USING ARYLCYCLOPROPYLAMINE COMPOUNDS

CROSS-REFERENCE TO RELATED APPLICATIONS

This application is a continuation of U.S. patent application Ser. No. 13/723,971, filed Dec. 21, 2012, which application claims the benefit of U.S. Provisional Patent Application No. 61/579,872, filed on Dec. 23, 2011. The entire contents of each of these applications are hereby incorporated by reference.

STATEMENT REGARDING FEDERALLY SPONSORED RESEARCH

This invention was made with United States Government support awarded by National Institutes of Health, Grant No. GM65539. The U.S. Government has certain rights in this invention.

BACKGROUND

Although there is no known cure for Parkinson's disease (PD), one of the two most common neurodegenerative diseases of aging, dopamine (DA) replacement therapy by administration of the DA biosynthetic precursor levodopa (L-DOPA or LD) has been employed for over 40 years as the gold standard for treatment of PD-associated symptoms. However, the efficacy of this treatment may wane with time, and the drug may have a number of long-term side-effects including L-DOPA-induced dyskinesias (LIDs), fluctuations in motor performance, and hallucinations. Often these effects can become dose limiting at a time when patients are in need of more medication and not less. DA agonists, as well as several other classes of drugs directly or indirectly affecting DA function (monoamine oxidase (MAO) inhibitors, catechol-O-methyl transferase (COMT) inhibitors, and amantadine), may have some beneficial effects in PD patients, but none of these drugs are as effective as L-DOPA, and some, such as the dopamine agonists, may also have burdensome side-effects. Due to such limitations, effective anti-Parkinsonian agents that are free of side-effects such as dyskinesia, and/or agents that ameliorate dyskinesias are needed.

SUMMARY

In one aspect, the disclosure provides a method of treating Parkinson's disease in a subject in need of treatment, comprising administering to the subject an effective amount of a compound of formula (I):

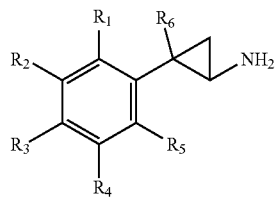

(I)

wherein $R_1$, $R_2$, $R_3$, $R_4$ and $R_5$ are independently selected from hydrogen, $C_{1-7}$ alkyl, $C_{3-20}$ heterocyclyl, $C_{5-20}$ aryl, $C_{1-7}$ alkoxy, $C_{1-7}$ haloalkyl, halo, amino, cyano, nitro, ether and thioether, or any two of $R_1$, $R_2$, $R_3$, $R_4$ and $R_5$ may be taken together with the carbon atoms to which they are attached to form an optionally substituted ring; and $R_6$ is selected from hydrogen and optionally substituted $C_{5-20}$ aryl;

or an isomer, prodrug or pharmaceutically acceptable salt thereof.

In one aspect, the disclosure provides a method of treating Parkinson's disease in a subject in need of treatment, comprising administering to the subject an effective amount of a compound of formula (II):

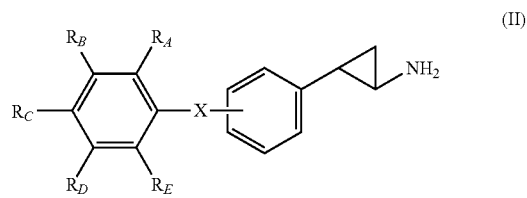

(II)

wherein:

X is selected from a bond, O, S, and NH; and $R_A$, $R_B$, $R_C$, $R_D$ and $R_E$ are independently selected from hydrogen, $C_{1-7}$ alkyl, $C_{5-20}$ aryl, $C_{3-20}$ heterocyclyl, $C_{1-7}$ alkoxy, amino, cyano, nitro, halo, haloalkyl, ether and thioether; or an isomer, prodrug or pharmaceutically acceptable salt thereof.

In another aspect, the disclosure provides a method of treating Parkinson's disease in a subject in need of treatment, comprising administering to the subject an effective amount of a compound of formula (IX):

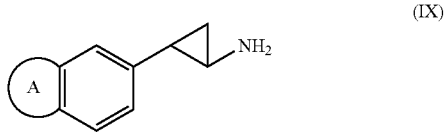

(IX)

wherein:

A is a $C_5$-$C_6$ aryl, cycloalkenyl or heterocyclyl ring.

In another aspect, the disclosure provides a method of treating Parkinson's disease in a subject in need of treatment, comprising administering to the subject an effective amount of a compound of formula (XV):

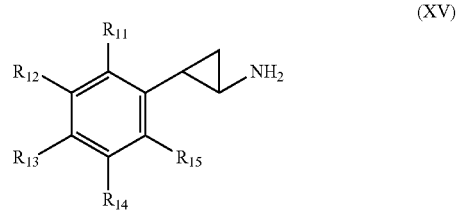

(XV)

wherein $R_{11}$, $R_{12}$, $R_{13}$, $R_{14}$ and $R_{15}$ are independently selected from hydrogen, $C_{1-7}$ alkyl, $C_{3-20}$ heterocyclyl, $C_{2-7}$ alkoxy, amino, cyano, nitro, ether and thioether; or an isomer, prodrug or pharmaceutically acceptable salt thereof.

In another aspect, the disclosure provides a method of treating Parkinson's disease in a subject in need of treatment, comprising administering to the subject an effective amount of a compound described herein and L-3,4-dihydroxyphenylalanine (L-DOPA).

In another aspect, the disclosure provides a method of reducing dyskinesia in a subject in need thereof, comprising administering to the subject an effective amount of a compound described herein. In embodiments, the dyskinesia may be an L-DOPA-induced dyskinesia.

In another aspect, the disclosure provides a pharmaceutical composition comprising a compound having the following formula:

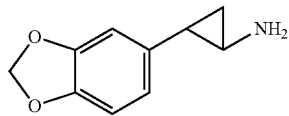 [SMILES: NC1CC1c1ccc2c(c1)OCO2]

or a pharmaceutically acceptable salt thereof, and a pharmaceutically acceptable carrier.

Other aspects and embodiments will become apparent in light of the following disclosure and drawings.

DETAILED DESCRIPTION

Figure 1:
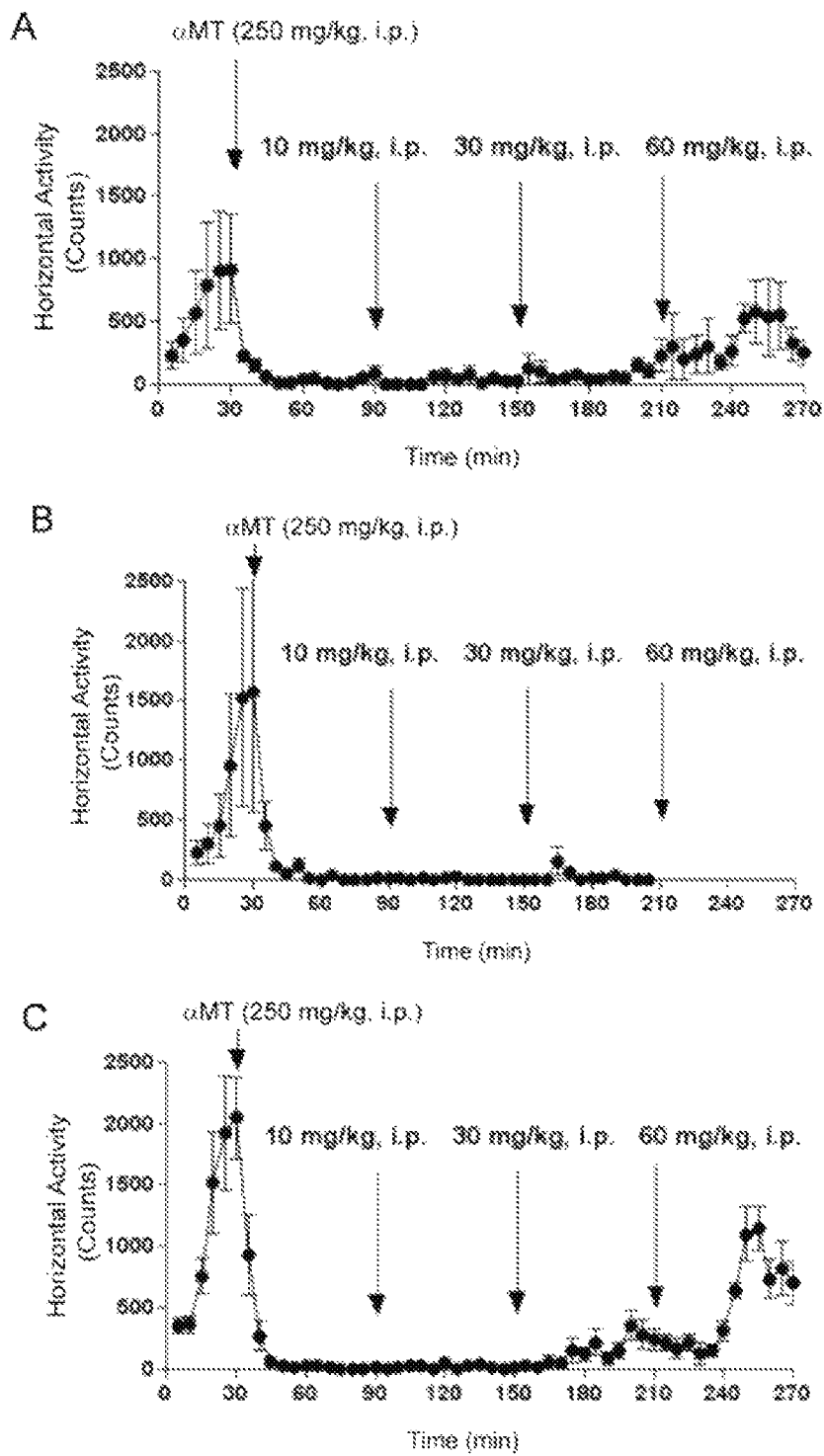
FIG. 1 illustrates results from unbiased screening of compounds in DDD mice (n=4 for each). Horizontal activity after treatment with: A) compound 1; B) compound 2; C) compound 3; D) compound 4; E) compound 5; F) compound 6; G) compound 7; H) compound 8; I) compound 9; J) compound 10; K) compound 11; each at indicated concentrations. Compound numbers are provided in Example 10.
Figure 1:
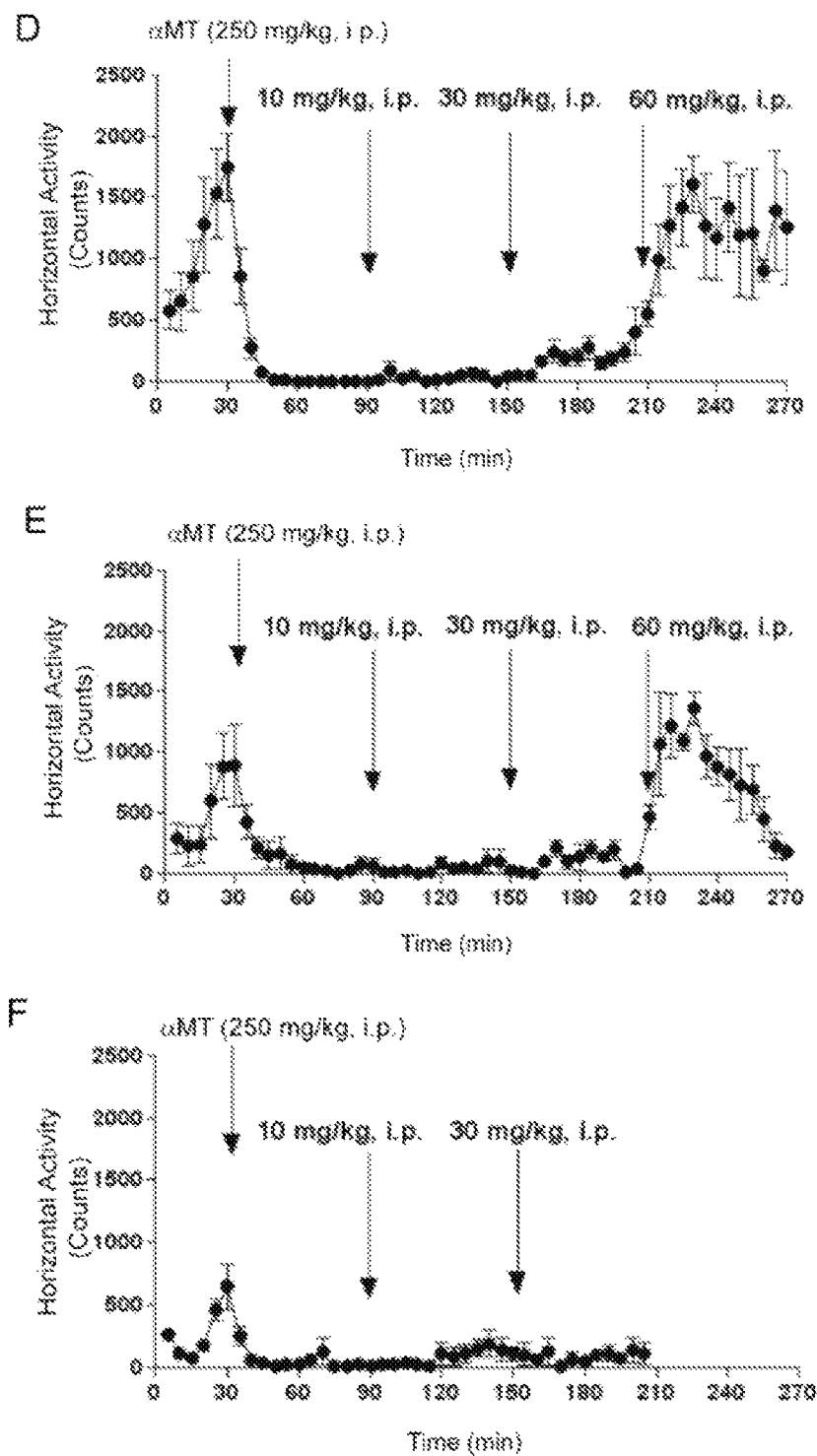
Figure 1:
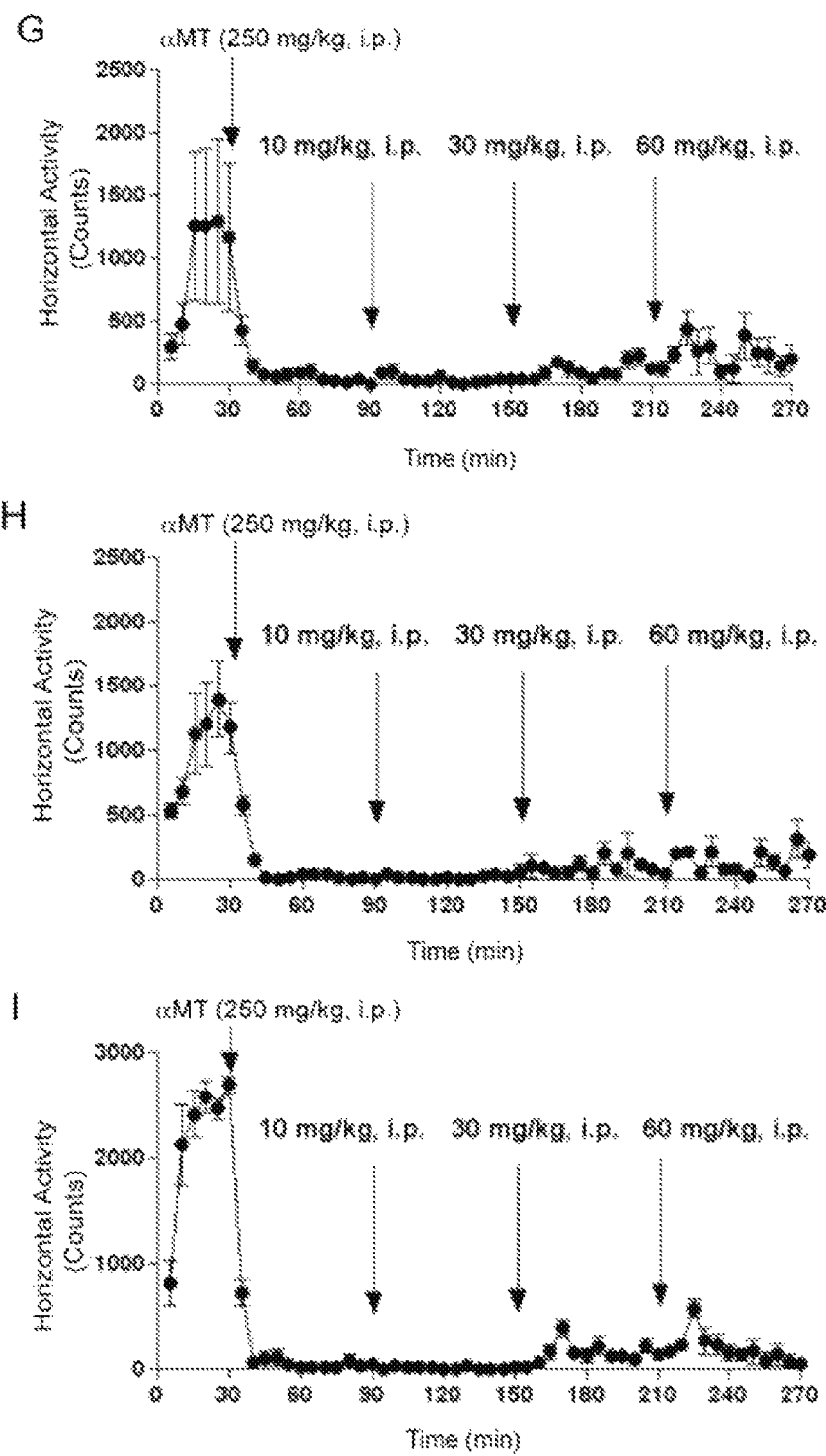
Figure 1:
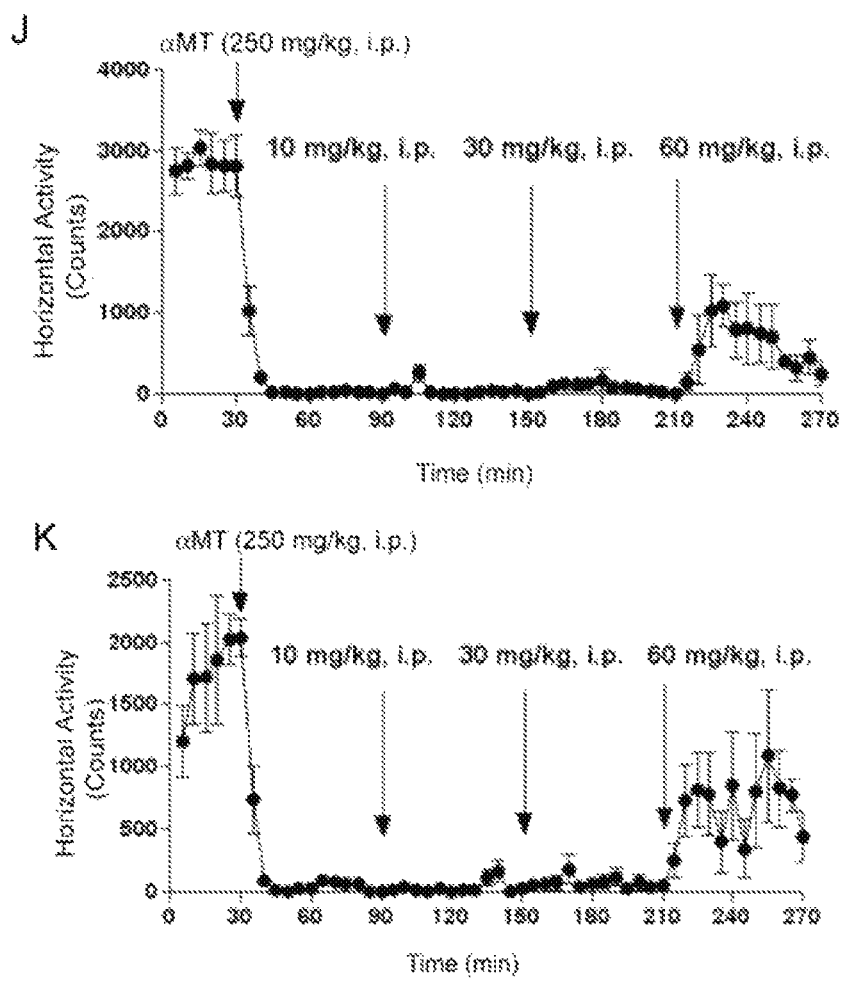

Before any embodiments of the disclosure are explained in detail, it is to be understood that the methods of the disclosure are not limited in application to the details of construction and the arrangement of components set forth in the following description or illustrated in the following drawings. The methods of the disclosure are capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

The invention generally relates to methods of treating Parkinson's disease and related disorders using arylcyclopropylamine compounds.

DEFINITIONS

The term "$C_{5-20}$ aryl", as used herein, pertains to a monovalent moiety obtained by removing a hydrogen atom from an aromatic ring atom of a $C_{5-20}$ aromatic compound, said compound having one ring, or two or more rings (e.g., fused), and having from 5 to 20 ring atoms, and wherein at least one of said ring(s) is an aromatic ring. Suitably, each ring has from 5 to 7 ring atoms.

The ring atoms may be all carbon atoms, as in "carboaryl groups", in which case the group may conveniently be referred to as a "$C_{5-20}$ carboaryl" group. Examples of $C_{5-20}$ aryl groups which do not have ring heteroatoms (i.e. $C_{5-20}$ carboaryl groups) include, but are not limited to, those derived from benzene (i.e. phenyl) (C6), naphthalene (C10), anthracene (C14), phenanthrene (C14), naphthacene (C18), and pyrene (C16).

Examples of aryl groups which comprise fused rings, one of which is not an aromatic ring, include, but are not limited to, groups derived from indene and fluorene.

Alternatively, the ring atoms may include one or more heteroatoms, including but not limited to oxygen, nitrogen, and sulfur, as in "heteroaryl groups". In this case, the group may conveniently be referred to as a "$C_{5-20}$ heteroaryl" group, wherein "$C_{5-20}$" denotes ring atoms, whether carbon atoms or heteroatoms. Suitably, each ring has from 5 to 7 ring atoms, of which from 0 to 4 are ring heteroatoms. Examples of $C_{5-20}$ heteroaryl groups include, but are not limited to, C5 heteroaryl groups derived from furan (oxole), thiophene (thiole), pyrrole (azole), imidazole (1,3-diazole), pyrazole (1,2-diazole), triazole, oxazole, isoxazole, thiazole, isothiazole, oxadiazole, tetrazole, oxadiazole (furazan) and oxatriazole; and C6 heteroaryl groups derived from isoxazine, pyridine (azine), pyridazine (1,2-diazine), pyrimidine (1,3-diazine; e.g., cytosine, thymine, uracil), pyrazine (1,4-diazine) and triazine.

The above $C_{5-20}$ aryl groups whether alone or part of another substituent, may themselves optionally be substituted with one or more groups selected from themselves and the additional substituents listed below.

The term "$C_{1-7}$ alkyl", as used herein, pertains to a monovalent moiety obtained by removing a hydrogen atom from a hydrocarbon compound having from 1 to 7 carbon atoms, which may be aliphatic or alicyclic, or a combination thereof, and which may be saturated, partially unsaturated, or fully unsaturated. Suitably, the alkyl group contains from 3 to 7 carbon atoms, i.e. is a "$C_{3-7}$ alkyl".

Examples of saturated linear $C_{1-7}$ alkyl groups include, but are not limited to, methyl, ethyl, n-propyl, n-butyl, and n-pentyl (amyl).

Examples of saturated branched $C_{1-7}$ alkyl groups include, but are not limited to, iso-propyl, iso-butyl, sec-butyl, tert-butyl, and neo-pentyl.

Examples of saturated alicyclic $C_{1-7}$ alkyl groups (also referred to as "$C_{3-7}$ cycloalkyl" groups) include, but are not limited to, groups such as cyclopropyl, cyclobutyl, cyclopentyl, and cyclohexyl, as well as substituted groups (e.g., groups which comprise such groups), such as methylcyclopropyl, dimethylcyclopropyl, methylcyclobutyl, dimethylcyclobutyl, methylcyclopentyl, dimethylcyclopentyl, methylcyclohexyl, dimethylcyclohexyl, cyclopropylmethyl and cyclohexylmethyl.

Examples of unsaturated $C_{1-7}$ alkyl groups which have one or more carbon-carbon double bonds (also referred to as "$C_{2-7}$ alkenyl" groups) include, but are not limited to, ethenyl (vinyl, —CH=CH$_2$), 2-propenyl (allyl, —CH—CH=CH$_2$), isopropenyl (—C(CH$_3$)=CH$_2$), butenyl, pentenyl, and hexenyl.

Examples of unsaturated $C_{1-7}$ alkyl groups which have one or more carbon-carbon triple bonds (also referred to as "$C_{2-7}$ alkynyl" groups) include, but are not limited to, ethynyl and 2-propynyl (propargyl).

Examples of unsaturated alicyclic (carbocyclic) $C_{1-7}$ alkyl groups which have one or more carbon-carbon double bonds (also referred to as "$C_{3-7}$ cycloalkenyl" groups) include, but are not limited to, unsubstituted groups such as cyclopropenyl, cyclobutenyl, cyclopentenyl, and cyclohexenyl, as well as substituted groups (e.g., groups which comprise such groups) such as cyclopropenylmethyl and cyclohexenylmethyl.

The term "$C_{3-20}$ heterocyclyl", as used herein, pertains to a monovalent moiety obtained by removing a hydrogen atom from a ring atom of a $C_{3-20}$ heterocyclic compound, said compound having one ring, or two or more rings (e.g., spiro, fused, bridged), and having from 3 to 20 ring atoms, of which from 1 to 10 are ring heteroatoms, and wherein at least one of said ring(s) is a heterocyclic ring. Suitably, each ring has from 3 to 7 ring atoms, of which from 1 to 4 are ring heteroatoms. Ring heteroatoms may be selected from the group consisting of O, N, S and P. "$C_{3-20}$" denotes ring atoms, whether carbon atoms or heteroatoms.

Examples of $C_{3-20}$ heterocyclyl groups having one nitrogen ring atom include, but are not limited to, those derived from aziridine, azetidine, pyrrolidines (tetrahydropyrrole), pyrroline (e.g., 3-pyrroline, 2,5-dihydropyrrole), 2H-pyrrole or 3H-pyrrole (isopyrrole, isoazole), piperidine, dihydropyridine, tetrahydropyridine, and azepine.

Examples of $C_{3-20}$ heterocyclyl groups having one oxygen ring atom include, but are not limited to, those derived from oxirane, oxetane, oxolane (tetrahydrofuran), oxole (dihydrofuran), oxane (tetrahydropyran), dihydropyran, pyran (C6), and oxepin. Examples of substituted $C_{3-20}$ heterocyclyl groups include sugars, in cyclic form, for example, furanoses and pyranoses, including, for example, ribose, lyxose, xylose, galactose, sucrose, fructose, and arabinose.

Examples of $C_{3-20}$ heterocyclyl groups having one sulfur ring atom include, but are not limited to, those derived from thiirane, thietane, thiolane (tetrahydrothiophene), thiane (tetrahydrothiopyran), and thiepane.

Examples of $C_{3-20}$ heterocyclyl groups having two oxygen ring atoms include, but are not limited to, those derived from dioxolane, dioxane, and dioxepane.

Examples of $C_{3-20}$ heterocyclyl groups having two nitrogen ring atoms include, but are not limited to, those derived from imidazolidine, pyrazolidine (diazolidine), imidazoline, pyrazoline (dihydropyrazole), and piperazine.

Examples of $C_{3-20}$ heterocyclyl groups having one nitrogen ring atom and one oxygen ring atom include, but are not limited to, those derived from tetrahydrooxazole, dihydrooxazole, tetrahydroisoxazole, dihydroisoxazole, morpholine, tetrahydrooxazine, dihydrooxazine, and oxazine.

Examples of $C_{3-20}$ heterocyclyl groups having one oxygen ring atom and one sulfur ring atom include, but are not limited to, those derived from oxathiolane and oxathiane (thioxane).

Examples of $C_{3-20}$ heterocyclyl groups having one nitrogen ring atom and one sulfur ring atom include, but are not limited to, those derived from thiazoline, thiazolidine, and thiomorpholine.

Other examples of $C_{5-20}$ heterocyclic groups (some of which are $C_{5-20}$ heteroaryl groups) which comprise fused rings, include, but are not limited to, C9 heterocyclic groups derived from benzofuran, isobenzofuran, indole, isoindole, purine (e.g., adenine, guanine), benzothiophene, benzimidazole; C10 heterocyclic groups derived from quinoline, isoquinoline, benzodiazine, pyridopyridine, quinoxaline; C13 heterocyclic groups derived from carbazole, dibenzothiophene, dibenzofuran; C14 heterocyclic groups derived from acridine, xanthene, phenoxathiin, phenazine, phenoxazine, phenothiazine.

Other examples of $C_{3-20}$ heterocyclyl groups include, but are not limited to, oxadiazine and oxathiazine.

Examples of heterocyclyl groups which additionally bear one or more oxo (=O) groups, include, but are not limited to, those derived from: C5 heterocyclics, such as furanone, pyrone, pyrrolidone (pyrrolidinone), pyrazolone (pyrazolinone), imidazolidone, thiazolone, and isothiazolone; C6 heterocyclics, such as piperidinone (piperidone), piperidinedione, piperazinone, piperazinedione, pyridazinone, and pyrimidinone (e.g., cytosine, thymine, uracil), and barbituric acid; fused heterocyclics, such as oxindole, purinone (e.g., guanine), benzoxazolinone, benzopyrone (e.g., coumarin); cyclic anhydrides (—C(=O)—O—C(=O)— in a ring), including but not limited to maleic anhydride, succinic anhydride, and glutaric anhydride; cyclic carbonates (—O—C(=O)—O— in a ring), such as ethylene carbonate and 1,2-propylene carbonate; imides (—C(=O)—NR—C(=O)— in a ring), including but not limited to, succinimide, maleimide, phthalimide, and glutarimide; lactones (cyclic esters, —O—C(=O)— in a ring), including, but not limited to, β-propiolactone, γ-butyrolactone, δ-valerolactone (2-piperidone), and ε-caprolactone; lactams (cyclic amides, —NR—C(=O)— in a ring), including, but not limited to, β-propiolactam, γ-butyrolactam (2-pyrrolidone), δ-valerolactam, and ε-caprolactam; cyclic carbamates (—O—C(=O)—NR— in a ring), such as 2-oxazolidone; cyclic ureas (—NR—C(=O)—NR— in a ring), such as 2-imidazolidone and pyrimidine-2,4-dione (e.g., thymine, uracil).

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), a $C_{5-20}$ aryl group (also referred to as a $C_{5-20}$ aryloxy group), or a $C_{5-20}$ arylalkyl group (also referred to as a $C_{5-20}$ arylalkyloxy group), for example, a benzyl group.

$C_{1-7}$ alkoxy: —OR, wherein R is a $C_{1-7}$ alkyl group. Examples of $C_{1-7}$ alkoxy groups include, but are not limited to, —OCH$_3$ (methoxy), —OCH$_2$CH$_3$ (ethoxy) and —OC(CH$_3$)$_3$ (tert-butoxy).

Oxo (keto, -one): =O. Examples of cyclic compounds and/or groups having, as a substituent, an oxo group (=O) include, but are not limited to, carbocyclics such as cyclopentanone and cyclohexanone; heterocyclics, such as pyrone, pyrrolidone, pyrazolone, pyrazolinone, piperidone, piperidinedione, piperazinedione, and imidazolidone; cyclic anhydrides, including but not limited to maleic anhydride and succinic anhydride; cyclic carbonates, such as propylene carbonate; imides, including but not limited to, succinimide and maleimide; lactones (cyclic esters, —O—C(=O)— in a ring), including, but not limited to, β-propiolactone, γ-butyrolactone, δ-valerolactone, and ε-caprolactone; and lactams (cyclic amides, —NH—C(=O)— in a ring), including, but not limited to, β-propiolactam, γ-butyrolactam (2-pyrrolidone), δ-valerolactam, and ε-caprolactam.

Imino (imine): =NR, wherein R is an imino substituent, for example, hydrogen, $C_{1-7}$ alkyl group, a $C_{3-20}$ heterocyclyl group, or a $C_{5-20}$ aryl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl). Examples of acyl groups include, but are not limited to, —C(=O)CH$_3$ (acetyl), —C(=O)CH$_2$CH$_3$ (propionyl), —C(=O)C(CH$_3$)$_3$ (butyryl), and —C(=O)Ph (benzoyl, phenone).

Carboxy (carboxylic acid): —COOH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Amido (carbamoyl, carbamyl, aminocarbonyl, carboxamide): —C(=O)NR1R2, wherein R1 and R2 are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R1 and R2, together with the nitrogen atom to which they are attached, form a heterocyclic structure as in, for example, piperidinocarbonyl, morpholinocarbonyl, thiomorpholinocarbonyl, and piperazinocarbonyl.

Acylamido (acylamino): —NR1C(=O)R2, wherein R1 is an amide substituent, for example, hydrogen, a $C_{1-7}$ alkyl group, a $C_{3-20}$ heterocyclyl group, or a $C_{5-20}$ aryl group, and R2 is an acyl substituent, for example, a $C_{1-7}$ alkyl group, a $C_{3-20}$ heterocyclyl group, or a $C_{5-20}$ aryl group. Examples of acylamide groups include, but are not limited to, —NHC(=O)CH$_3$, —NHC(=O)CH$_2$CH$_3$, and —NHC(=O)Ph. R1 and R2 may together form a cyclic structure, as in, for example, succinimidyl, maleimidyl and phthalimidyl.

Acylureido: —N(R1)C(O)NR2C(O)R3 wherein R1 and R2 are independently ureido substituents, for example, hydrogen, a $C_{1-7}$ alkyl group, a $C_{3-20}$ heterocyclyl group, or a $C_{5-20}$ aryl group. R3 is an acyl group as defined for acyl groups. Examples of acylureido groups include, but are not limited to, —NHCONHC(O)H, —NHCONMeC(O)H, —NHCONEtC(O)H, —NHCONMeC(O)Me, —NHCONEtC(O)Et, —NMeCONHC(O)Et, —NMeCONHC(O)Me, —NMeCONMeC(O)Et, —NMeCONMeC(O)Me, —NMeCONEtC(O)Et, and —NMeCONHC(O)Ph.

Carbamate: —NR1-C(O)—OR2 wherein R1 is an amino substituent as defined for amino groups and R2 is an ester group as defined for ester groups. Examples of carbamate groups include, but are not limited to, —NH—C(O)—O-Me, —NMe-C(O)—O-Me, —NH—C(O)—O-Et, —NMe-C(O)—O-t-butyl, and —NH—C(O)—O-Ph.

Thioamido (thiocarbamyl): —C(=S)NR1R2, wherein R1 and R2 are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Tetrazolyl: a five membered aromatic ring having four nitrogen atoms and one carbon atom.

Amino: —NR1R2, wherein R1 and R2 are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, or, in the case of a "cyclic" amino group, R1 and R2, taken together with the nitrogen atom to which they are attached, form a heterocyclic ring having from 4 to 8 ring atoms. Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Imino: =NR, wherein R is an imino substituent, for example, for example, hydrogen, a $C_{1-7}$ alkyl group, a $C_{3-20}$ heterocyclyl group, or a $C_{5-20}$ aryl group.

Amidine: —C(=NR)NR$_2$, wherein each R is an amidine substituent, for example, hydrogen, a $C_{1-7}$ alkyl group, a $C_{3-20}$ heterocyclyl group, or a $C_{5-20}$ aryl group. An example of an amidine group is —C(=NH)NH$_2$.

Carbazoyl (hydrazinocarbonyl): —C(O)—NN—R1 wherein R1 is an amino substituent as defined for amino groups. Examples of azino groups include, but are not limited to, —C(O)—NN—H, —C(O)—NN-Me, —C(O)—NN-Et, —C(O)—NN-Ph, and —C(O)—NN—CH$_2$-Ph.

Nitro: —NO$_2$.

Nitroso: —NO.

Azido: —N$_3$.

Cyano (nitrile, carbonitrile): —CN.

Isocyano: —NC.

Cyanato: —OCN.

Isocyanato: —NCO.

Thiocyano (thiocyanato): —SCN.

Isothiocyano (isothiocyanato): —NCS.

Sulfhydryl (thiol, mercapto): —SH.

Thioether (sulfide): —SR, wherein R is a thioether substituent, for example, a $C_{1-7}$ alkyl group (also referred to as a $C_{1-7}$ alkylthio group), a $C_{3-20}$ heterocyclyl group, or a $C_{5-20}$ aryl group. Examples of $C_{1-7}$ alkylthio groups include, but are not limited to, —SCH$_3$ and —SCH$_2$CH$_3$.

Disulfide: —SS—R, wherein R is a disulfide substituent, for example, a $C_{1-7}$ alkyl group (also referred to herein as $C_{1-7}$ alkyl disulfide), a $C_{3-20}$ heterocyclyl group, or a $C_{5-20}$ aryl group. Examples of $C_{1-7}$ alkyl disulfide groups include, but are not limited to, —SSCH$_3$ and —SSCH$_2$CH$_3$.

Sulfone (sulfonyl): —S(=O)$_2$R, wherein R is a sulfone substituent, for example, a $C_{1-7}$ alkyl group, a $C_{3-20}$ heterocyclyl group, or a $C_{5-20}$ aryl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$, —S(=O)$_2$C$_4$F$_9$ (nonaflyl), —S(=O)$_2$CH$_2$CF$_3$ (tresyl), —S(=O)$_2$Ph (phenylsulfonyl), 4-methylphenylsulfonyl (tosyl), 4-bromophenylsulfonyl (brosyl), and 4-nitrophenyl (nosyl).

Sulfine (sulfinyl, sulfoxide): —S(=O)R, wherein R is a sulfine substituent, for example, a $C_{1-7}$ alkyl group, a $C_{3-20}$ heterocyclyl group, or a $C_{5-20}$ aryl group. Examples of sulfine groups include, but are not limited to, —S(=O)CH$_3$ and —S(=O)CH$_2$CH$_3$.

Sulfonyloxy: —OS(=O)₂R, wherein R is a sulfonyloxy substituent, for example, a $C_{1-7}$ alkyl group, a $C_{3-20}$ heterocyclyl group, or a $C_{5-20}$ aryl group. Examples of sulfonyloxy groups include, but are not limited to, —OS(=O)₂CH₃ and —OS(=O)₂CH₂CH₃.

Sulfinyloxy: —OS(=O)R, wherein R is a sulfinyloxy substituent, for example, a $C_{1-7}$ alkyl group, a $C_{3-20}$ heterocyclyl group, or a $C_{5-20}$ aryl group. Examples of sulfinyloxy groups include, but are not limited to, —OS(=O)CH₃ and —OS(=O)CH₂CH₃.

Sulfamino: —NR1S(=O)₂OH, wherein R1 is an amino substituent, as defined for amino groups. Examples of sulfamino groups include, but are not limited to, —NHS(=O)₂OH and —N(CH₃)S(=O)₂OH.

Sulfinamino: —NR1S(=O)R, wherein R1 is an amino substituent, as defined for amino groups, and R is a sulfinamino substituent, for example, a $C_{1-7}$ alkyl group, a $C_{3-20}$ heterocyclyl group, or a $C_{5-20}$ aryl group. Examples of sulfinamino groups include, but are not limited to, —NHS(=O)CH₃ and —N(CH₃)S(=O)C₆H₅.

Sulfamyl: —S(=O)NR1R2, wherein R1 and R2 are independently amino substituents, as defined for amino groups. Examples of sulfamyl groups include, but are not limited to, —S(=O)NH₂, —S(=O)NH(CH₃), —S(=O)N(CH₃)₂, —S(=O)NH(CH₂CH₃), —S(=O)N(CH₂CH₃)₂, and —S(=O)NHPh.

Sulfonamino: —NR1S(=O)2R, wherein R1 is an amino substituent, as defined for amino groups, and R is a sulfonamino substituent, for example, a $C_{1-7}$ alkyl group, a $C_{3-20}$ heterocyclyl group, or a $C_{5-20}$ aryl group. Examples of sulfonamino groups include, but are not limited to, —NHS(=O)₂CH₃ and —N(CH₃)S(=O)₂C₆H₅.

Phosphoramidite: —OP(OR1)-N(R2)₂, where R1 and R2 are phosphoramidite substituents, for example, —H, a $C_{1-7}$ alkyl group, a $C_{3-20}$ heterocyclyl group, or a $C_{5-20}$ aryl group. Examples of phosphoramidite groups include, but are not limited to, —OP(OCH₂CH₃)—N(CH₃)₂, —OP(OCH₂CH₃)—N(i-Pr)₂, and —OP(OCH₂CH₂CN)—N(i-Pr)₂.

Phosphoramidate: —OP(=O)(OR1)-N(R2)₂, where R1 and R2 are phosphoramidate substituents, for example, —H, a $C_{1-7}$ alkyl group, a $C_{3-20}$ heterocyclyl group, or a $C_{5-20}$ aryl group. Examples of phosphoramidate groups include, but are not limited to, —OP(=O)(OCH₂CH₃)—N(CH₃)₂, —OP(=O)(OCH₂CH₃)—N(i-Pr)₂, and —OP(=O)(OCH₂CH₂CN)—N(i-Pr)₂.

In many cases, substituents may themselves be substituted. For example, a $C_{1-7}$ alkoxy group may be substituted with, for example, a $C_{1-7}$ alkyl (also referred to as a $C_{1-7}$ alkyl-$C_{1-7}$ alkoxy group), for example, cyclohexylmethoxy, a $C_{3-20}$ heterocyclyl group (also referred to as a $C_{5-20}$ heterocyclyl-$C_{1-7}$ alkoxy group), for example phthalimidoethoxy, or a $C_{5-20}$ aryl group (also referred to as a $C_{5-20}$ aryl-$C_{1-7}$ alkoxy group), for example, benzyloxy.

Compounds

Compounds that may be used in the methods described herein include compounds of formula (I):

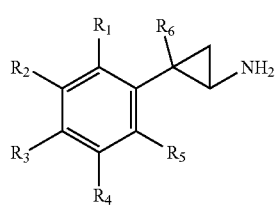

wherein $R_1$, $R_2$, $R_3$, $R_4$ and $R_5$ are independently selected from hydrogen, $C_{1-7}$ alkyl, $C_{3-20}$ heterocyclyl, $C_{5-20}$ aryl, $C_{1-7}$ alkoxy, $C_{1-7}$ haloalkyl, halo, amino, cyano, nitro, ether and thioether, or any two of $R_1$, $R_2$, $R_3$, $R_4$ and $R_5$ may be taken together with the carbon atoms to which they are attached to form an optionally substituted ring; and $R_6$ is selected from hydrogen and optionally substituted $C_{5-20}$ aryl;

or an isomer, prodrug or pharmaceutically acceptable salt thereof.

In some embodiments, at least one of $R_1$, $R_2$, $R_3$, $R_4$ and $R_5$ is not hydrogen. In some embodiments, the compound that may be used in the methods described herein has the following formula (Ia):

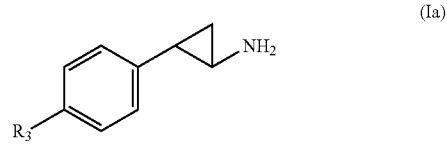

wherein $R_3$ is selected from hydrogen, $C_{1-7}$ alkyl, $C_{3-20}$ heterocyclyl, $C_{5-20}$ aryl, $C_{1-7}$ alkoxy, $C_{1-7}$ haloalkyl, halo, amino, cyano, nitro, ether and thioether; or an isomer, prodrug or salt thereof.

In some embodiments, $R^3$ is halo (e.g., bromo). In some embodiments, $R^3$ is haloalkyl (e.g., trifluoromethyl). In some embodiments, $R^3$ is $C_{1-7}$ alkoxy (e.g., methoxy, ethoxy or isopropoxy). In some embodiments, $R^3$ is ether (e.g., —O-aryl such as —O-phenyl).

Compounds that may be used in the methods described herein include compounds of formula (II):

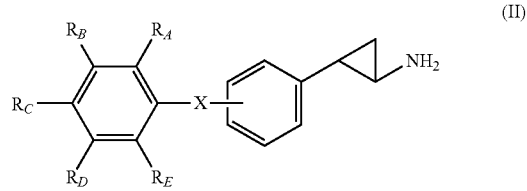

wherein:

X is selected from a bond, O, S, and NH; and $R_A$, $R_B$, $R_C$, $R_D$ and $R_E$ are independently selected from hydrogen, $C_{1-7}$ alkyl, $C_{5-20}$ aryl, $C_{3-20}$ heterocyclyl, $C_{1-7}$ alkoxy, amino, cyano, nitro, halo, haloalkyl, ether and thioether;

or an isomer, prodrug or pharmaceutically acceptable salt thereof.

In embodiments, compounds that may be used in the methods described herein include compounds of formula (III):

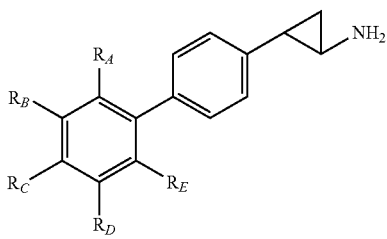

(III)

wherein $R_A$, $R_B$, $R_C$, $R_D$ and $R_E$ are independently selected from hydrogen, $C_{1-7}$ alkyl, $C_{5-20}$ aryl, $C_{3-20}$ heterocyclyl, $C_{1-7}$ alkoxy, amino, cyano, nitro, halo, haloalkyl, ether and thioether; or an isomer, prodrug or pharmaceutically acceptable salt thereof.

In embodiments, compounds that may be used in the methods described herein include compounds of formula (IV):

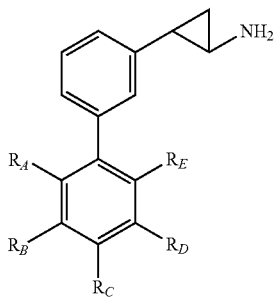

(IV)

wherein $R_A$, $R_B$, $R_C$, $R_D$ and $R_E$ are independently selected from hydrogen, $C_{1-7}$ alkyl, $C_{5-20}$ aryl, $C_{3-20}$ heterocyclyl, $C_{1-7}$ alkoxy, amino, cyano, nitro, halo, haloalkyl, ether and thioether; or an isomer, prodrug or pharmaceutically acceptable salt thereof.

In embodiments, compounds that may be used in the methods described herein include compounds of formula (V):

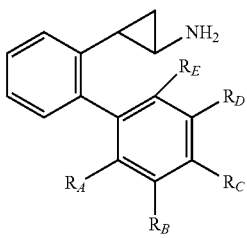

(V)

wherein $R_A$, $R_B$, $R_C$, $R_D$ and $R_E$ are independently selected from hydrogen, $C_{1-7}$ alkyl, $C_{5-20}$ aryl, $C_{3-20}$ heterocyclyl, $C_{1-7}$ alkoxy, amino, cyano, nitro, halo, haloalkyl, ether and thioether; or an isomer, prodrug or pharmaceutically acceptable salt thereof.

In embodiments, compounds that may be used in the methods described herein include compounds of formula (VI):

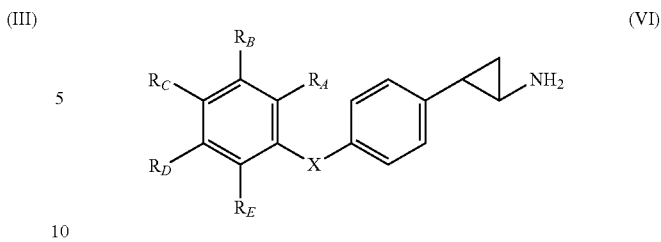

(VI)

wherein $R_A$, $R_B$, $R_C$, $R_D$ and $R_E$ are independently selected from hydrogen, $C_{1-7}$ alkyl, $C_{5-20}$ aryl, $C_{3-20}$ heterocyclyl, $C_{1-7}$ alkoxy, amino, cyano, nitro, halo, haloalkyl, ether and thioether; and X is selected from O, S, and NH; or an isomer, prodrug or pharmaceutically acceptable salt thereof.

In some embodiments, X is O. In some embodiments, X is S. In some embodiments, $R_C$ is $C_{1-7}$ alkyl such as tert-butyl.

In embodiments, compounds that may be used in the methods described herein include compounds of formula (VII):

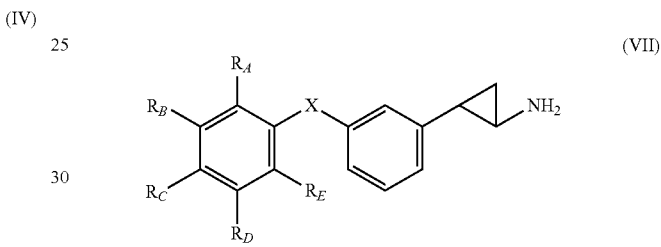

(VII)

wherein $R_A$, $R_B$, $R_C$, $R_D$ and $R_E$ are independently selected from hydrogen, $C_{1-7}$ alkyl, $C_{5-20}$ aryl, $C_{3-20}$ heterocyclyl, $C_{1-7}$ alkoxy, amino, cyano, nitro, halo, haloalkyl, ether and thioether; and X is selected from O, S, and NH; or an isomer, prodrug or pharmaceutically acceptable salt thereof.

In embodiments, compounds that may be used in the methods described herein include compounds of formula (VIII):

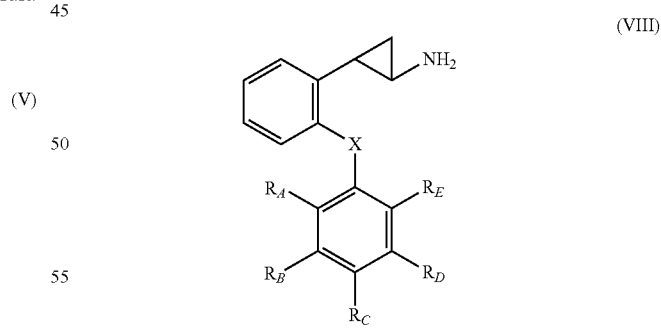

(VIII)

wherein $R_A$, $R_B$, $R_C$, $R_D$ and $R_E$ are independently selected from hydrogen, $C_{1-7}$ alkyl, $C_{5-20}$ aryl, $C_{3-20}$ heterocyclyl, $C_{1-7}$ alkoxy, amino, cyano, nitro, halo, haloalkyl, ether and thioether; and X is selected from a O, S, and NH; or an isomer, prodrug or pharmaceutically acceptable salt thereof.

In embodiments, compounds that may be used in the methods described herein include compounds of formula (IX):

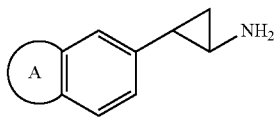

(IX)

wherein:
A is a $C_5$-$C_6$ aryl, cycloalkenyl or heterocyclyl ring;
or an isomer, prodrug or pharmaceutically acceptable salt thereof.

In embodiments, compounds that may be used in the methods described herein include compounds of formula (X):

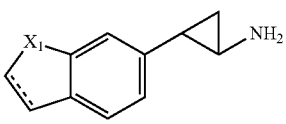

(X)

wherein $X_1$ is selected from $CH_2$, O, S, and NH; and - - - represents the presence or absence of a bond; or an isomer, prodrug or pharmaceutically acceptable salt thereof.

In embodiments, compounds that may be used in the methods described herein include compounds of formula (XI):

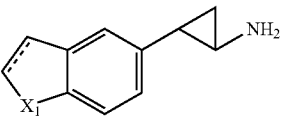

(XI)

wherein $X_1$ is selected from $CH_2$, O, S, and NH; and - - - represents the presence or absence of a bond; or an isomer, prodrug or pharmaceutically acceptable salt thereof.

In embodiments, compounds that may be used in the methods described herein include compounds of formula (XII):

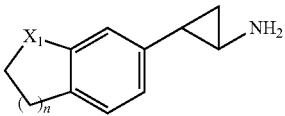

(XII)

wherein $X_1$ is selected from $CH_2$, O, S, and NH; n is 1 or 2; or an isomer, prodrug or pharmaceutically acceptable salt thereof.

In embodiments, compounds that may be used in the methods described herein include compounds of formula (XIII):

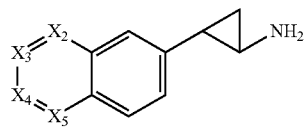

(XIII)

wherein $X_2$, $X_3$, $X_4$ and $X_5$ are independently selected from CH and N; or an isomer, prodrug or pharmaceutically acceptable salt thereof.

In embodiments, compounds that may be used in the methods described herein include compounds of formula (XIV):

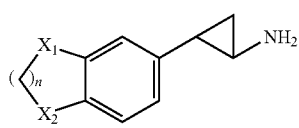

(XIV)

wherein $X_1$ and $X_2$ are independently selected from O and S; and n is 1 or 2; or an isomer, prodrug or pharmaceutically acceptable salt thereof.

In some embodiments, $X_1$ and $X_2$ are O. In some embodiments, n is 1.

In embodiments, compounds that may be used in the methods described herein include compounds of formula (XV):

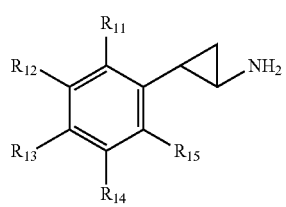

(XV)

wherein $R_{11}$, $R_{12}$, $R_{13}$, $R_{14}$ and $R_{15}$ are independently selected from hydrogen, $C_{1-7}$ alkyl, $C_{3-20}$ heterocyclyl, $C_{2-7}$ alkoxy, amino, cyano, nitro, ether and thioether; or an isomer, prodrug or pharmaceutically acceptable salt thereof.

In some embodiments, $R_{13}$ is $C_{2-7}$ alkoxy, such as ethoxy or isopropoxy. In some embodiments, $R_{13}$ is ether, such as phenoxy or benzyloxy. In some embodiments, $R_{13}$ is amino. In some embodiments, $R_{13}$ is thioether.

In embodiments, compounds that may be used in the methods described herein include compounds of formula (XVI):

(XVI)

where A is an optionally substituted $C_{5-20}$ aryl group, or an isomer, prodrug or pharmaceutically acceptable salt thereof.

Suitable compounds include:

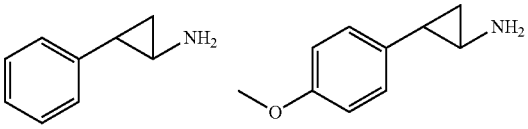

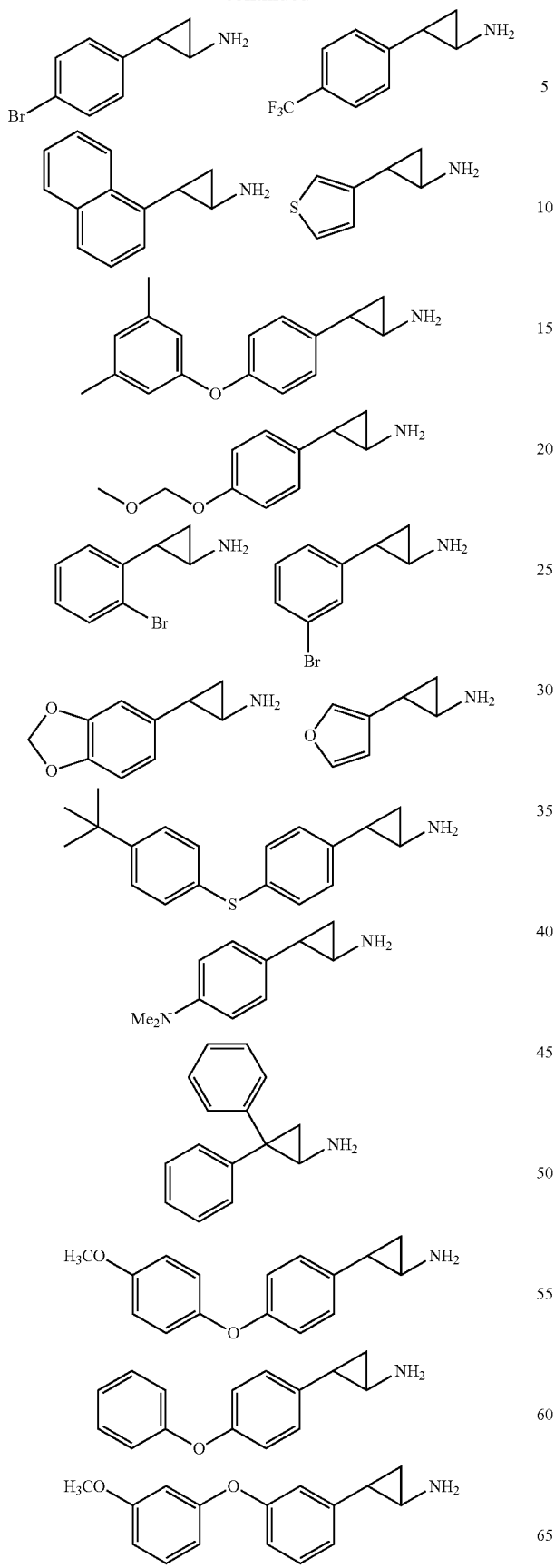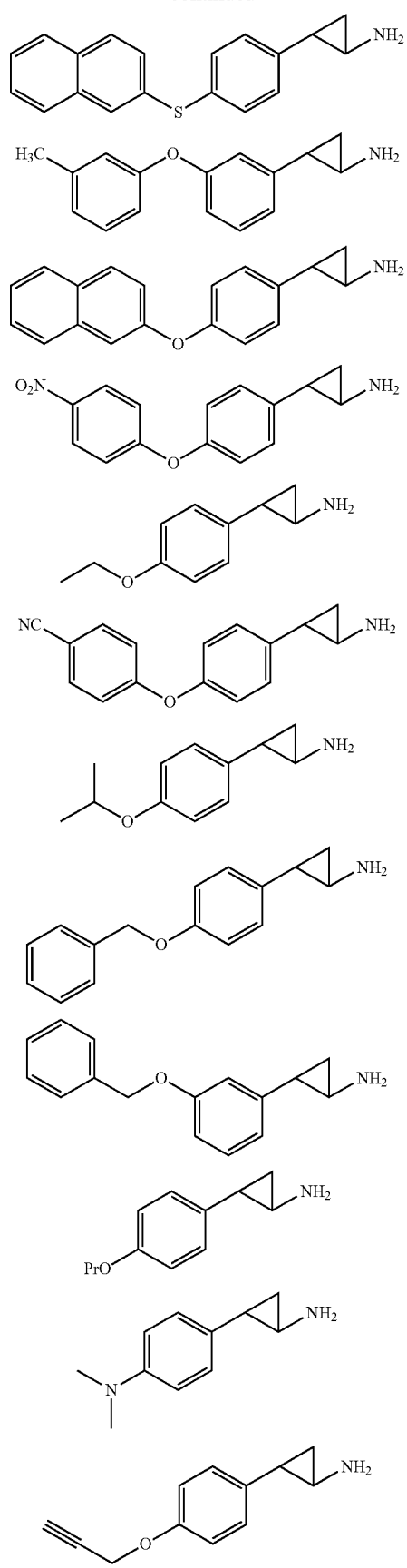

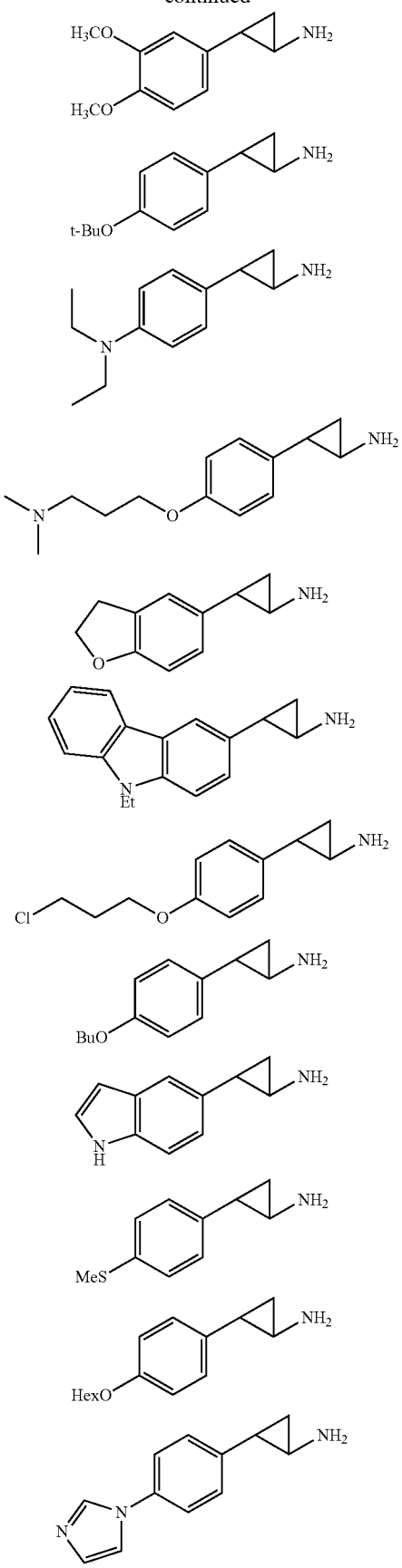

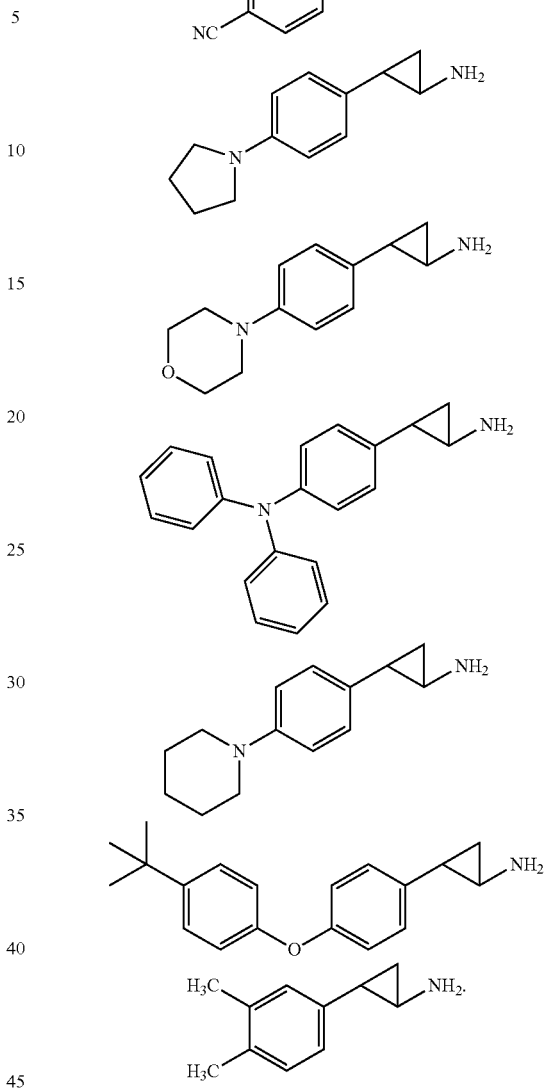

Suitable compounds include those described in U.S. Patent Publication No. 2010/0324147, and in Gooden et al., *Bioorg. Med. Chem. Lett.* 18 (2008) 3047-3051, each of which is incorporated herein by reference in its entirety.

Isomers, Salts, Protected Forms, and Prodrugs

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta chlorophenyl. However, a reference to a class of structures may well include structurally isomeric forms falling within that class (e.g., C$_{1-7}$ alkyl includes n-propyl and iso-propyl; butyl includes n-, iso-, sec-, and tert-butyl; methoxyphenyl includes ortho-, meta-, and paramethoxyphenyl).

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g. asymmetric synthesis) and separation (e.g., fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below. It may be convenient or desirable to prepare, purify, and/or handle a corresponding salt of the active compound, for example, a pharmaceutically-acceptable salt. Examples of pharmaceutically acceptable salts are discussed in Berge et al., *J. Pharm. Sci.*, 66, 1-19 (1977). Exemplary pharmaceutically acceptable salts include hydrochloride salts.

For example, if the compound is anionic, or has a functional group which may be anionic (e.g., —COOH may be —COO—), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: acetic, propionic, succinic, glycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetyoxybenzoic, fumaric, phenylsulfonic, toluenesulfonic, methanesulfonic, ethanesulfonic, ethane disulfonic, oxalic, pantothenic, isethionic, valeric, lactobionic, and gluconic. Examples of suitable polymeric anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form", as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, Protective Groups in Organic Synthesis (T. Green and P. Wuts, Wiley, 1999).

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH$_3$, —OAc). For example, an aldehyde or ketone group may be protected as an acetal or ketal, respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid. For example, an amine group may be protected, for example, as an amide or a urethane, for example, as: a methyl amide (—NHCO—CH$_3$); a benzyloxy amide (—NHCO—OCH$_2$C$_6$H$_5$, —NHCbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH—Fmoc), as a 6-nitroveratryloxy amide (—NH—Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH—Psec); or, in suitable cases, as an N-oxide.

For example, a carboxylic acid group may be protected as an ester for example, as: an C$_{1-7}$ alkyl ester (e.g. a methyl ester; a t-butyl ester); a C$_{1-7}$ haloalkyl ester (e.g., a C$_{1-7}$ trihaloalkylester); a triC$_{1-7}$ alkylsilyl-C$_{1-7}$ alkyl ester; or a C$_{5-20}$ aryl-C$_{1-7}$ alkyl ester (e.g. a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$). It may be convenient or desirable to prepare, purify, and/or handle the active compound in the form of a prodrug.

The term "prodrug", as used herein, pertains to a compound which, when metabolized (e.g. in vivo), yields the desired active compound. Typically, the prodrug is inactive, or less active than the active compound, but may provide advantageous handling, administration, or metabolic properties.

For example, some prodrugs are esters of the active compound (e.g. a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required. Examples of such metabolically labile esters include those wherein R is $C_{1-7}$ alkyl (e.g. -Me, -Et); $C_{1-7}$ aminoalkyl (e.g. aminoethyl; 2-(N,N-diethyl-amino)ethyl; 2-(4-morpholino)ethyl); and acyloxy-$C_{1-7}$ alkyl (e.g. acyloxymethyl; acyloxyethyl; e.g. pivaloyloxymethyl; acetoxymethyl; 1-acetoxyethyl; 1-(1-methoxy-1-methyl)ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexylcarbonyloxyethyl; cyclohexyloxy-carbonyloxymethyl; 1-cyclohexyloxy-carbonyloxyethyl; (4-tetrahydropyranyloxy) carbonyloxymethyl; 1-(4-tetrahydropyranyloxyl)carbonyloxyethyl; (4-tetrahydropyranyl) carbonyloxymethyl; and 1-(4-tetrahydropyranyl) carbonyloxyethyl).

Also, some prodrugs are activated enzymatically to yield the active compound, or a compound which, upon further chemical reaction, yields the active compound. For example, the prodrug may be a sugar derivative or other glycoside conjugate, or may be an amino acid ester derivative.

Synthesis of Compounds

Compounds of the invention may be synthesized according to Scheme 1. For example, an α,β-unsaturated carboxylic acid may be protecting with an acid protecting group (e.g., as an ester such as a methyl ester). Cyclopropanation may be effected by a number of methods, such as use of the Corey-Chaykovsky reagent, or diazomethane in the presence of a catalyst (e.g., palladium(II) acetate). Subsequent deprotection (e.g., via hydrolysis) may be followed by conversion of the carboxylic acid to a primary amine, e.g., via Curtius rearrangement or a Hofmann rearrangement.

The starting material may be a commercially available α,β-unsaturated acid. Alternatively, an appropriate alkene may be generated from the corresponding aryl aldehyde via an olefination reaction (e.g., the Horner-Wadsworth-Emmons reaction). Additional non-commerically available substituted benzaldehydes for olefination can be prepared using a cross-coupling reaction (e.g., a copper-catalyzed Ullmann coupling) between para-halobenzaldehydes and a variety of phenols and thiophenols, as illustrated in Scheme 2.

Scheme 2.

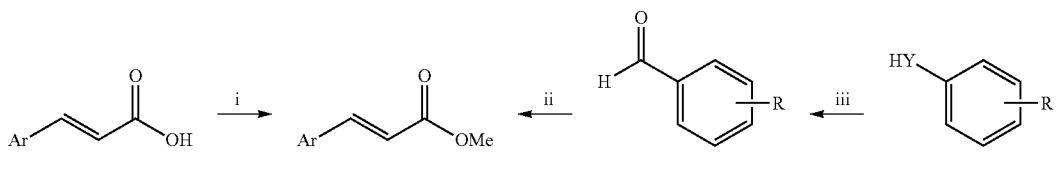

(i) esterification; (ii) olefination; (iii) cross-coupling. Y=O or S. R=Br or I.

As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCR Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Evaluating Compounds

A variety of methods can be used to evaluate a compound for its potential use in treatment of Parkinson's disease. Evaluation methods include in vitro assays, in vitro cell-based assays, ex vivo assays and in vivo methods. The methods can evaluate binding to a protein or enzyme, an activity downstream of a protein or enzyme of interest, or treatment or alleviation of symptoms.

For anti-Parkinsonian drug candidate screening, compounds can be tested using a mouse model of PD akinesia. See, e.g., Sotnikova et al. *PLoS Biol.*, 2005, 3, p. e271; and Sotnikova et al. *Neurology*, 2006, 67, p. S12-17. These mice contain a heterozygous knockout of the dopamine uptake transporter (DAT), termed DAT-KO mice, and then may be conditionally rendered nearly devoid of dopamine (0.02% of wild-type) by treatment with an inhibitor of the rate limiting dopamine biosynthesis enzyme tyrosine hydroxylase, α-methyl-p-tyrosine (α-MT). These dopamine depleted DAT-KO mice (DDD) exhibit a very specific akinetic phenotype almost immediately after treatment with α-MT. In agreement with neurochemical data, the recovery from this profound phenotype occurs approximately 16-24 h following α-MT treatment.

This model has demonstrated that L-DOPA alone or given along with carbidopa (CD) fully restored locomotion in DDD mice. These treatments temporarily restored locomotion essentially up to the levels normally observed in intact Scheme 1.

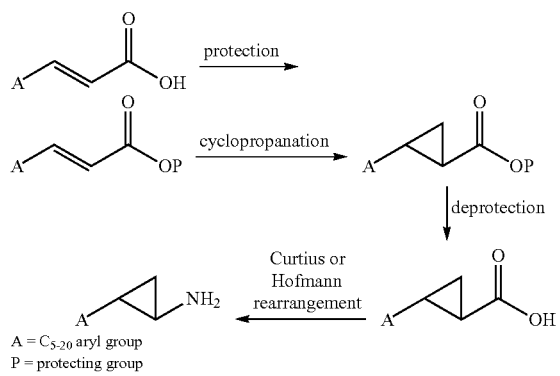

A = $C_{5-20}$ aryl group
P = protecting group

DAT-KO mice. Similarly, the non-selective D1/D2 DA agonists apomorphine and pergolide were effective in treating akinesia, as well as combined administration of the D1 and D2 agonists SKF81297 plus quinpirole, supporting cooperative interaction of D1/D2 DA receptors in locomotor activity (Sotnikova et al. *PLoS Biol.*, 2010, 5, p. e13452). Accordingly, DDD mice may be very useful models of PD. Compounds described herein may thus be evaluated using this model for their abilities to restore locomotion in DDD mice.

Compounds described herein may also be evaluated in other widely accepted animal models of Parkinson's disease. For example, compounds may be evaluated in rats that have been treated with 6-hydroxydopamine (6-OHDA). See Heidenreich et al. (2004) *Exp Neurol* 186:145-157; Heidenreich et al. (1995) *J Pharmacol Exp Ther* 273:516-525; Turner et al. (2008) *Brain Struct Funct* 213:197-213; and Turner et al. (2002) *J Pharmacol Exp Ther* 301:371-381. Compounds may also be evaluated in squirrel monkeys made Parkinsonian by injections of MPTP. This is a validated model of PD that is well established at the Parkinson's Institute. Animals may be drawn from a cohort of MPTP-lesioned animals that have shown stable Parkinsonism scores over a period of more than 8 months. MPTP-treated squirrel monkeys offer a faithful model of PD including a therapeutic response to LD/CD treatment that produces significant reductions in Parkinsonian motor deficits in these animals. Importantly, MPTP-lesioned animals given LD/CD also develop abnormal involuntary movements (dyskinesias) that are quantifiable and nearly identical to those observed in LD treated patients (Langston et al. *Ann Neurol* 47, S79-89 (2000); Quik et al. *Ann Neurol* 62, 588-96 (2007); Hsu et al. *J Pharmacol Exp Ther* 311, 770-7 (2004); Togasaki et al. *Ann Neurol* 50, 254-7 (2001); Togasaki et al. *Neuropharmacology* 48, 398-405 (2005)).

Treatment of Parkinson's Disease

Parkinson's disease (PD) is a debilitating neurological illness that affects an estimated 6 million people worldwide; in 2007, it was the 14$^{th}$ leading cause of death in the United States. PD is largely characterized by the irreversible loss of brain dopamine (DA) neurons. DA neurotransmission is essential for normal locomotor functions and, in most cases, PD becomes clinically apparent when the loss of dopaminergic neurons reaches 60-70% leading to functional dysregulation of the related neuronal circuitry. Major motor and non-motor manifestations of DA deficiency in PD include tremors, rigidity, bradykinesia, cardiovascular and gastrointestinal abnormalities, cognitive dysfunction, and depression.

Currently, there is no known cure for PD. However, the symptoms can be controlled by therapeutic interventions. DA replacement therapy is the major medical approach to treating PD, and a variety of dopaminergic agents are available. The most powerful drug is the immediate precursor to dopamine, levodopa (L-DOPA). Although L-DOPA is the most effective drug to treat the symptoms of PD, after five years or less of treatment about 60% of patients develop complications including fluctuations in motor performance as well as psychotic reactions and dyskinesia. DA agonists, as well as several other classes directly or indirectly affecting DA function (monoamine oxidase (MAO) inhibitors and catechol-O-methyl transferase (COMT) inhibitors) have proven advantageous in PD patients but are typically effective only when administered at early stages of the disease or as supplementary medications to enhance the benefits of L-DOPA.

In an aspect, the disclosure provides a method of treating Parkinson's disease in a subject in need of treatment, comprising administering to the subject an effective amount of a compound of any of formulae (I)-(XVI) as described herein.

In another aspect, the disclosure provides a method of treating Parkinson's disease in a subject in need of treatment, comprising administering to the subject an effective amount of a compound of any of formulae (I)-(XVI) as described herein, and L-3,4-dihydroxyphenylalanine (L-DOPA).

In a further aspect, the disclosure provides a method of treating or reducing dyskinesia in a subject in need thereof, comprising administering to the subject an effective amount of a compound of any of formulae (I)-(XVI) as described herein.

In yet a further aspect, the disclosure provides a method of treating or reducing dyskinesia in a subject in need thereof, comprising administering to the subject an effective amount of a compound of any of formulae (I)-(XVI) as described herein, wherein the dyskinesia is induced by, or associated with, L-3,4-dihydroxyphenylalanine (L-DOPA).

As used herein, "dyskinesia" relates to a movement disorder which is typically characterized or indicated by involuntary, repetitive body movements, along with diminished voluntary movement. Dyskinesia can manifest itself broadly, from a slight tremor of the mouth or hands to uncontrollable movement of the upper (commonly) or lower body. Dyskinesia can be a symptom of any of several medical disorders and is distinguished by the underlying cause. Chronic (or tardive) is a late onset dyskinesia, which typically occurs after treatment with antipsychotic drugs (e.g., haloperidol or amoxapine). Common symptoms include tremors and writhing movements of the body and limbs and, less frequently, movement in the face and mouth. It may also involve involuntary lip smacking, repetitive pouting of the lips and tongue protrusions.

In some embodiments, the methods disclosed herein relate to treating or reducing dyskinesia that is associated with the movement disorder commonly observed in patients with Parkinson's disease, also referred to as Levodopa-induced dyskinesia (LID). This form of dyskinesia commonly manifests itself in the form of jerky, dance-like movements of the arms and/or head, and usually presents after several years of treatment with L-DOPA (Levodopa).

The term "effective amount" as used herein, pertains to that amount of an active compound, or a material, composition or dosage from comprising an active compound, which produces some desired effect, such as alleviation of symptoms or alleviation of side effects.

The term "treatment", as used herein in the context of treating a condition, pertains generally to treatment and therapy, whether of a human or an animal (e.g. in veterinary applications), in which a desired therapeutic effect is achieved. For example, treatment may ameliorate the condition or may inhibit the progress of the condition (e.g., reduce the rate of progress or halt the rate of progress), or may alleviate symptoms of the condition, or may alleviate side-effects of treatment with other agents (e.g., dyskinesia).

The term "therapeutically-effective amount" as used herein, pertains to that amount of an active compound, or a material, composition or dosage form comprising an active compound, which is effective for producing some desired therapeutic effect, commensurate with a reasonable benefit/risk ratio.

Administration

The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly.

In some embodiments, co-administration of an effective amount of a compound of any of formulae (I)-(XVI) and L-3,4-dihydroxyphenylalanine (L-DOPA) may be used in combination and optionally with other known PD therapies. Administered "in combination," as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the overall treatment is more effective because of combined administration. For example, the L-DOPA treatment is more effective, e.g., an equivalent effect is seen with less L-DOPA, one or more deleterious effects associated with L-DOPA therapy are reduced, or the L-DOPA treatment reduces PD symptoms to a greater extent, than would be seen if the L-DOPA were administered in the absence of the compounds disclosed herein. Conversely, the analogous situation can be observed wherein the compounds of formulae (I)-(XVI) are more effective when administered in combination with L-DOPA. In some embodiments, delivery is such that the reduction in a symptom, or other parameter related to the disorder is greater than what would be observed with one treatment delivered in the absence of the other. The effect of the two treatments can be partially additive, wholly additive, or greater than additive (synergistic).

The compounds of formulae (I)-(XVI) and L-DOPA, and optionally at least one additional therapeutic agent can be administered simultaneously, in the same or in separate compositions, or sequentially. For sequential administration, either the compounds of formulae (I)-(XVI) or the L-DOPA can be administered first, or the order of administration can be reversed. Similarly, any optional additional therapeutic agent(s) can be administered prior to or after administration of the compounds of formulae (I)-(XVI) and/or L-DOPA.

Accordingly, in some embodiments, the methods relate to a method for treating Parkinson's disease and/or a symptom associated with Parkinson's disease, wherein the method comprises administration of a dose-spared amount of L-DOPA, or a composition comprising a dose-spared amount of L-DOPA. As used herein, "dose-spared" amount of L-DOPA means that the effective amount of L-DOPA is reduced relative to the effective amount that would commonly be required to exert the desired beneficial effect. Thus, in certain embodiments, the disclosure provides for compositions and formulations that comprise an effective amount of at least one compound of formulae (I)-(XVI) and a dose-spared amount of L-DOPA.

The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutan, gibbon), or a human.

Formulations

While it is possible for the active compound to be administered alone, it can be formulated as a pharmaceutical composition (e.g. formulation) comprising at least one active compound, as defined above, together with one or more pharmaceutically acceptable carriers, adjuvants, excipients, diluents, fillers, buffers, stabilizers, preservatives, lubricants, or other materials well known to those skilled in the art and optionally other therapeutic or prophylactic agents.

Thus, the disclosure further provides pharmaceutical compositions, as defined above, and methods of making a pharmaceutical composition comprising admixing at least one active compound, as defined above, together with one or more pharmaceutically acceptable carriers, excipients, buffers, adjuvants, stabilizers, or other materials, as described herein.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, excipients, etc. can be found in standard pharmaceutical texts, for example, Remington's Pharmaceutical Sciences, 18th edition, Mack Publishing Company, Easton, Pa., 1990.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, losenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or moulding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g. transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include lozenges comprising the active compound in a flavored basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the active compound.

Formulations suitable for administration by inhalation include those presented as an aerosol spray from a pressurized pack, with the use of a suitable propellant, such as dichlorodifluoromethane, trichlorofluoromethane, dichorotetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Suitable emulgents and emulsion stabilizers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as diisoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g. by injection, including cutaneous, subcutaneous, intramuscular, intravenous and intradermal), include aqueous and nonaqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

In some embodiments, the disclosure provides a pharmaceutical composition comprising a compound having the following formula:

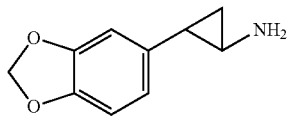 [SMILES: NC1CC1c1ccc2c(c1)OCO2]

or a pharmaceutically acceptable salt thereof, and a pharmaceutically acceptable carrier.

Dosages

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 μg to about 250 mg per kilogram body weight of the subject per day. Where the active compound is a salt, an ester, prodrug, or the like, the amount administered is calculated on the basis of the parent compound and so the actual weight to be used is increased proportionately.

EXAMPLES

General Considerations

Unless stated to the contrary, where applicable, the following conditions apply. Air sensitive reactions were carried out using dried solvents (see below) and under a slight static pressure of Ar (pre-purified quality) that had been passed through a column of Drierite. Glassware was dried in an oven at 120° C. for at least 12 h prior to use and then assembled quickly while hot, sealed with rubber septa, and allowed to cool under a stream of Ar. Reactions were stirred magnetically using Teflon-coated magnetic stirring bars. Teflon-coated magnetic stirring bars and syringe needles were dried in an oven at 120° C. for at least 12 h prior to use. Commercially available Norm-Ject disposable syringes were used. All $^1$H and $^{13}$C NMR spectra were recorded on 300 MHz or 400 MHz Varian Mercury spectrometers as noted. $^1$H spectra were referenced to CHCl$_3$ at 7.26 ppm and $^{13}$C spectra were referenced to CDCl$_3$ at 77.23 ppm. All spectra were taken in CDCl$_3$ unless otherwise noted. Thin layer chromatography (TLC) was carried out on Merck silica gel 60 F$_{254}$ aluminum backed plates and visualized using 254 nm UV light. Flash chromatographic purifications were performed using silica gel (40-60 μm) purchased from Agela Technologies (Newark, Del.). Compounds and solvents were obtained from Fisher, Sigma-Aldrich, and VWR and used without further purification unless noted below.

Example 1

Synthesis of Ethers

The following example is representative for the formation of all diaryl ethers from their respective phenols or thiophenols and para-bromobenzaldehyde.

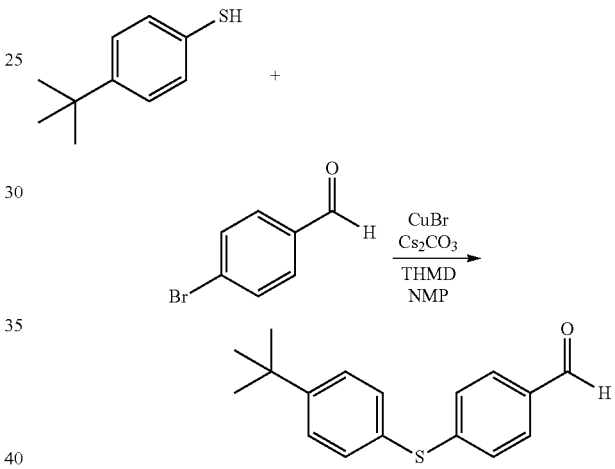

4-(4-tert-butylphenylthio)benzaldehyde: Under argon, an oven dried round bottom flask was charged with the 4-tert-butylthiophenol (0.69 mL, 4 mmol, 2 eq) and anhydrous N-methyl-2-pyrrolidone (5 mL). Cesium carbonate (1.3 g, 4 mmol, 2 eq) was added to the stirring solution and it immediately turned cloudy. Para-bromobenzaldehyde (370 mg, 2 mmol, 1 eq) was added, followed by copper (I) bromide (143 mg, 1 mmol, 0.5 eq) and 2,2,6,6-tetramethyl-3,5-heptanedione (41 μL, 0.2 mmol, 0.1 eq). The flask was equipped with a reflux condenser and heated to 70-80° C. for 15.5 h while stirring. After cooling to rt, the reaction mixture was diluted with methyl tert-butyl ether (100 mL) and vacuum filtered. The residue was washed with MTBE (100 mL) and the combined filtrates were washed with 2 N HCl (100 mL), 0.6 N HCl (100 mL), 2 M NaOH (100 mL), and saturated NaCl (100 mL). The organic layer was dried over MgSO$_4$, filtered, and concentrated in vacuo. The desired 4-(4-tert-butylphenylthio)benzaldehyde was isolated by flash chromatography over silica gel with 10:1 hexanes:ethyl acetate to afford a gold oil in 62% yield (0.065 g). $^1$H NMR (400 MHz, CDCl$_3$): δ9.88 (1H, s), 7.69 (2H, d, J=8.4 Hz), 7.44 (4H, m), 7.20 (2H, d, J=8.4 Hz), 1.34 (9H, s). $^{13}$C NMR (100 MHz, CDCl$_3$): δ191.2, 152.7, 148.0, 134.4, 133.5, 130.1, 127.3, 126.9, 126.7, 34.8, 31.2.

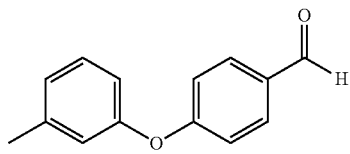 [SMILES: Cc1cccc(Oc2ccc(C=O)cc2)c1]

4-(m-tolyloxy)benzaldehyde: 0.049 g, 54%, white solid. $^1$H NMR (300 MHz, CDCl$_3$): δ9.92 (1H, s), 7.83 (2H, m), 7.27 (1H, m), 7.03 (3H, m), 6.90 (2H, m), 2.36 (3H, s). $^{13}$C NMR (75 MHz, CDCl$_3$): δ191.0, 132.2, 130.1, 126.0, 121.3, 117.8, 117.6, 21.6.

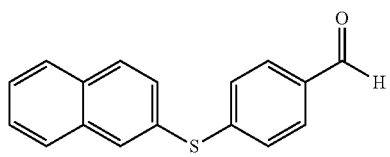 [SMILES: O=Cc1ccc(Sc2ccc3ccccc3c2)cc1]

4-(naphthalen-2-ylthio)benzaldehyde: 0.071 g, 60%, off-white solid. $^1$H NMR (400 MHz, CDCl$_3$): δ9.90 (1H, s), 8.07 (1H, s), 7.82 (3H, m), 7.70 (2H, m), 7.54 (3H, m), 7.27 (2H, m). $^{13}$C NMR (100 MHz, CDCl$_3$): δ191.2, 147.1, 134.0, 133.8, 133.7, 133.1, 130.7, 130.2, 129.6, 127.9, 127.8, 127.3, 127.2, 126.9.

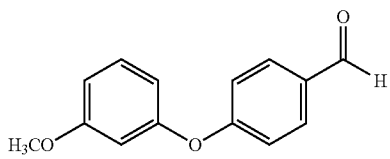 [SMILES: COc1cccc(Oc2ccc(C=O)cc2)c1]

4-(3-methoxyphenoxyl)benzaldehyde: 0.204 g, 44%, yellow oil. $^1$H NMR (300 MHz, CDCl$_3$): δ9.89 (1H, s), 7.83 (2H, m), 7.28 (1H, m), 7.07 (2H, m), 6.77 (1H, m), 6.66 (2H, m), 3.77 (3H, s). $^{13}$C NMR (75 MHz, CDCl$_3$): δ190.6, 162.8, 161.0, 156.0, 131.8, 131.2, 130.4, 117.5, 112.2, 110.4, 106.2, 55.2.

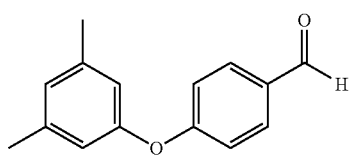 [SMILES: Cc1cc(C)cc(Oc2ccc(C=O)cc2)c1]

4-(3,5-dimethylphenoxyl)benzaldehyde: 0.176 g, 38%, gold oil. $^1$H NMR (300 MHz, CDCl$_3$): δ9.91 (1H, s), 7.82 (2H, m), 7.03 (2H, m), 6.85 (1H, s), 6.70 (2H, s), 2.31 (6H, s). $^{13}$C NMR (75 MHz, CDCl$_3$): δ191.0, 163.7, 155.2, 140.3, 132.2, 131.3, 126.9, 118.3, 117.7, 21.5.

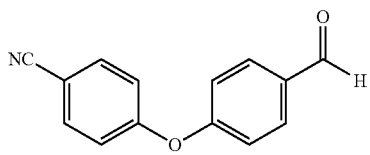 [SMILES: N#Cc1ccc(Oc2ccc(C=O)cc2)cc1]

4-(4-formylphenoxyl)benzonitrile: 0.082 g, 18%, gold solid. $^1$H NMR (400 MHz, CDCl$_3$): δ9.98 (1H, s), 7.92 (2H, m), 7.68 (2H, m), 7.15 (4H, m). $^{13}$C NMR (100 MHz, CDCl$_3$): δ190.9, 159.8, 134.7, 133.0, 132.4, 128.8, 119.9, 119.7, 118.6, 107.9.

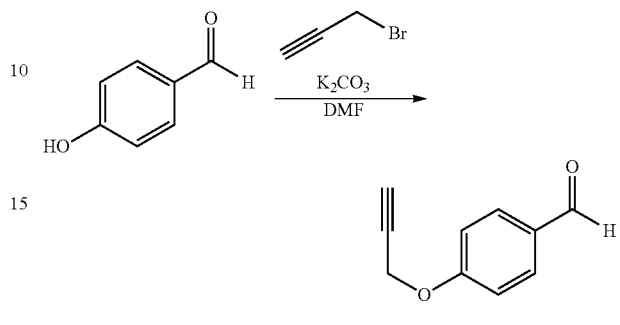

4-(prop-2-ynyloxy)benzaldehyde: An oven-dried round bottom flask was charged with anhydrous dimethylformamide (35 mL), 4-hydroxybenzaldehyde (2.08 g, 16.4 mmol, 1 eq) and anhydrous potassium carbonate (6.80 g, 49.2 mmol, 3 eq) and was stirred at 55° C. for 30 min. The reaction mixture was cooled to rt and propargyl bromide (1.75 mL, 19.7 mmol, 1.2 eq) was added. The reaction was stirred for an additional 5 h at rt. The crude reaction mixture was poured on ice water (100 mL) and stirred for 10 min. The desired 4-(prop-2-ynyloxybenzaldehyde) was isolated by vacuum filtration and dried in vacuo over CaSO$_4$ to afford a brown solid in 92% yield (2.520 g). $^1$H NMR (300 MHz, CDCl$_3$): δ9.90 (1H, s), 7.86 (2H, m), 7.10 (2H, m), 4.79 (2H, d, J=2.7 Hz), 2.57 (1H, J=2.4 Hz). $^{13}$C NMR (75 MHz, CDCl$_3$): δ191.0, 132.1, 115.4, 76.6, 56.2.

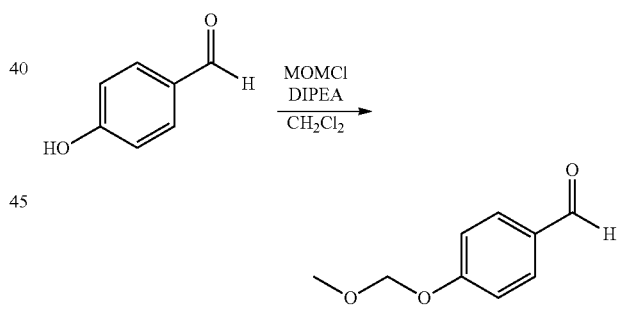

4-(methoxymethoxy)benzaldehyde: Diisopropylethylamine (7.1 mL, 41 mmol, 2.5 eq) was added slowly dropwise to a stirring solution of 4-hydroxybenzaldehyde (2.0 g, 16.4 mmol, 1 eq) in dichloromethane (50 mL). Chloromethyl methyl ether (1.9 mL, 24.6 mmol, 1.5 eq) was added slowly producing a gas. The reaction was stirred at rt for 1.25 h. The reaction was quenched by adding water (50 mL). The organic products were extracted with ethyl acetate (3×25 mL), dried with anhydrous Na$_2$SO$_4$ and concentrated to a golden oil under reduced pressure. The desired 4-(methoxymethoxy)benzaldehyde was isolated by flash chromatography over silica gel with 4:1 hexanes:ethyl acetate to afford a clear colorless oil in 83% yield (2.227 g). $^1$H NMR (400 MHz, CDCl$_3$): δ9.87 (1H, s), 7.82 (1H, d, J=8.8 Hz), 7.14 (2H, d, J=8.8 Hz), 5.24 (2H, s), 3.47 (3H, s). $^{13}$C NMR (100 MHz, CDCl$_3$): δ191.0, 162.3, 131.9, 130.8, 116.4, 56.4.

Example 2

Synthesis of Methyl Esters from Cinnamic Acids

The following example is representative for the formation of all methyl esters from their respective cinnamic acids with acidic methanol.

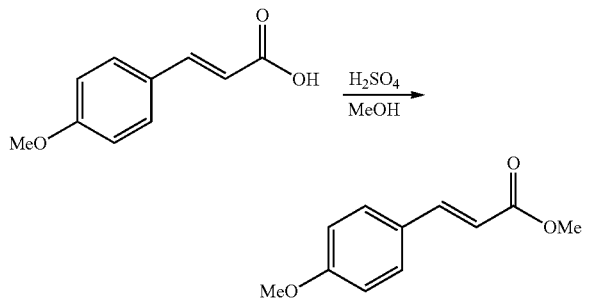

(E)-methyl 3-(4-methoxyphenyl)acrylate: In a round bottom flask, 4-methoxycinnamic acid (3.14 g, 17 mmol, 1 eq) was suspended in methanol (20 mL). Sulfuric acid (650 µL) was added dropwise. The reaction was brought to 70° C. and allowed to reflux for 3.5 hours, until starting material was consumed as observed by TLC. The crude reaction mixture was poured on ice water (30 mL). The organic products were extracted with ether (1×60 mL, 2×30 mL), washed with brine (30 mL) and dried using anhydrous MgSO₄. The crude product was concentrated in vacuo. The desired (E)-methyl 3-(4-methoxyphenyl)acrylate was isolated by flash chromatography using 5:1 hexanes:ethyl acetate to afford a white solid in 96% yield (3.241 g). $^1$H NMR (300 MHz, CDCl₃): δ7.61 (1H, d, J=15.9 Hz), 7.41 (2H, d, J=8.7 Hz), 6.84 (2H, d, J=8.7 Hz), 6.27 (1H, d, J=15.9 Hz), 3.83 (3H, s), 3.79 (3H, s). $^{13}$C NMR (75 MHz, CDCl₃): δ7.8, 161.6, 144.6, 129.9, 127.2, 115.3, 114.4, 55.4, 51.6.

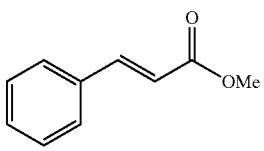 [SMILES: COC(=O)/C=C/c1ccccc1]

Methyl cinnamate: 7.947 g, 73%, white solid. $^1$H NMR (400 MHz, CDCl₃): δ7.70 (1H, d, J=16 Hz), 7.51 (2H, m), 7.37 (2H, m), 6.46 (1H, d, J=1.8 Hz), 6.42 (1H, d, J=1.8 Hz), 3.81 (3H, s). $^{13}$C NMR (100 MHz, CDCl₃): δ145.1, 134.6, 130.5, 129.1, 128.3, 118.1, 51.9.

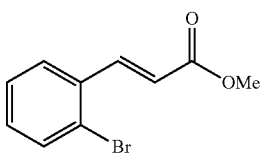 [SMILES: COC(=O)/C=C/c1ccccc1Br]

(E)-methyl 3-(2-bromophenyl)acrylate: 0.094 g, 89%, light gold oil. $^1$H NMR (300 MHz, CDCl₃): δ8.05 (1H, d, J=15.9 Hz), 7.58 (2H, m), 7.29 (2H, m), 6.39 (1H, d, J=15.9 Hz), 3.82 (3H, s).

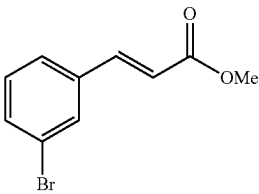 [SMILES: COC(=O)/C=C/c1cccc(Br)c1]

(E)-methyl 3-(3-bromophenyl)acrylate: 1.622 g, 77%, white solid. $^1$H NMR (300 MHz, CDCl₃): δ7.50 (1H, d, J=16.2 Hz), 7.44 (1H, s), 7.36 (1H, d, J=8.1 Hz), 7.28 (1H, d, J=8.1 Hz), 7.10 (1H, t, J=7.8 Hz), 6.30 (1H, J=16.2 Hz), 3.70 (3H, s). $^{13}$C NMR (100 MHz, CDCl₃): δ167.0, 143.2, 136.6, 133.2, 130.9, 130.5, 126.8, 123.2, 119.4.

Example 3

Synthesis of Methyl Esters from Cinnamic Acids with TMSCHN₂

The following example is representative for the formation of all methyl esters from their respective cinnamic acids with TMSCHN₂.

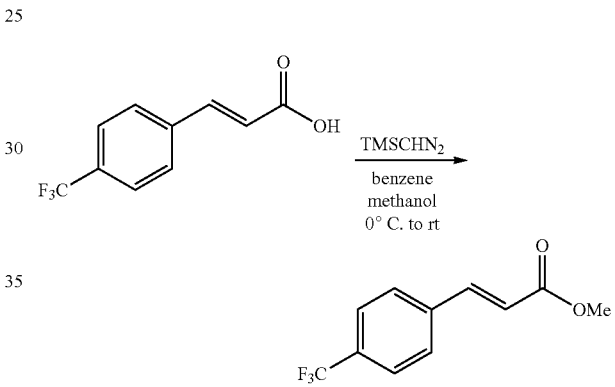

(E)-methyl 3-(4-trifluoromethyl)phenyl)acrylate: A solution of TMSCHN₂ (2.0 M in hexanes, 1.6 eq) was added dropwise with stirring to a 0° C. solution of the (E)-3-(4-(trifluoromethyl)phenyl)acrylic acid (0.25 M) in benzene: methanol (2:1). The reaction was allowed to warm to rt over the course of 0.5 h. Concentration of the reaction mixture afforded the desired (E)-methyl 3-(4-trifluoromethyl)phenyl)acrylate as a white solid in 99% yield (0.898 g). $^1$H NMR (300 MHz, CDCl₃): δ7.69 (1H, d, J=15.9 Hz), 7.62 (4H, m), 6.50 (1H, d, J=15.9 Hz), 3.87 (3H, s). $^{13}$C NMR (75 MHz, CDCl₃): δ167.0, 143.2, 138.0, 128.4, 126.1, 126.0, 120.6, 52.1.

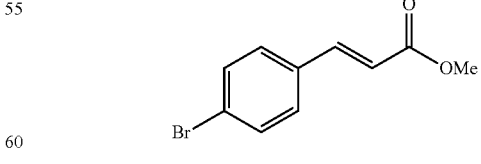

(E)-methyl 3-(4-bromophenyl)acrylate: 1.47 g, 99%, off-white solid. $^1$H NMR (300 MHz, CDCl₃): δ7.62 (1H, d, J=15.9 Hz), 7.51 (2H, d, J=8.1 Hz), 7.37 (2H, d, J=8.1 Hz), 6.42 (1H, d, J=15.9 Hz), 3.80 (3H, s). $^{13}$C NMR (75 MHz, CDCl₃): δ167.4, 143.7, 133.5, 132.4, 129.7, 124.8, 118.7, 52.0.

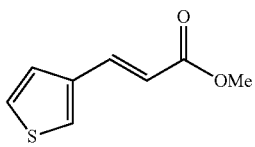 [SMILES: COC(=O)/C=C/c1ccsc1]

(E)-methyl 3-(thiophen-3-yl)acrylate: 1.22 g, 99%, light brown solid. $^1$H NMR (300 MHz, CDCl$_3$): δ7.67 (1H, d, J=15.6 Hz), 7.49 (1H, m), 7.29 (1H, m), 7.33 (1H, m), 6.26 (1H, d, J=15.6 Hz), 3.79 (3H, s). $^{13}$C NMR (75 MHz, CDCl$_3$): δ167.9, 138.6, 137.8, 128.3, 127.2, 125.4, 117.7, 51.9.

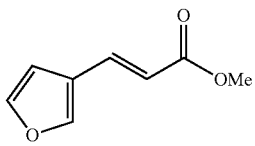 [SMILES: COC(=O)/C=C/c1ccoc1]

(E)-methyl 3-(furan-3-yl)acrylate: 1.11 g, 98%, off-white solid. $^1$H NMR (300 MHz, CDCl$_3$): δ7.63 (1H, s), 7.56 (1H, d, J=15.6 Hz), 7.41 (1H, s), 6.57 (1H, s), 6.14 (1H, d, J=15.6 Hz), 3.76 (3H, s). $^{13}$C NMR (75 MHz, CDCl$_3$): δ167.6, 144.7, 144.6, 135.0, 122.8, 117.8, 107.6, 51.8.

Example 4

Synthesis of Trans-Alkenes Via Horner-Wadsworth-Emmons Olefination

The following example is representative for the formation of all trans-alkenes from the corresponding benzaldehyde and methyl diethylphosphonoacetate through a Horner-Wadsworth-Emmons olefination.

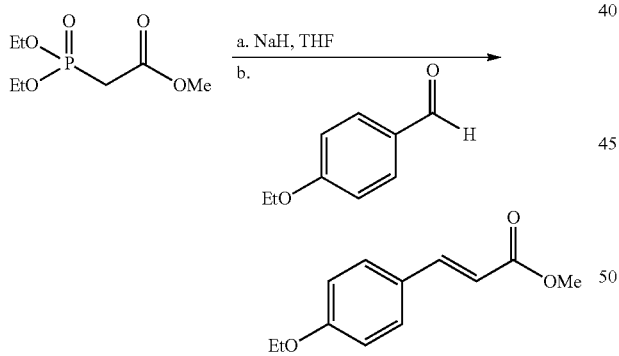

(E)-methyl 3-(4-ethoxyphenyl)acrylate: Under argon, sodium hydride (252 mg, 10 mmol, 1.7 eq) was dissolved in anhydrous THF (40 mL) in an oven dried round bottom flask and cooled to 0° C. Methyl diethyl phosphonoacetate (1.7 mL, 9.6 mmol, 1.6 eq) was added dropwise and stirred for 45 min while allowing to warm to rt. In round bottom flask under argon, para-ethoxybenzaldehyde (830 μL, 6 mmol, 1.0 eq) was dissolved in anhydrous toluene (60 mL) and cooled to −78° C. The phosphonate anion solution was transferred to the aldehyde via cannula and the reaction was allowed to warm to rt over the course of 6.75 h. Saturated Rochelle's salt (20 mL) was added and stirred for 10 min. CH$_2$Cl$_2$ (20 mL) and deionized water (20 mL) was added and the layers separated. The organic products were extracted with CH$_2$Cl$_2$ (3×30 mL), dried over anhydrous Na$_2$SO$_4$ and the solvent was removed under reduced pressure. The desired (E)-methyl 3-(4-ethoxyphenyl)acrylate was isolated by flash chromatography using 100% CH$_2$Cl$_2$ to yield a white solid in 95% yield (1.164 g). $^1$H NMR (300 MHz, CDCl$_3$): δ7.64 (1H, d, J=15.9 Hz), 7.46 (2H, d, J=8.7 Hz), 6.88 (2H, d, J=8.7 Hz), 6.30 (1H, d, J=15.9 Hz), 4.05 (2H, q, J=6.9 Hz), 4.79 (3H, s), 1.42 (3H, t, J=6.9 Hz). $^{13}$C NMR (75 MHz, CDCl$_3$): δ168.0, 161.0, 144.8, 129.9, 127.2, 115.3, 115.1, 63.8, 51.8, 14.9.

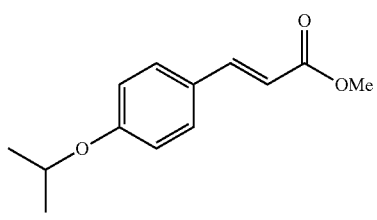 [SMILES: COC(=O)/C=C/c1ccc(OC(C)C)cc1]

(E)-methyl 3-(4-isopropoxyphenyl)acrylate: 0.651 g, 95%, clear, colorless oil. $^1$H NMR (300 MHz, CDCl$_3$): δ7.62 (1H, d, J=15.9 Hz), 7.37 (2H, m), 6.91 (2H, m), 6.20 (1H, d, J=15.9 Hz), 3.74 (3H, s), 2.96 (6H, s). $^{13}$C NMR (75 MHz, CDCl$_3$): δ168.5, 152.0, 145.6, 130.0, 122.3, 112.2, 112.0, 51.6, 40.3.

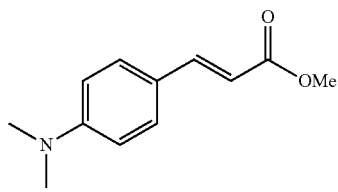

(E)-methyl 3-(4-(dimethylamino)phenyl)acrylate: 0.456 g, 86%; light yellow solid. $^1$H NMR (300 MHz, CDCl$_3$): δ7.62 (1H, d, J=15.9 Hz), 7.37 (2H, m), 6.91 (2H, m), 6.20 (1H, d, J=15.9 Hz), 3.74 (3H, s), 2.96 (6H, s). $^{13}$C NMR (75 MHz, CDCl$_3$): δ168.5, 152.0, 145.6, 130.0, 122.3, 112.2, 112.0, 51.6, 40.3.

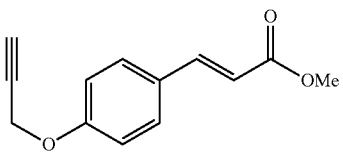 [SMILES: C#CCOc1ccc(/C=C/C(=O)OC)cc1]

(E)-methyl 3-(4-(prop-2-ynyloxy)phenyl)acrylate: 1.359 g, 87%, white solid. $^1$H NMR (400 MHz, CDCl$_3$): δ7.48 (1H, d, J=16 Hz), 7.32 (2H, d, J=8.8 Hz), 6.82 (2H, d, 8.8 Hz), 6.17 (1H, d, J=16 Hz), 4.56 (2H, d, J=2.4 Hz), 3.62 (3H, s), 2.57 (1H, t, J=2.4 Hz).

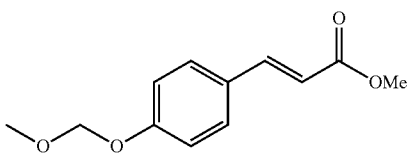 [SMILES: COCOc1ccc(/C=C/C(=O)OC)cc1]

(E)-methyl 3-(4-(methoxymethoxy)phenyl)acrylate: 1.362 g, 98%, white solid. $^1$H NMR (400 MHz, CDCl$_3$): δ7.64 (1H, d, J=16 Hz), 7.44 (2H, m), 7.02 (2H, m), 6.32 (1H, d, J=16 Hz), 5.19 (2H, s), 3.75 (3H, s), 3.47 (3H, s). $^{13}$C NMR (100 MHz, CDCl$_3$): δ167.8, 159.1, 144.6, 129.8, 128.3, 116.6, 116.0, 94.3, 56.3, 51.7.

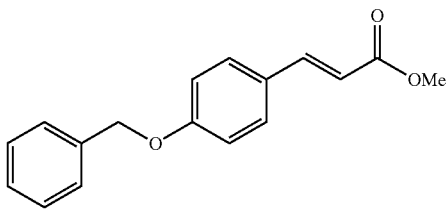 [SMILES: COC(=O)/C=C/c1ccc(OCc2ccccc2)cc1]

(E)-methyl 3-(4-(benzyloxy)phenyl)acrylate: 1.120 g, 83%, white solid. $^1$H NMR (300 MHz, CDCl$_3$): δ7.64 (1H, d, J=16 Hz), 7.41 (7H, m), 6.96 (2H, d, J=8.7 Hz), 6.30 (1H, d, J=16 Hz), 5.08 (2H, s), 3.78 (3H, s). $^{13}$C NMR (75 MHz, CDCl$_3$): δ144.4, 129.7, 128.6, 128.1, 127.4, 115.3, 115.1, 70.0, 51.5.

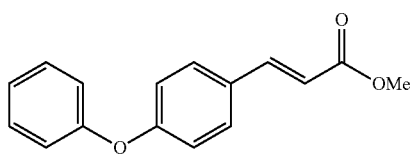 [SMILES: COC(=O)/C=C/c1ccc(Oc2ccccc2)cc1]

(E)-methyl 3-(4-phenoxyphenyl)acrylate: 0.395 g, 67%, white solid. $^1$H NMR (300 MHz, CDCl$_3$): δ7.65 (1H, d, J=15.9 Hz), 7.45 (2H, m), 7.32 (2H, m), 7.14 (1H, m), 7.00 (4H, m), 6.33 (1H, d, J=15.9 Hz), 3.77 (3H, s). $^{13}$C NMR (75 MHz, CDCl$_3$): δ167.7, 159.7, 156.3, 144.3, 130.2, 130.0, 129.4, 124.4, 119.9, 118.6, 116.7, 51.9.

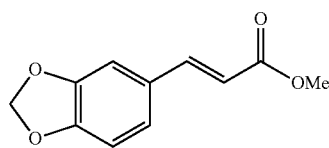 [SMILES: COC(=O)/C=C/c1ccc2c(c1)OCO2]

(E)-methyl 3-(benzo[d][1,3]dioxol-5-yl)acrylate: 1.097 g, 89%, white solid. $^1$H NMR (300 MHz, CDCl$_3$): δ7.28 (1H, d, J=15.9 Hz), 7.00 (2H, m), 6.79 (2H, m), 6.25 (1H, d, J=15.9 Hz), 3.78 (3H, s). $^{13}$C NMR (75 MHz, CDCl$_3$): δ167.6, 149.6, 148.3, 144.5, 128.8, 124.4, 115.7, 108.5, 106.5, 101.5, 51.6.

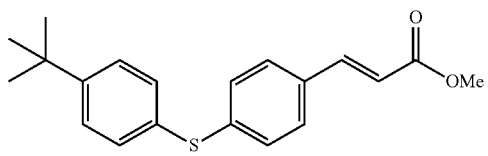 [SMILES: COC(=O)/C=C/c1ccc(Sc2ccc(C(C)(C)C)cc2)cc1]

(E)-methyl 3-(4-(4-tert-butylphenylthio)phenyl)acrylate: 0.298 g, 76%, white solid. $^1$H NMR (300 MHz, CDCl$_3$): δ7.63 (1H, d, J=15.9), 7.38 (6H, m), 7.19 (2H, m), 6.37 (1H, d, J=15.9 Hz), 3.79 (3H, s), 1.33 (9H, s). $^{13}$C NMR (75 MHz, CDCl$_3$): δ167.3, 151.6, 144.0, 141.1, 133.1, 131.8, 129.2, 128.4, 128.4, 126.5, 117.0, 51.6, 34.6, 31.1.

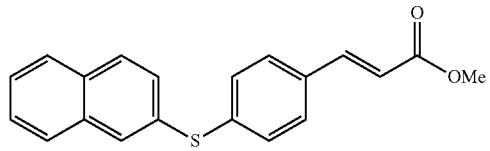 [SMILES: COC(=O)/C=C/c1ccc(Sc2ccc3ccccc3c2)cc1]

(E)-methyl 3-(4-(naphthalen-2-ylthio)phenyl)acrylate: 0.314 g, 100%, white solid. $^1$H NMR (300 MHz, CDCl$_3$): δ7.97 (1H, s), 7.78 (3H, m), 7.63 (1H, d, J=16.2 Hz), 7.48 (5H, m), 7.25 (2H, m), 6.39 (1H, d, J=16.2 Hz). $^{13}$C NMR (75 MHz, CDCl$_3$): δ144.3, 132.3, 130.0, 129.5, 128.9, 128.0, 127.9, 127.0, 117.7, 52.0.

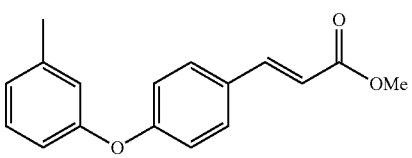 [SMILES: COC(=O)/C=C/c1ccc(Oc2cccc(C)c2)cc1]

(E)-methyl 3-(4-(m-tolyloxy)phenyl)acrylate (2.30): 67%, white solid. $^1$H NMR (300 MHz, CDCl$_3$): δ7.60 (1H, d, J=12 Hz), 7.39 (2H, m), 7.26 (1H, m), 7.16 (1H, m), 6.89 (2H, m), 6.78 (2H, m), 6.30 (1H, m), 3.72 (3H, s).

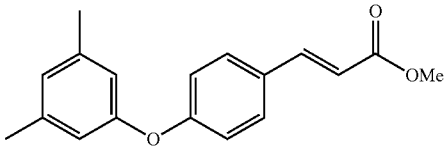 [SMILES: COC(=O)/C=C/c1ccc(Oc2cc(C)cc(C)c2)cc1]

(E)-methyl 3-(4-(3,5-dimethylphenoxyl)phenyl)acrylate: 0.131 g, 95%, clear gold oil. $^1$H NMR (300 MHz, CDCl$_3$): δ7.66 (1H, d, J=15.9 Hz), 7.46 (2H, m), 6.96 (2H, m), 6.80 (1H, s), 6.66 (2H, s), 6.34 (1H, d, J=15.9 Hz), 3.79 (3H, s), 2.29 (6H, s). $^{13}$C NMR (75 MHz, CDCl$_3$): δ167.8, 160.0, 156.2, 144.5, 140.1, 130.0, 129.1, 126.1, 118.5, 117.6, 116.5, 51.9, 21.5.

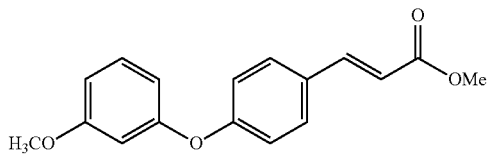 [SMILES: COC(=O)/C=C/c1ccc(Oc2cccc(OC)c2)cc1]

(E)-methyl 3-(4-(3-methoxyphenoxyl)phenyl)acrylate: 0.213 g, 82%, clear gold oil. $^1$H NMR (300 MHz, CDCl$_3$): δ7.65 (1H, d, J=15.9 Hz), 7.45 (2H, m), 7.23 (1H, m), 6.97 (2H, m), 6.69 (1H, m), 6.60 (2H, m), 6.34 (1H, d, J=15.9 Hz), 3.77 (3H, s), 3.76 (3H, s). $^{13}$C NMR (75 MHz, CDCl$_3$): δ167.8, 161.3, 159.5, 157.5, 144.3, 130.6, 130.0, 129.5, 118.8, 116.7, 111.9, 110.0, 105.9, 55.6, 51.9.

Example 5

Cyclopropanation of Acrylates Using Diazomethane

The following example is representative for the cyclopropanation of the acrylates using diazomethane.

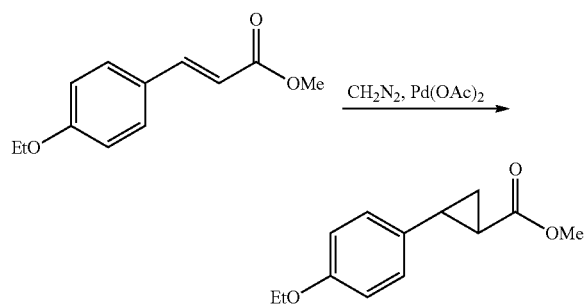

Methyl trans-2-(4-ethoxyphenyl)cyclopropanecarboxylate: The diazomethane generator was used. The (E)-methyl 3-(4-ethoxyphenyl)acrylate (1.8 mmol, 1 eq) and palladium (II) acetate catalyst (8.0 mg, 1.6 mol %) were dissolved in diethyl ether (26 mL) in the round bottom flask. 85% Potassium hydroxide pellets (2.81 g, 42 mmol, 23 eq) was dissolved in water (10 mL) and diethylene glycol monoethyl ether (15 mL) in the distillation chamber and brought to 60-70° C. using an oil bath. The cold finger was brought to −72° C. using isopropyl alcohol/dry ice and the round bottom brought to <−25° C. using ethylene glycol/dry ice. Diazald (3.90 g, 18 mmol, 10 eq) dissolved in diethyl ether (30 mL) was added dropwise from the addition funnel to the distillation chamber. The produced diazomethane was distilled into the round bottom collecting the clear golden yellow liquid. The round bottom capped loosely and stirred overnight (12-20 h) allowing to warm to rt. The reaction mixture was run over a plug of celite to remove the catalyst and the solvent removed by in vacuo. The reaction was monitored by $^1$H NMR and if alkene was still present (1H d~6.3 ppm, 1H d~7.6 ppm) additional equivalents of reagents were added to drive reaction to completion. No other purification was necessary to yield the white solid in 99% yield (0.286 g). $^1$H NMR (400 MHz, CDCl$_3$): δ6.99 (2H, m), 6.79 (2H, m), 3.97 (2H, q, J=7.6 Hz), 3.69 (3H, s), 2.48 (1H, ddd, J=4.2, 4.4, 11.3 Hz), 1.81 (2H, quintet, J=4.2), 1.54 (1H), 1.38 (3H, t, J=4.2), 1.25 (1H,). $^{13}$C NMR (100 MHz, CDCl$_3$): δ174.2, 157.9, 132.0, 127.5, 114.7, 63.6, 52.0, 26.0, 23.8, 16.9, 15.0.

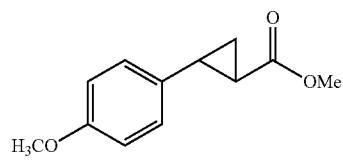 [SMILES: COC(=O)C1CC1c1ccc(OC)cc1]

Methyl trans-2-(4-methoxyphenyl)cyclopropanecarboxylate: 0.343 g, 91%, light yellow solid. $^1$H NMR (300 MHz, CDCl$_3$): δ7.00 (2H, m), 6.78 (2H, m), 3.72 (3H, s), 3.70 (3H, s), 2.49 (1H, ddd, J=4.5, 6.6, 8.4 Hz), 1.83 (2H, quintet, J=4.5 Hz), 1.56 (1H, m), 1.27 (1H, m). $^{13}$C NMR (75 MHz, CDCl$_3$): δ174.0, 158.7, 132.1, 127.6, 114.2, 55.3, 51.9, 25.8, 23.8, 16.8.

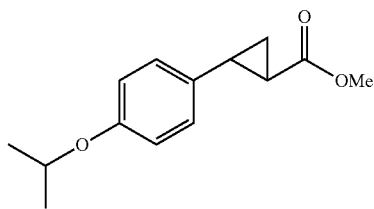 [SMILES: COC(=O)C1CC1c1ccc(OC(C)C)cc1]

Methyl trans-2-(4-isopropoxyphenyl)cyclopropanecarboxylate: 0.408 g, 100%, clear yellow oil. $^1$H NMR (300 MHz, CDCl$_3$): δ6.98 (2H, m), 6.78 (2H, m), 4.47 (1H, sep, J=6 Hz), 2.47 (1H, ddd, J=4.3, 4.5, 11.3), 1.82 (1H, q, J=4.2 Hz), 1.54 (1H, q, J=4.2 Hz). $^{13}$C NMR (75 MHz, CDCl$_3$): δ174.1, 156.9, 131.9, 127.6, 116.2, 70.1, 51.9, 26.0, 23.9, 22.2, 16.9.

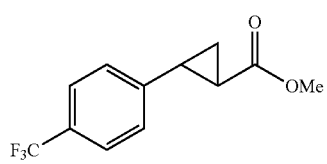

Methyl trans-2-(4-(trifluoromethyl)phenyl)cyclopropanecarboxylate: 0.423 g, 96%, pale yellow solid. $^1$H NMR (300 MHz, CDCl$_3$): δ7.51 (2H, d, J=8.1 Hz), 7.17 (2H, d, J=8.1 Hz), 3.71 (3H, s), 2.56 (1H, ddd, J=4.2, 6.3, 9.0 Hz), 1.94 (1H, ddd, J=4.2, 5.4, 8.7 Hz), 1.65 (1H, m), 1.33 (1H, ddd, J=4.8, 6.6, 8.4 Hz). $^{13}$C NMR (75 MHz, CDCl$_3$): δ173.6, 144.5, 125.6, 52.3, 26.0, 24.5, 17.5.

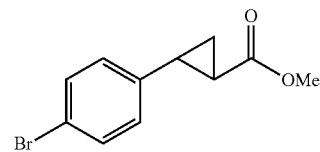 [SMILES: COC(=O)C1CC1c1ccc(Br)cc1]

Methyl trans-2-(4-bromophenyl)cyclopropanecarboxylate: 0.435 g, 94%, pale yellow oil. $^1$H NMR (300 MHz, CDCl$_3$): δ7.39 (2H, d, J=8.4 Hz), 6.97 (2H, d, J=8.4 Hz), 3.72 (3H, s), 2.48 (1H, ddd, J=4.5, 6.6, 8.4 Hz), 1.87 (1H, ddd, J=4.2, 5.1, 8.4 Hz), 1.60 (1H, ddd, J=4.5, 5.4, 9.3 Hz), 1.28 (1H, ddd, J=4.8, 6.6, 8.4 Hz). $^{13}$C NMR (75 MHz, CDCl$_3$): δ173.8, 139.3, 131.8, 128.2, 120.4, 52.2, 25.2, 24.1, 17.2.

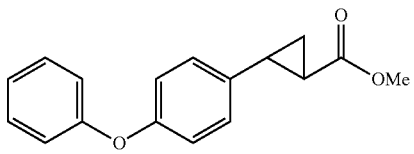 [SMILES: COC(=O)C1CC1c1ccc(Oc2ccccc2)cc1]

Methyl trans-2-(4-phenoxyphenyl)cyclopropanecarboxylate: 0.279 g, 100%, light gold oil. $^1$H NMR (300 MHz, CDCl$_3$): δ7.28 (2H, m), 7.02 (3H, m), 6.94 (4H, m), 3.69 (3H, s), 2.51 (1H, ddd), 1.86 (1H, ddd), 1.58 (1H, ddd), 1.27 (1H, ddd). $^{13}$C NMR (75 MHz, CDCl$_3$): δ174.1, 157.6, 156.1, 135.1, 130.0, 127.9, 123.4, 119.3, 118.9, 52.1, 30.0, 26.0, 24.1, 17.1.

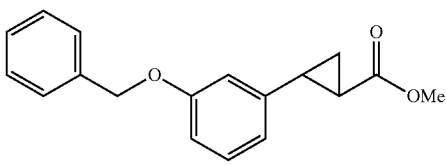 [SMILES: COC(=O)C1CC1c1cccc(OCc2ccccc2)c1]

Methyl trans-2-(3-(benzyloxy)phenyl)cyclopropanecarboxylate: 0.298 g, 100%, off-white solid. ¹H NMR (300 MHz, CDCl₃): δ7.37 (4H, m), 7.05 (2H, m), 6.92 (2H, m), 5.04 (2H, s), 3.73 (3H, s), 2.53 (1H, ddd), 1.86 (1H, ddd), 1.59 (1H, ddd), 1.29 (1H, ddd). ¹³C NMR (75 MHz, CDCl₃): δ147.2, 157.8, 137.3, 132.5, 128.9, 128.2, 127.7, 115.2, 70.3, 52.1, 26.0, 24.0, 17.0.

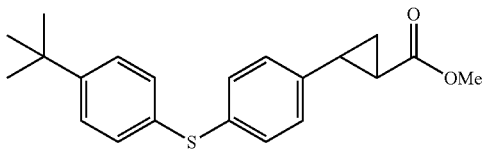

Methyl trans-2-(4-(4-tert-butylphenylthio)phenyl)cyclopropanecarboxylate: 0.246 g, 94%, gold oil. ¹H NMR (300 MHz, CDCl₃): δ7.25 (5H, m), 6.99 (2H, m), 3.69 (3H, s), 2.41 (1H, ddd), 1.87 (1H, ddd), 1.59 (1H, ddd), 1.29 (10H, m). ¹³C NMR (100 MHz, CDCl₃): δ173.9, 150.6, 139.1, 134.5, 132.4, 131.2, 127.2, 126.5, 52.2, 34.8, 31.5, 26.2, 24.3, 17.3.

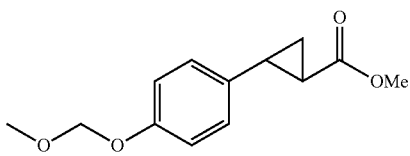 [SMILES: COCOc1ccc(C2CC2C(=O)OC)cc1]

Methyl trans-2-(4-(methoxymethoxy)phenyl)cyclopropanecarboxylate: 0.420 g, 100%, white solid. ¹H NMR (400 MHz, CDCl₃): δ7.00 (2H, m), 6.94 (2H, m), 5.11 (2H, s), 3.68 (3H, s), 3.43 (3H, s), 2.47 (1H), 1.82 (1H), 1.54 (1H), 1.25 (1H,). ¹³C NMR (100 MHz, CDCl₃): δ174.0, 156.1, 133.4, 127.5, 116.5, 94.6, 56.0, 51.9, 25.8, 23.8, 16.8.

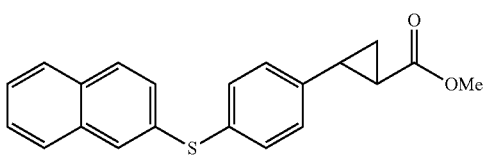

Methyl trans-2-(4-(naphthalen-2-ylthio)phenyl)cyclopropanecarboxylate: 0.254 g, 95%, gold oil. ¹H NMR (300 MHz, CDCl₃): δ7.70 (4H, m), 7.42 (5H, m), 6.99 (2H, m), 3.69 (3H, s), 2.49 (1H, ddd), 1.88 (1H, ddd), 1.60 (1H, ddd), 1.26 (1H, ddd). ¹³C NMR (75 MHz, CDCl₃): δ173.9, 139.7, 134.0, 133.7, 132.4, 131.9, 129.5, 129.1, 128.6, 128.0, 127.6, 127.4, 126.9, 126.4, 52.2, 26.2, 24.4, 17.4.

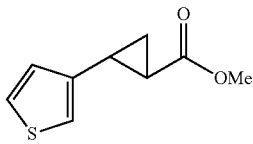 [SMILES: COC(=O)C1CC1c1ccsc1]

Methyl trans-2-(thiophen-3-yl)cyclopropanecarboxylate: 0.163 g, 99%, amber oil. ¹H NMR (300 MHz, CDCl₃): δ7.23 (1H, m), 6.95 (1H, m), 6.83 (1H, m), 3.71 (3H, s), 2.56 (1H, ddd, J=4.2, 6.6, 9.0 Hz), 1.87 (1H, ddd, J=4.2, 5.1, 8.4 Hz), 1.56 (1H, ddd, J=4.5, 5.1, 9.0 Hz), 1.26 (1H, ddd, J=4.5, 6.3, 8.4 Hz). ¹³C NMR (75 MHz, CDCl₃): δ173.9, 141.3, 126.2, 126.1, 120.0, 52.1, 23.6, 22.2, 17.1.

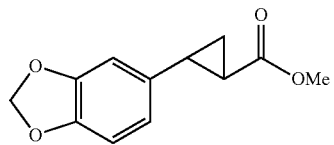

Methyl 2-(benzo[d][1,3]dioxol-5-yl)cyclopropanecarboxylate: 0.405 g, 100%, white solid. ¹H NMR (300 MHz, CDCl₃): δ6.68 (2H, m), 6.54 (2H, m), 5.88 (2H, s), 3.68 (3H, s), 2.44 (1H, ddd, J=4.2, 6.6, 8.4 Hz), 1.80 (1H, ddd, J=4.2, 5.0, 8.4 Hz), 1.52 (1H, ddd, J=5.0, 6.6, 7.8 Hz), 1.22 (1H, ddd, J=4.2, 6.6, 8.4 Hz). ¹³C NMR (75 MHz, CDCl₃): δ173.8, 147.8, 146.3, 133.8, 119.7, 108.1, 106.6, 101.0, 51.8, 26.8, 26.1, 23.7, 16.7.

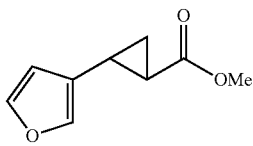 [SMILES: COC(=O)C1CC1c1ccoc1]

Methyl trans-2-(furan-3-yl)cyclopropanecarboxylate: 0.052 g, 97%, clear yellow oil. ¹H NMR (300 MHz, CDCl₃): δ7.32 (1H, m), 7.28 (1H, m), 6.15 (1H, m), 3.71 (3H, s), 2.33 (1H, ddd, J=4.2, 6.6, 9.0 Hz), 1.76 (1H, ddd, J=3.9, 5.1, 8.4 Hz), 1.50 (1H, m), 1.13 (1H, ddd, J=4.5, 6.6, 8.1 Hz). ¹³C NMR (75 MHz, CDCl₃): δ174.1, 143.4, 139.4, 124.9, 109.2, 52.1, 22.7, 17.5, 16.3.

Methyl trans-2-(4-(dimethylamino)phenyl)cyclopropanecarboxylate: 0.359 g, 81%, dark gold solid. ¹H NMR (300 MHz, CDCl₃): δ6.95 (2H, m), 6.64 (2H, m), 3.66 (3H, s), 2.80 (6H, s), 2.45 (1H, ddd, J=4.2, 4.5, 11.4 Hz), 1.79 (1H, ddd, J=4.2, 4.7, 8.4 Hz), 1.52 (1H, dd, J=4.8, 14.1 Hz), 1.24 (1H, ddd, J=4.5, 6.6, 8.3). ¹³C NMR (75 MHz, CDCl₃): δ174.4, 149.8, 127.9, 127.4, 113.1, 52.0, 41.0, 26.2, 23.8, 16.8.

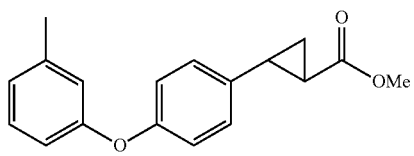 [SMILES: COC(=O)C1CC1c1ccc(Oc2cccc(C)c2)cc1]

Methyl trans-2-(3-(m-tolyloxy)phenyl)cyclopropanecarboxylate: 0.298 g, 100%, dark gold oil. $^1$H NMR (300 MHz, CDCl$_3$): δ6.99 (8H, m), 3.71 (3H, s), 2.48 (1H, ddd), 2.33 (3H, s), 1.88 (1H, ddd), 1.57 (1H, ddd), 1.29 (1H, ddd). $^{13}$C NMR (75 MHz, CDCl$_3$): δ130.2, 129.9, 129.7, 129.5, 125.3, 124.4, 121.1, 199.2, 117.1, 116.8, 116.1, 52.2, 26.3, 24.3, 24.2, 17.4, 17.2.

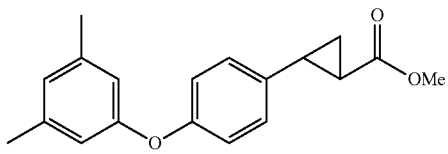 [SMILES: COC(=O)C1CC1c1ccc(Oc2cc(C)cc(C)c2)cc1]

Methyl trans-2-(4-(3,5-dimethylphenoxy)phenyl)cyclopropanecarboxylate: 0.125 g, 95%, gold oil. $^1$H NMR (300 MHz, CDCl$_3$): δ7.03 (2H, m), 6.91 (2H, m), 6.72 (1H, s), 6.59 (2H, s), 3.71 (3H, s), 2.51 (1H, ddd), 2.26 (6H, s), 1.85 (1H, ddd), 1.60 (1H, ddd), 1.29 (1H, ddd). $^{13}$C NMR (75 MHz, CDCl$_3$): δ174.1, 157.6, 156.3, 139.8, 134.8, 127.8, 125.2, 119.3, 116.6, 52.2, 26.0, 24.1, 21.6, 17.1.

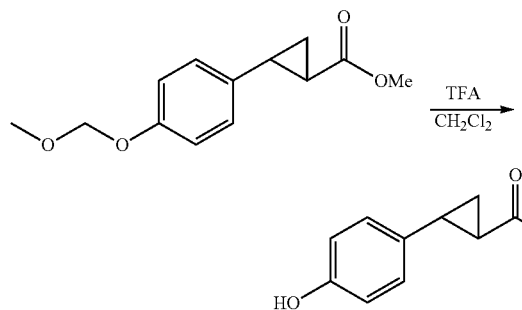

Methyl 2-(4-hydroxyphenyl)cyclopropanecarboxylate: A round bottom flask charged with the methyl ester (0.851 g, 3.6 mmol, 1 eq) in CH$_2$Cl$_2$ (20 mL) was brought to 0° C. Trifluoroacetic acid (2 mL, 26 mmol, 7.2 eq) was added slowly. The reaction was stirred for 24 h allowing to warm to rt. The crude reaction mixture was diluted with CH$_2$Cl$_2$ (50 mL) and then washed with saturated NaHCO$_3$ (50 mL) and saturated NaCl (50 mL), dried over anhydrous Na$_2$SO$_4$, and concentrated under reduced pressure. The desired methyl 2-(4-hydroxyphenyl)cyclopropanecarboxylate was isolated by flash chromatography over silica gel using 3:1 hexanes:ethyl acetate as a light gold oil in 62% yield (0.239 g). $^1$H NMR (300 MHz, CDCl$_3$): δ6.95 (2H, d, J=8.4 Hz), 6.75 (2H, d, J=8.4 Hz), 3.71 (3H, s), 2.48 (1H, m), 1.82 (1H, m), 1.55 (1H, m), 1.26 (1H, m). $^{13}$C NMR (75 MHz, CDCl$_3$): δ174.8, 154.9, 131.8, 127.8, 115.6, 52.2, 36.1, 25.6, 24.0, 17.0.

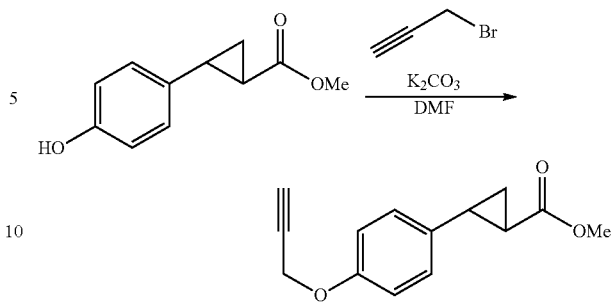

Methyl 2-(4-(prop-2-ynyloxy)phenyl)cyclopropanecarboxylate: An oven-dried round bottom flask charged with anhydrous dimethylformamide (2 mL), methyl 2-(4-hydroxyphenyl)cyclopropanecarboxylate (0.180 g, 0.9 mmol, 1 eq) and anhydrous potassium carbonate (0.418 g, 2.8 mmol, 3 eq) was stirred at 55° C. for 30 min. The reaction mixture was cooled to rt and propargyl bromide (98 μL, 1.1 mmol, 1.2 eq) was added. The reaction was stirred for 5 h at rt. The crude reaction mixture was poured on ice water (25 mL) and no precipitate formed. The organic products were extracted with ethyl acetate (3×30 mL), washed with saturated NH$_4$Cl (25 mL) and saturated NaCl (25 mL), dried over Na$_2$SO$_4$ and concentrated in vacuo affording the desired methyl 2-(4-(prop-2-ynyloxy)phenyl)cyclopropanecarboxylate as a dark yellow oil in 79% yield (0.170 g). $^1$H NMR (300 MHz, CDCl$_3$): δ7.04 (2H, d, J=8.7 Hz), 6.89 (2H, d, J=8.7 Hz), 4.66 (2H, d, J=2.4 Hz), 3.71 (3H, s), 2.50 (2H, m), 1.83 (1H, m), 1.56 (1H, m), 1.27 (1H, m). $^{13}$C NMR (75 MHz, CDCl$_3$): δ174.1, 156.5, 133.2, 127.6, 115.2, 78.8, 75.8, 56.1, 52.1, 25.9, 23.9, 16.9.

Example 6

Saponification of Methylcyclopropanecarboxylates

The following procedure is representative for saponification of the methyl cyclopropanecarboxylates to yield the corresponding carboxylic acids.

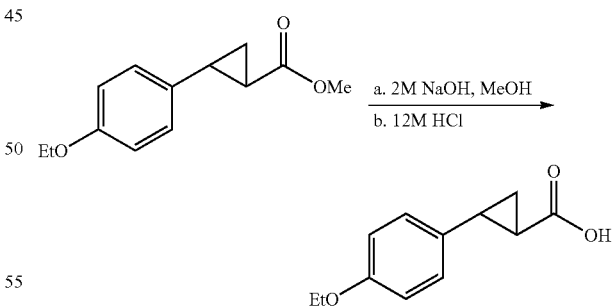

trans-2-(4-ethoxyphenyl)cyclopropanecarboxylic acid: To a solution of methyl trans-2-(4-ethoxyphenyl)cyclopropanecarboxylate (0.2862 g, 1.3 mmol, 1 eq) in methanol (3.4 mL) was added 2 M sodium hydroxide (3.4 mL) while stirring. The reaction was monitored by TLC and upon consumption of the ester, the mixture was poured onto ice (~60 mL) and 12 N HCl (1.4 mL) was added dropwise while stirring. The resulting precipitate was isolated by vacuum filtration. The filter cake was washed with portions of ice water until the filtrate was pH neutral and was dried in vacuo to give trans-2-(4-ethoxyphenyl)cyclopropanecarboxylic acid as an off-white solid in 78% yield (0.210 g). ¹H NMR (400 MHz, CDCl₃): δ7.02 (2H, m), 6.82 (2H, m), 4.00 (2H, q, J=6.8 Hz), 2.56 (1H, ddd, J=4.0, 6.5, 8.3 Hz), 1.82 (1H, ddd, J=4.0, 5.2, 8.3 Hz), 1.61 (1H, quintet, J=5.2 Hz), 1.40 (3H, t, J=6.8 Hz), 1.35 (ddd, J=4.0, 6.5, 8.3). ¹³C NMR (100 MHz, CDCl₃): δ180.1, 158.0, 131.5, 127.7, 114.8, 63.7, 26.9, 23.9, 17.4, 15.0.

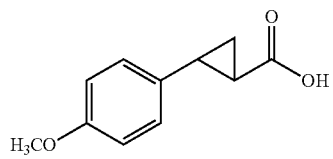 [SMILES: COc1ccc(C2CC2C(=O)O)cc1]

trans-2-(4-methoxyphenyl)cyclopropanecarboxylic acid: 0.237 g, 73%, white solid. ¹H NMR (300 MHz, CD₃OD): δ7.04 (2H, m), 6.82 (2H, m), 4.92 (1H, bs), 3.74 (3H, s), 2.41 (1H, ddd, J=4.2, 6.2, 9.5 Hz), 1.74 (1H, m), 1.47 (1H, quintet, J=4.8 Hz), 1.29 (ddd, J=4.8, 6.2, 8.1). ¹³C NMR (75 MHz, CD₃OD): δ176.1, 158.7, 132.1, 127.1, 113.8, 54.5, 25.5, 23.5, 15.9.

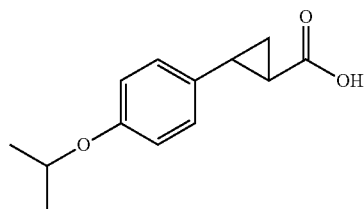 [SMILES: CC(C)Oc1ccc(C2CC2C(=O)O)cc1]

trans-2-(4-isopropoxyphenyl)cyclopropanecarboxylic acid: 0.384 g, 78%; white solid. ¹H NMR (400 MHz, CDCl₃): δ7.02 (2H, m), 6.81 (2H, m), 4.50 (1H, sep, J=6.0 Hz), 2.56 (1H, ddd, J=4.0, 6.8, 8.4 Hz), 1.82 (1H, ddd, J=4.0, 5.2, 8.4 Hz), 1.61 (1H, q, J=5.2 Hz), 1.35 (1H, ddd, J=4.0, 6.8, 8.4 Hz), 1.32 (6H, d, J=6.0 Hz). ¹³C NMR (100 MHz, CDCl₃): δ180.3, 157.0, 131.5, 127.7, 116.2, 70.2, 26.9, 24.0, 22.2, 17.4.

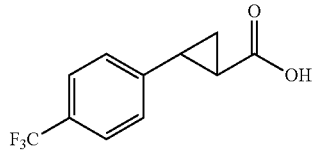

trans-2-(4-(trifluoromethyl)phenyl)cyclopropanecarboxylic acid: 0.395 g, 98%, pale yellow solid. ¹H NMR (300 MHz, CD₃OD): δ7.56 (2H, d J=8.1 Hz), 731 (2H, d, J=8.1 Hz), 2.54 (1H, ddd, J=4.2, 6.0, 9.0 Hz), 1.93 (1H, ddd, J=4.2, 5.4, 8.4 Hz), 1.59 (1H, m) 1.41 (1H, ddd, J=4.8, 6.3, 8.4 Hz). ¹³C NMR (75 MHz, CD₃OD): δ176.5, 146.5, 127.7, 126.4, 26.6, 25.5, 17.8.

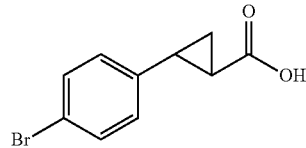 [SMILES: O=C(O)C1CC1c1ccc(Br)cc1]

trans-2-(4-bromophenyl)cyclopropanecarboxylic acid: 0.412 g, 100%, white solid. ¹H NMR (300 MHz, CD₃OD): δ7.40 (2H, d, J=8.1 Hz), 7.04 (2H, d, J=8.1 Hz), 2.43 (1H, ddd, J=4.2, 6.6, 9.0 Hz), 1.83 (1H, m), 1.52 (1H, m), 1.33 (1H, ddd, J=4.5, 6.3, 8.6 Hz). ¹³C NMR (75 MHz, CD₃OD): δ176.7, 141.0, 132.5, 129.0, 121.0, 26.5, 25.1, 17.4.

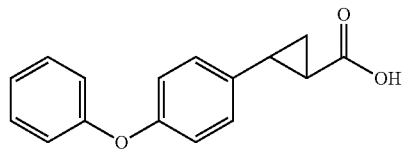 [SMILES: O=C(O)C1CC1c1ccc(Oc2ccccc2)cc1]

trans-2-(4-phenoxyphenyl)cyclopropanecarboxylic acid: 0.148 g, 58%, white solid. ¹H NMR (300 MHz, CD₃OD): δ7.27 (2H, m), 7.04 (3H, m), 6.89 (4H, m), 5.05 (1H, bs), 2.44 (1H, ddd), 1.78 (1H, ddd), 1.50 (1H, ddd), 1.28 (1H, ddd). ¹³C NMR (75 MHz, CD₃OD): δ75.9, 157.6, 156.1, 135.3, 129.7, 127.5, 123.1, 118.9, 118.5, 25.5, 23.8, 16.2.

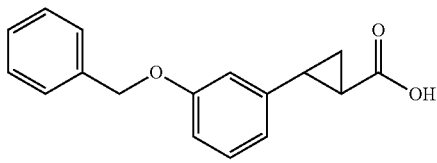 [SMILES: O=C(O)C1CC1c1cccc(OCc2ccccc2)c1]

trans-2-(3-(benzyloxy)phenyl)cyclopropanecarboxylic acid: 0.217 g, 76%, white solid. ¹H NMR (300 MHz, CDCl₃): δ7.30 (5H, m), 7.02 (2H, m), 6.90 (2H, m), 5.03 (2H, s), 2.40 (1H, ddd), 1.74 (1H, ddd), 1.47 (1H, ddd), 1.28 (1H, ddd).

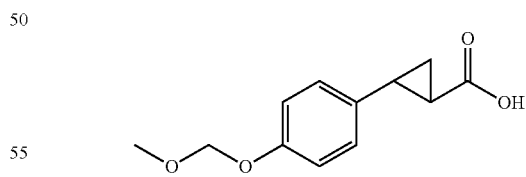

2-(4-(methoxymethoxy)phenyl)cyclopropanecarboxylic acid: 0.172 g, 67%, white solid. ¹H NMR (400 MHz, CD₃OD): δ7.01 (2H, d, J=8.6 Hz), 6.90 (2H, d, J=8.6 Hz), 5.09 (2H, s), 4.91 (1H, s), 3.39 (2H, s), 2.38 (1H, ddd, J=4.0, 6.4, 9.2 Hz), 1.72 (1H, ddd, J=4.0, 5.2, 8.1 Hz), 1.45 (1H, ddd, J=4.4, 5.2, 9.2 Hz), 1.26 (1H, ddd, J=4.4, 6.4, 8.1 Hz). ¹³C NMR (100 MHz, CD₃OD): δ176.0, 156.2, 133.2, 133.5, 127.1, 116.3, 94.4, 54.9, 25.5, 23.6, 16.0.

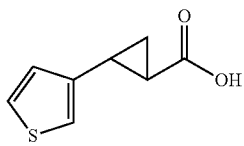 [SMILES: O=C(O)C1CC1c1ccsc1]

trans-2-(thiophen-3-yl)cyclopropanecarboxylic acid: 0.123 g, 90%, yellow solid. $^1$H NMR (300 MHz, CD$_3$OD): δ7.31 (1H, m), 7.08 (1H, m), 6.89 (1H, m), 2.54 (1H, ddd, J=4.2, 6.6, 9.0 Hz), 1.79 (1H, ddd, J=3.9, 5.1, 8.4 Hz), 1.48 (1H, m), 1.30 (1H, ddd, J=4.2, 6.6, 8.4 Hz). $^{13}$C NMR (75 MHz, CD$_3$OD): δ177.0, 142.6, 127.0, 126.9, 120.7, 24.5, 22.9, 17.3.

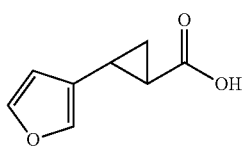 [SMILES: O=C(O)C1CC1c1ccoc1]

trans-2-(furan-3-yl)cyclopropanecarboxylic acid: 0.185 g, 65%, yellow solid. $^1$H NMR (300 MHz, CD$_3$OD): δ7.37 (2H, m), 6.22 (1H, m), 2.28 (1H, ddd, J=3.9, 6.3, 9.3 Hz), 1.70 (1H, ddd, J=4.2, 5.1, 8.4 Hz), 1.42 (1H, m), 1.16 (1H, ddd, J=4.2, 6.3, 8.4 Hz). $^{13}$C NMR (75 MHz, CD$_3$OD): δ177.1, 144.4, 140.4, 126.1, 109.8, 23.5, 18.2, 16.5.

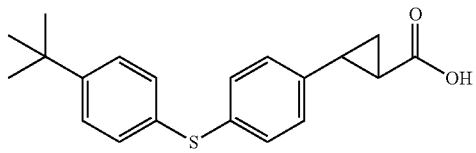 [SMILES: CC(C)(C)c1ccc(Sc2ccc(C3CC3C(=O)O)cc2)cc1]

trans-2-(4-(4-tert-butylphenylthio)phenyl)cyclopropanecarboxylic acid: 0.166 g, 73%, yellow oil. $^1$H NMR (300 MHz, CD$_3$OD): δ7.14 (8H, m), 4.99 (1H, bs), 2.41 (1H, ddd), 1.79 (1H, ddd), 1.49 (1H, ddd), 1.24 (10H, m).

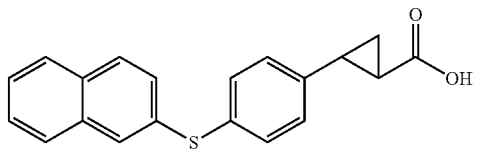 [SMILES: O=C(O)C1CC1c1ccc(Sc2ccc3ccccc3c2)cc1]

trans-2-(4-(naphthalen-2-ylthio)phenyl)cyclopropanecarboxylic acid: 0.203 g, 87%, yellow solid. $^1$H NMR (300 MHz, CD$_3$OD): δ7.72 (4H, m), 7.44 (2H, m), 7.29 (3H, m), 7.13 (2H, m), 2.46 (1H, ddd), 1.84 (1H, ddd), 1.55 (1H, ddd), 1.36 (1H, ddd).

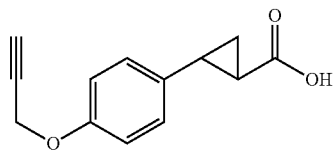 [SMILES: C#CCOc1ccc(C2CC2C(=O)O)cc1]

2-(4-(prop-2-ynyloxy)phenyl)cyclopropanecarboxylic acid: 0.179 g, 70%, white solid. $^1$H NMR (300 MHz, CD$_3$OD): δ7.07 (2H, d, J=8.6 Hz), 6.90 (2H, d, J=8.6 Hz), 4.86 (1H, s), 4.68 (2H, d, J=2.1 Hz)), 2.90 (1H, t, J=2.1 Hz), 2.42 (1H, m), 1.75 (1H, m), 1.48 (1H, m), 1.30 (1H, m).

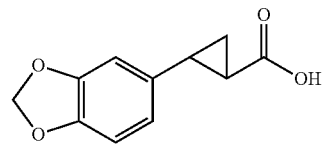 [SMILES: O=C(O)C1CC1c1ccc2c(c1)OCO2]

2-(benzo[d][1,3]dioxol-5-yl)cyclopropanecarboxylic acid: 0.281 g, 74%, white solid. $^1$H NMR (300 MHz, CD$_3$OD): δ6.62 (3H, m), 5.89 (2H, s), 4.95 (1H, bs), 2.39 (1H, ddd, J=3.9, 5.1, 9.0 Hz), 1.73 (1H, ddd, J=5.1, 6.5, 6.9), 1.45 (1H, ddd, J=3.9, 6.5, 9.0 Hz). $^{13}$C NMR (75 MHz, CD$_3$OD): δ175.7, 147.9, 146.3, 133.9, 119.3, 107.7, 106.1, 100.9, 25.7, 23.4, 15.8.

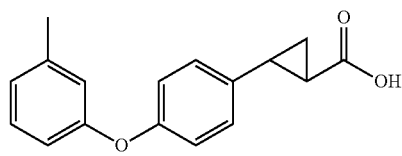 [SMILES: Cc1cccc(Oc2ccc(C3CC3C(=O)O)cc2)c1]

trans-2-(4-(m-tolyloxy)phenyl)cyclopropanecarboxylic acid: 0.199 g, 72%, dark brown oil. $^1$H NMR (300 MHz, CD$_3$OD): δ10.89 (1H, bs), 7.00 (8H, m), 2.54 (1H, ddd), 2.30 (3H, s), 1.84 (1H, ddd), 1.60 (1H, ddd), 1.34 (1H, ddd).

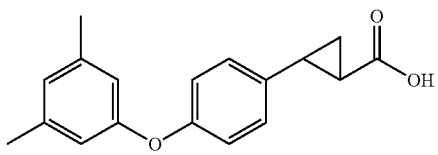 [SMILES: Cc1cc(C)cc(Oc2ccc(C3CC3C(=O)O)cc2)c1]

trans-2-(4-(3,5-dimethylphenoxy)phenyl)cyclopropanecarboxylic acid: 0.048 g, 41%, off-white solid. $^1$H NMR (300 MHz, CD$_3$OD): δ7.09 (2H, m), 6.85 (2H, m), 6.72 (1H, s), 6.54 (2H, s), 4.89 (1H, bs), 2.44 (1H, m), 2.23 (6H, s), 1.77 (1H, m), 1.49 (1H, m), 1.30 (1H, ddd).

Example 7

Curtius Rearrangements of Carboxylic Acids to Boc-Protected Amines

The following example is representative for Curtius rearrangement of carboxylic acids to general the corresponding t-butylcarbamate protected amines using diphenylphosphorylazide, triethylamine and t-butanol. In some cases, the carbamate could not be purified completely so impure material was taken on to the subsequent hydrolysis step.

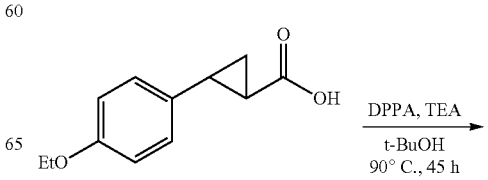

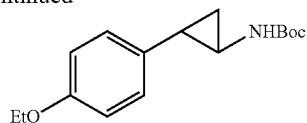

tert-Butyl trans-[2-(4-ethoxyphenyl)cyclopropyl]carbamate: Diphenylphosphorazidate (125 μL, 0.58 mmol, 1.2 eq) and anhydrous triethylamine (94 μL, 0.67 mmol, 1.4 eq) were added sequentially to a room temperature solution of trans-2-(4-ethoxyphenyl)cyclopropanecarboxylic acid (0.100 g, 0.48 mmol, 1 eq) in anhydrous tert-butanol (1 mL). The reaction was heated to 90° C. with an oil bath for 41 h, cooled to rt and concentrated to dryness under reduced pressure. The resulting residue was partitioned between ethyl acetate (10 mL) and 10% aqueous K₂CO₃ (10 mL). The organic products were extracted with ethyl acetate (2×10 mL), dried over Na₂SO₄, filtered, and concentrated in vacuo. The tert-butyl trans-[2-(4-ethoxyphenyl)cyclopropyl] carbamate was isolated by flash chromatography using 5:1 hexanes:ethyl acetate affording a yellow solid in 30% yield (0.040 g). ¹H NMR (400 MHz, CDCl₃): δ7.06 (2H, m), 6.79 (2H, m), 4.85 (1H, bs), 3.99 (2H, q, J=6.8 Hz) 2.64 (1H, bs), 1.98 (1H, m), 1.45 (9H, s), 1.38 (3H, d, J=6.8 Hz), 1.08 (2H, m). ¹³C NMR (100 MHz, CDCl₃): δ157.5, 132.8, 127.9, 114.6, 63.6, 28.6, 24.5, 16.0, 15.0.

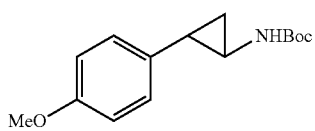 [SMILES: COc1ccc(C2CC2NC(=O)OC(C)(C)C)cc1]

tert-butyl trans-2-(4-methoxyphenyl)cyclopropylcarbamate: 0.186 g, 67%, white solid. ¹H NMR (300 MHz, CDCl₃): δ7.07 (2H, d, J=8.4 Hz), 6.80 (2H, d, J=8.4 Hz), 4.96 (1H, bs), 3.75 (3H, s), 2.64 (1H, m), 1.95 (1H, m), 1.45 (9H, s), 1.07 (2H, m). ¹³C NMR (75 MHz, CDCl₃): δ158.2, 133.2, 128.0, 120.4, 114.0, 79.7, 55.5, 32.4, 28.7, 24.5, 16.0.

tert-butyl trans-[2-(4-isopropoxyphenyl)cyclopropyl]carbamate: 0.077 g, 57%, white solid. ¹H NMR (400 MHz, CDCl₃): δ7.05 (2H, m), 6.79 (2H, m), 4.89 (1H, bs), 4.48 (1H, sep, J=6.0 Hz), 2.65 (1H, bs), 1.98 (1H, ddd, J=3.2, 6.4, 9.3 Hz), 1.45 (9H, s), 1.30 (6H, d, J=6.0 Hz), 1.08 (2H, m). ¹³C NMR (100 MHz, CDCl₃): δ156.4, 132.8, 127.9, 116.1, 70.2, 32.2, 28.6, 24.4, 22.3, 16.0.

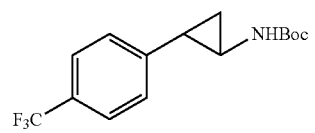 [SMILES: CC(C)(C)OC(=O)NC1CC1c1ccc(C(F)(F)F)cc1]

tert-butyl trans-[2-(4-(trifluoromethyl)phenyl)cyclopropyl]carbamate: 0.056 g, 42%, white solid. ¹H NMR (300 MHz, CDCl₃): δ7.50 (2H, d, J=8.1 Hz), 7.22 (2H, d, J=8.1 Hz), 4.85 (1H, bs), 2.74 (1H, m), 2.09 (1H, m), 1.45 (9H, s), 1.21 (2H, m). ¹³C NMR (75 MHz, CDCl₃): δ156.1, 145.4, 128.8, 126.8, 126.0, 79.3, 32.0, 28.6, 23.1, 16.1.

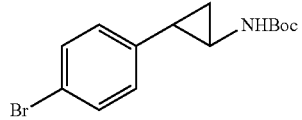 [SMILES: CC(C)(C)OC(=O)NC1CC1c1ccc(Br)cc1]

tert-butyl trans-[2-(4-bromophenyl)cyclpropyl]carbamate: 0.065 g, 50%, white solid. ¹H NMR (300 MHz, CDCl₃): δ7.36 (2H, d, J=8.1 Hz), 7.01 (2H, d, J=8.1 Hz), 4.84 (1H, bs), 2.66 (1H, m), 1.98 (1H, m), 1.45 (9H, s), 1.13 (2H, m). ¹³C NMR (75 MHz, CDCl₃): δ156.5, 140.0, 131.5, 128.6, 119.9, 80.0, 32.8, 28.6, 25.0, 16.4.

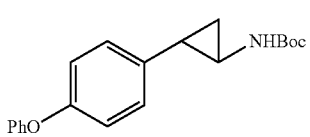

tert-butyl trans-[2-(4-phenoxyphenyl)cyclopropyl]carbamate: 0.035 g, 29%, yellow oil. ¹H NMR (300 MHz, CDCl₃): δ7.33 (2H, m), 7.10 (3H, m), 6.93 (4H, m), 4.85 (1H, bs), 2.69 (1H, m), 2.03 (1H, m), 1.46 (9H, s), 1.15 (2H, m). ¹³C NMR (75 MHz, CDCl₃): δ157.9, 156.6, 155.5, 136.0, 129.9, 128.1, 123.2, 119.4, 118.7, 79.9, 32.6, 28.6, 24.8, 16.3.

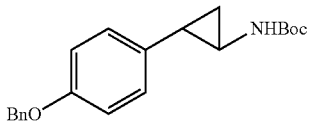 [SMILES: CC(C)(C)OC(=O)NC1CC1c1ccc(Oc2ccccc2)cc1]

tert-butyl trans-[2-(4-(benzyloxy)phenyl)cyclopropyl]carbamate: 0.039 g, 27%, yellow solid. ¹H NMR (300 MHz, CDCl₃): δ7.39 (5H, m), 7.07 (2H, d, J=8.7 Hz), 6.87 (2H, d, J=8.7 Hz), 5.03 (2H, s), 4.82 (1H, bs), 2.65 (1H, m), 1.99 (1H, ddd), 1.45 (9H, s), 1.09 (2H, m). ¹³C NMR (75 MHz, CDCl₃): δ157.5, 137.4, 133.3, 128.8, 128.1, 128.0, 127.7, 115.0, 70.3, 32.4, 29.9, 28.7, 24.6, 16.1.

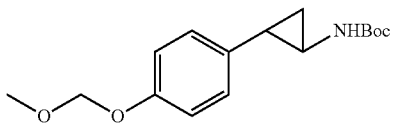 [SMILES: COCOc1ccc(C2CC2NC(=O)OC(C)(C)C)cc1]

tert-butyl 2-(4-(methoxymethoxy)phenyl)cyclopropylcarbamate: 0.144 g, 50% yield, white solid. ¹H NMR (300 MHz, CDCl₃): δ7.04 (2H, m), 6.92 (2H, m), 5.11 (2H, s), 5.05 (1H, bs), 3.43 (3H, s), 2.63 (1H, m), 1.97 (1H, m), 1.44 (9H, s), 1.05 (2H, m). ¹³C NMR (75 MHz, CDCl₃): δ156.6, 155.8, 134.4, 127.9, 116.5, 94.8, 79.7, 56.1, 32.5, 28.6, 24.5, 16.1.

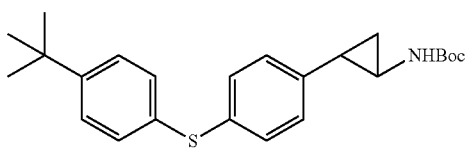 [SMILES: CC(C)(C)OC(=O)NC1CC1c1ccc(Sc2ccc(C(C)(C)C)cc2)cc1]

tert-butyl trans-[2-(4-(4-tert-butylphenylthio)phenyl]carbamate: 0.034 g, 29%, yellow oil. $^1$H NMR (300 MHz, CDCl$_3$): δ7.29 (6H, m), 7.06 (2H, d, J=8.4 Hz), 4.85 (1H, bs), 2.70 (1H, m), 2.01 (1H, m), 1.24 (18H, m), 0.95 (2H, m). $^{13}$C NMR (75 MHz, CDCl$_3$): δ150.3, 140.1, 133.4, 131.5, 130.7, 130.3, 127.5, 127.1, 126.4, 34.7, 32.9, 31.5, 29.9, 28.6, 25.1, 16.6.

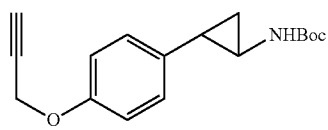 [SMILES: C#CCOc1ccc(C2CC2NC(=O)OC(C)(C)C)cc1]

tert-butyl trans-2-(4-(prop-2-ynyloxy)phenyl)cyclopropylcarbamate: 0.083 g, 37%, white solid. $^1$H NMR (300 MHz, CDCl$_3$): δ7.05 (2H, m), 6.77 (2H, m), 4.90 (1H, bs), 4.64 (2H, d, J=2.4 Hz), 2.64 (1H, m), 2.50 (1H, t, J=2.4 Hz), 2.00 (1H, m), 1.43 (9H, s), 1.09 (2H, m).

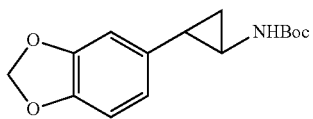 [SMILES: CC(C)(C)OC(=O)NC1CC1c1ccc2c(c1)OCO2]

tert-butyl trans-2-(benzo[d][1,3]dioxol-5-yl)cyclopropylcarbamate: 0.135 g, 43%, off-white solid. $^1$H NMR (300 MHz, CDCl$_3$): δ6.65 (3H, m), 5.87 (2H, s), 4.97 (1H, bs), 2.98 (1H, s), 2.60 (1H, m), 1.95 (1H, m), 1.44 (9H, s), 1.05 (2H, m). $^{13}$C NMR (75 MHz, CDCl$_3$): δ156.4, 147.6, 145.8, 134.6, 120.1, 108.0, 100.8, 79.5, 32.2, 28.4, 25.0, 15.8.

Example 8

Curtius Rearrangements to Form 2-(Trimethylsilyl)Ethyl Carbamates

The following example is representative for the Curtius rearrangement conditions to form the 2-(trimethylsilyl)ethyl carbamates.

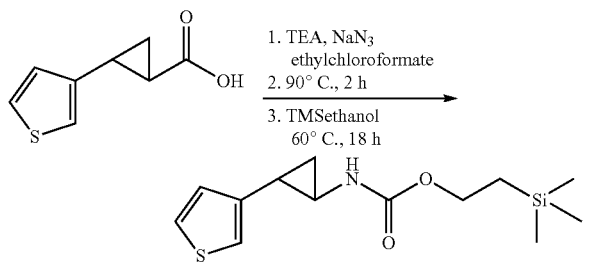

2-(trimethylsilyl)ethyl 2-(thien-3-yl)cyclopropylcarbamate: Ethylchloroformate (80.5 μL, 1.4 eq) and anhydrous triethylamine (103 μL, 1.2 eq) were added sequentially at −10 to −15° C. to a solution of the carboxylic acid (0.101 g, 1 eq) in anhydrous acetone (3.5 mL). The reaction mixture was stirred for 2 h. A solution of NaN$_3$ (0.065 g, 1.53 eq) in water (190 μL) was added, and the reaction stirred for 2 h. The reaction was quenched with ice cold water (3.5 mL). The acyl azide was extracted with ethyl ether (4×3 mL), dried over anhydrous MgSO$_4$, and concentrated under reduced pressure. The acyl azide was resuspended in toluene (3.6 mL) and heated to 90° C. while stirred for 2 h to promote the Curtius rearrangement. The reaction mixture was cooled to rt and concentrated under reduced pressure. TMS-ethanol (175 μL) was added and the reaction stirred at 60° C. for 18 h. The excess TMS-ethanol was removed under reduced pressure to afford the desired protected carbamate as a dark amber oil in 93% yield (0.158 g). $^1$H NMR (300 MHz, CDCl$_3$): δ7.21 (m, 1H), 6.90 (m, 2H), 5.10 (bs, 1H), 4.17 (t, J=8.2 Hz, 2H), 2.68 (bs, 1H), 2.05 (m, 1H), 1.11 (m, 2H), 0.98 (m, 2H), 0.02 (s, 9H). $^{13}$C NMR (300 MHz, CDCl$_3$): δ141.9, 127.1, 126.5, 125.8, 119.5, 63.4, 60.3, 32.4, 21.1, 18.0, 16.4, −1.2.

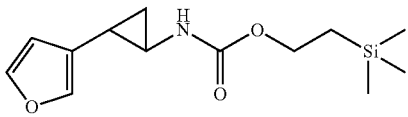 [SMILES: C[Si](C)(C)CCOC(=O)NC1CC1c1ccoc1]

2-(trimethylsilyl)ethyl 2-(furan-3-yl)cyclopropylcarbamate: 0.007 g, 26%, yellow solid. $^1$H NMR (300 MHz, CDCl$_3$): δ7.68 (m, 1H), 7.50 (m, 1H), 7.28 (m, 1H), 6.19 (bs, 1H), 4.20 (m, 2H), 2.58 (bs, 1H), 1.81 (m, 1H), 1.66 (m, 1H), 1.30 (m, 1H), 0.90 (m, 1H), 0.01 (s, 9H). $^{13}$C NMR (300 MHz, CDCl$_3$): δ157.4, 144.7, 127.0, 123.9, 123.3, 63.5, 33.5, 20.7, 18.0, 17.4, −1.3.

Example 9

Hydrolysis of Boc-Carbamates to Cyclopropylamines

The following example is representative for hydrolysis of the t-butyl carbamates to yield the cyclopropylamines.

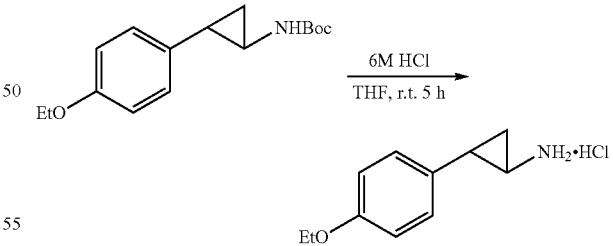

trans-2-(4-ethoxyphenyl)cyclopropylamine hydrochloride: The N-protected carbamate (0.0398 g, 0.14 mmol) was dissolved in THF (0.5 mL) and 6M HCl (0.3 mL). The reaction for stirred at rt for 25 h until TLC indicated complete consumption of starting material. The reaction mixture was concentrated to dryness and the resulting solid residue was dried in vacuo for 24 h over CaSO$_4$, resulting in a yellow solid in 85% yield (0.031 g). $^1$H NMR (300 MHz, CD$_3$OD): δ7.08 (2H, d, J=8.6 Hz), 6.84 (2H, d J=8.6 Hz), 4.86 (3H, bs), 3.99 (2H, q, J=6.9 Hz), 2.75 (1H, m), 2.24

(1H, m), 2.33 (3H, t, J=6.9 Hz), 1.25 (2H, m). $^{13}$C NMR (75 MHz, CD$_3$OD): δ158.2, 130.3, 127.5, 114.5, 63.3, 30.6, 20.7, 14.0, 12.2.

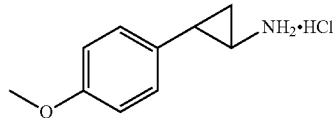

trans-2-(4-methoxyphenyl)cyclopropylamine hydrochloride: 0.131 g, 94%, yellow solid. $^1$H NMR (300 MHz, CD$_3$OD): δ7.06 (2H, d, J=8.4 Hz), 6.83 (2H, d, J=8.4 Hz), 3.75 (3H, s), 2.71 (1H, m), 2.35 (1H, m), 1.36 (1H, m), 1.22 (1H, m). $^{13}$C NMR (75 MHz, CD$_3$OD): δ160.0, 132.2, 128.5, 115.0, 55.7, 32.3, 22.5, 14.1.

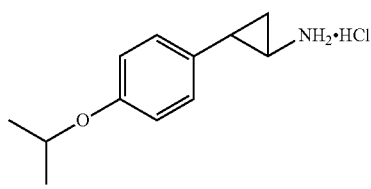

trans-2-(4-isopropoxyphenyl)cyclopropylamine hydrochloride: 0.840 g, 84%, yellow solid. $^1$H NMR (400 MHz, CD$_3$OD): δ7.04 (2H, d, J=8.6 Hz), 6.79 (2H, d, J=8.6 Hz), 4.50 (1H, quintet, J=6.0 Hz), 3.27 (1H, m), 2.71 (1H, m), 2.31 (1H, m), 1.34 (1H, m), 1.23 (6H, d, J=6.0 Hz) 1.19 (1H, m). $^{13}$C NMR (100 MHz, CD$_3$OD): δ157.0, 130.4, 127.5, 116.0, 69.8, 30.6, 21.1, 20.7, 12.2.

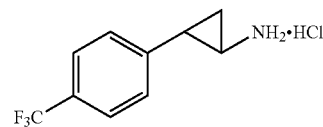

trans-2-(4-(trifluoromethyl)phenyl)cyclopropylamine hydrochloride: 0.044 g, 99%, white solid. $^1$H NMR (300 MHz, CD$_3$OD): δ7.60 (2H, d, J=8.7 Hz), 7.37 (2H, d, J=8.7 Hz), 2.95 (1H, m), 2.50 (1H, m), 1.53 (1H, m), 1.41 (1H, m). $^{13}$C NMR (75 MHz, CD$_3$OD): δ144.7, 128.1, 127.5, 126.5, 32.3, 22.3, 14.4.

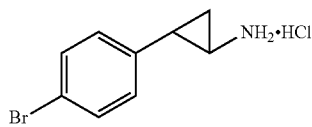

trans-2-(4-bromophenyl)cyclopropylamine hydrochloride: 0.052 g, 99%, white solid. $^1$H NMR (300 MHz, CD$_3$OD): δ7.44 (2H, d, J=8.1 Hz), 7.10 (2H, d, J=8.1 Hz), 2.84 (1H, m), 2.39 (1H, m), 1.46 (1H, m), 1.31 (1H, m). $^{13}$C NMR (75 MHz, CD$_3$OD): δ139.2, 132.7, 129.4, 121.3, 32.0, 22.0, 13.9.

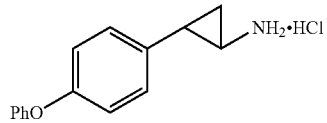

trans-2-(4-phenoxyphenyl)cyclopropylamine hydrochloride: 0.025 g, 88%, yellow solid. $^1$H NMR (300 MHz, CD$_3$OD): δ7.32 (2H, m), 7.17 (2H, m), 7.09 (1H, m), 6.93 (4H, m), 4.87 (3H, s), 2.82 (1H, m), 2.39 (1H, m), 1.42 (1H, m), 1.29 (1H, m). $^{13}$C NMR (75 MHz, CD$_3$OD): δ157.5, 156.5, 133.5, 129.7, 127.8, 123.3, 118.8, 118.6, 30.7, 20.8, 12.5.

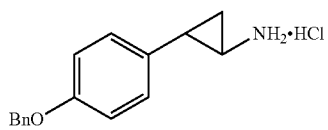

trans-2-(4-(benzyloxy)phenyl)cyclopropylamine hydrochloride: 0.028 g, 87%, yellow solid. $^1$H NMR (300 MHz, CD$_3$OD): δ7.36 (5H, m), 7.09 (2H, d, J=8.7 Hz), 6.93 (2H, d, J=8.7 Hz), 5.05 (2H, s), 4.87 (3H, s), 2.75 (1H, m), 2.32 (1H, m), 1.31 (2H, m). $^{13}$C NMR (75 MHz, CD$_3$OD): δ158.0, 137.5, 130.7, 128.3, 127.7, 127.5, 127.3, 115.0, 69.8, 30.6, 20.7, 12.2.

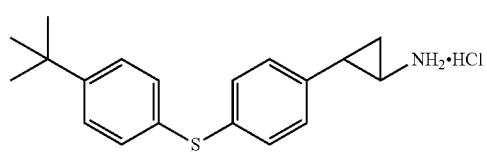

trans-2-(4-(4-tert-butylphenylthio)phenyl)cyclopropylamine hydrochloride: 0.019 g, 66%, yellow solid. $^1$H NMR (300 MHz, CD$_3$OD): δ7.21 (8H, m), 4.86 (3H, s), 2.83 (1H, ddd), 2.35 (1H, ddd), 1.31 (11H, m). $^{13}$C NMR (75 MHz, CD$_3$OD): δ137.4, 125.4, 134.2, 131.5, 130.4, 126.9, 126.6, 126.3, 34.3, 30.5, 29.6, 21.0, 12.7.

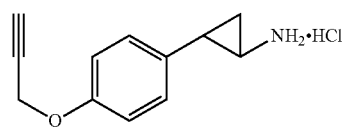

2-(4-(prop-2-ynyloxy)phenyl)cyclopropanamine hydrochloride salt: 0.055 g, 93%, light yellow solid. $^1$H NMR (300 MHz, CD$_3$OD): δ7.12 (2H, d, J=6.9 Hz), 4.87 (3H, s), 4.69 (2H, d, J=2.1 Hz), 2.92 (1H, t, J=2.1 Hz), 2.77 (1H, m), 2.36 (1H, m), 1.39 (1H, m), 1.26 (1H, m). $^{13}$C NMR (75 MHz, CD$_3$OD): δ156.7, 131.1, 127.2, 114.8, 78.4, 75.4, 55.3, 30.4, 20.5, 12.1.

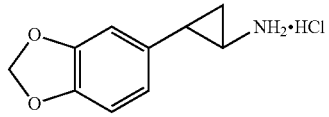

2-(benzo[d][1,3]dioxol-5-yl)cyclopropanamine hydrochloride salt: 0.089 g, 70%, yellow solid. $^1$H NMR (300 MHz, CD$_3$OD): δ6.70 (3H, m), 5.90 (2H, s), 4.86 (3H, s), 2.75 (1H, m), 2.32 (1H, m), 1.37 (1H, m), 1.24 (1H, m). $^{13}$C NMR (75 MHz, CD$_3$OD): δ148.0, 146.6, 132.1, 119.5, 107.8, 106.5, 101.0, 30.4, 21.0, 12.1.

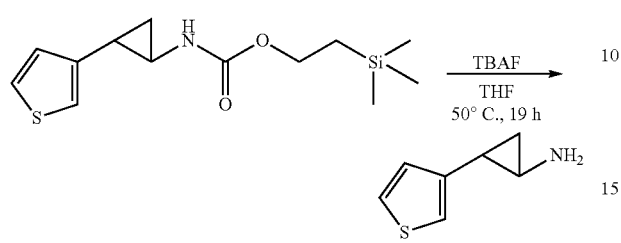

2-(thiophen-3-yl)cyclopropanamine: The 2-(trimethylsilyl)ethylcarbamate was resuspended in a solution of tetra-N-butylammonium fluoride (180 mg, 0.7 mmol, 1.25 eq) in THF (0.7 mL). The reaction was brought to 50° C. and stirred for 19 h. The reaction was quenched by dropwise addition of water (1.8 mL) and stirring for 30 min. The mixture was acidified with 1 M HCl (2 mL), washed with dichloromethane (4×2 mL), alkalinized with aqueous Na$_2$CO$_3$, extracted with EtOAC (3×3 mL), dried over K$_2$CO$_3$ and concentrated in vacuo. The desired free amine was isolated by flash chromatography using 100:1 chloroform:triethylamine as a yellow oil in 26% yield (0.021 g). $^1$H NMR (300 MHz, CDCl$_3$): δ 7.20 (m, 1H), 6.79 (m, 2H), 2.50 (m, 1H), 1.90 (m, 1H), 0.97 (m, 1H), 0.89 (m, 1H).

Example 10

Evaluation of Compounds in Mice

DAT-KO mice were generated as previously described (Giros, B.; Jaber, M.; Jones, S. R.; Wightman, R. M.; Caron, M. G., *Hyperlocomotion and indifference to cocaine and amphetamine in mice lacking the dopamine transporter.* Nature, 1996, 379, p. 606-612). Animal care was in accordance with the Guide for Care and Use of Laboratory Animals (National Institutes of Health publication #865-23, Bethesda, Md., United States) with an approved protocol from the Duke University Institutional Animal Care and Use Committee. DAT-KO mice, 3-5 month old, of both sexes were used.

Compounds 1-11 (Table 1) or saline (0.9% NaCl) were administered intraperitoneally (i.p) in a volume of 10 mL/kg. L-DOPA, carbidopa and benserazide were purchased from Sigma (St. Louis, Mo.).

TABLE 1

Phenylcyclopropylamines tested in DDD mice.

| Compound number | Structure |
|---|---|
| 1 | (phenyl-cyclopropyl-NH$_2$·HCl) |
| 2 | (naphthalen-1-yl-cyclopropyl-NH$_2$·HCl) |
| 3 | (4-Br-phenyl-cyclopropyl-NH$_2$·HCl) |
| 4 | (4-F$_3$C-phenyl-cyclopropyl-NH$_2$·HCl) |
| 5 | (4-H$_3$CO-phenyl-cyclopropyl-NH$_2$·HCl) |
| 6 | (Ph,Ph-cyclopropyl-NH$_2$·HCl) |
| 7 | (4-i-PrO-phenyl-cyclopropyl-NH$_2$·HCl) |
| 8 | (4-EtO-phenyl-cyclopropyl-NH$_2$·HCl) |
| 9 | (benzo[d][1,3]dioxol-5-yl-cyclopropyl-NH$_2$·HCl) |
| 10 | (4-propargyloxy-phenyl-cyclopropyl-NH$_2$·HCl) |
| 11 | (4-phenoxy-phenyl-cyclopropyl-NH$_2$·HCl) |

Locomotor activity of DAT-KO mice were measured in an Omnitech CCDigiscan (Accuscan Instruments, Columbus, Ohio) activity monitor under bright illumination (Gainetdinov et al. Science, 1999, 283, p. 397-401). All behavioral experiments were performed between 10:00 am and 5:00 pm. Activity was measured at 5 min intervals. To evaluate the effects of the treatments on motor behaviors, the mice were placed into activity monitor chambers (20×20 cm) for 30 min and then treated with α-MT (250 mg/kg, i.p.). The compound were injected 1 h after α-MT administration and various parameters of locomotor activity were monitored for up to 3 h. In cumulative dosing experiments, animals were treated with increasing doses of drugs at 1 h intervals.

Figure 2:
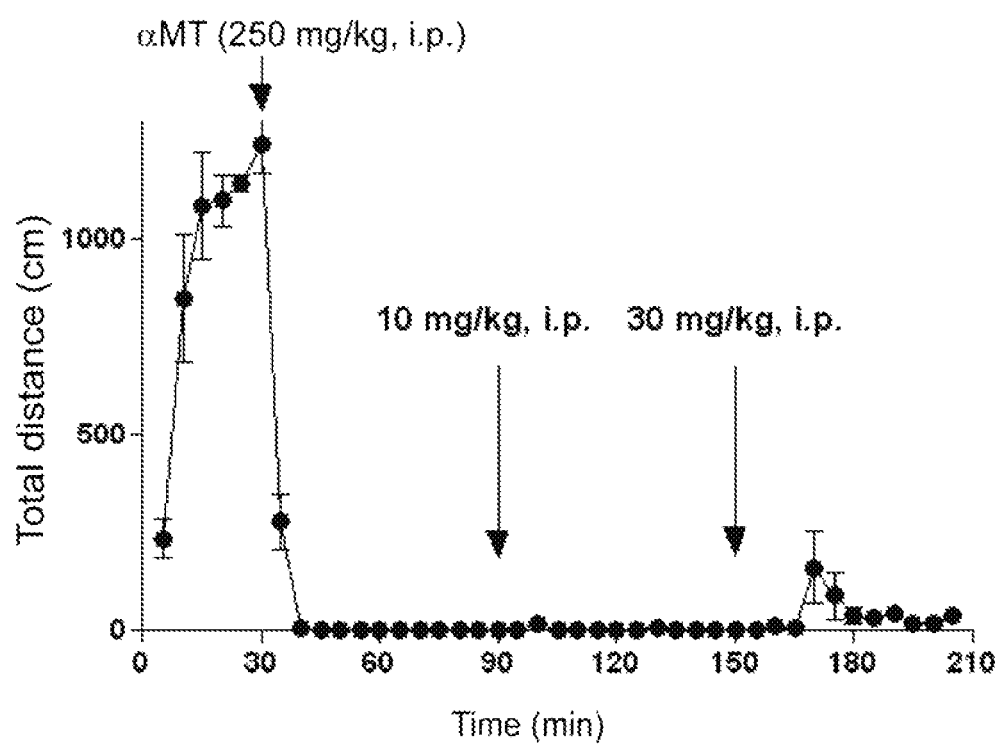
FIG. 2 illustrates locomotion observed after treatment with compound 9 in DDD mice (n=4).
Figure 3:
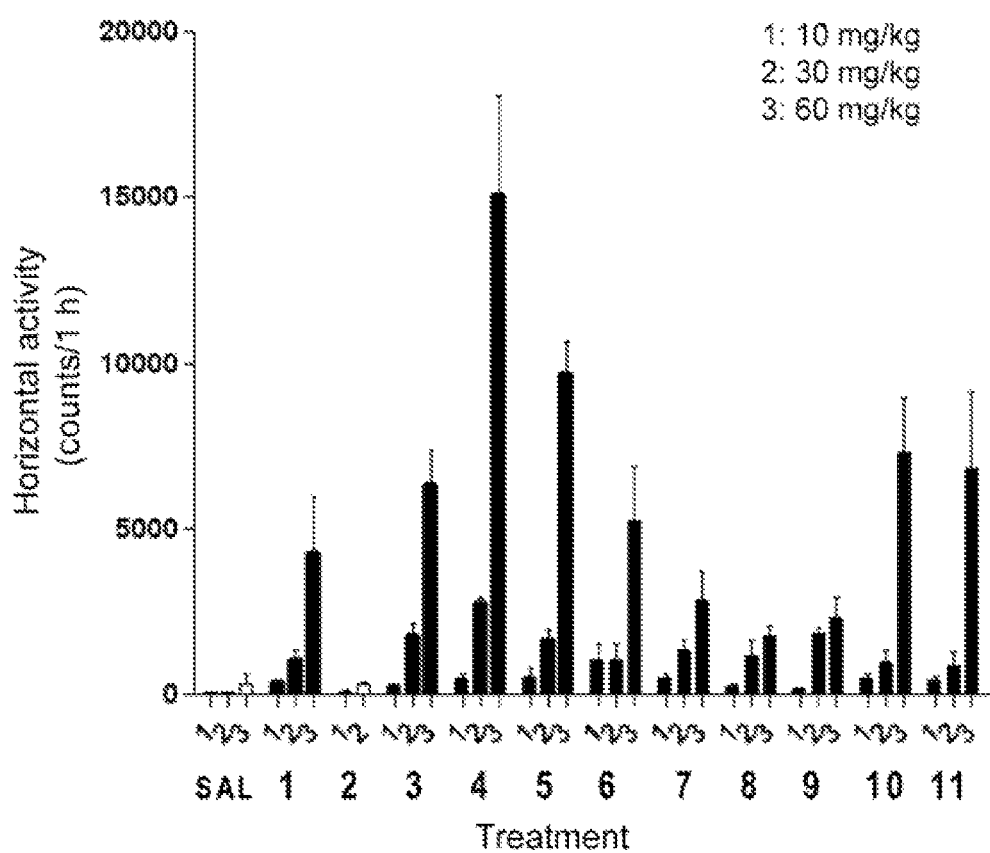
FIG. 3 provides a summary of initial screening of compounds 1-11 in DDD mice.

Results are illustrated in FIGS. 1-6. After administration of the compounds alone, the overall movement of the mice was observed and recorded. As seen in FIG. 1, the experiment with compound 2 was not completed because it was lethal after 30 mg/kg. Similarly, compound 6 caused seizures and paralysis in the mice after 30 mg/kg treatment. However, compounds 1, 3, 4, 5, and 7 resulted in active mice and reduced rigidity. The movement included shaking, tail straub, head bobbing and sniffing, similar to (+)-MDMA treatment. These compounds exhibited marked anti-akinesia activity. Compound 9, alone, was able to induce normal locomotion in DDD mice, making it the most promising derivative examined (FIG. 2). A summary of the overall movement is presented in FIG. 3.

Figure 4:
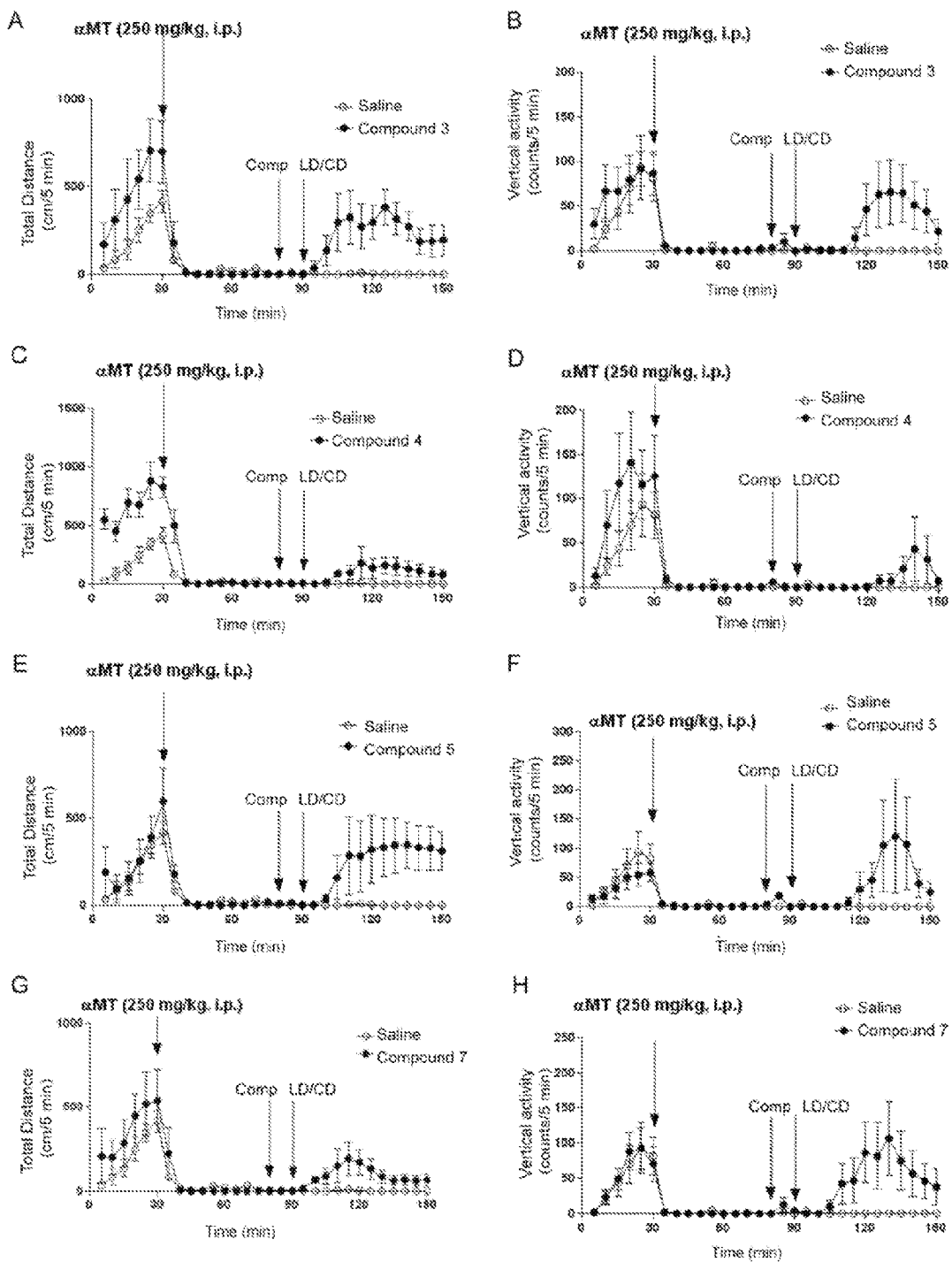
FIG. 4 illustrates results of treatment of DDD mice (n=6 for each) with phenylcyclopropylamines (5 mg/kg) and L-DOPA/Carpidopa (LD/CD, 10/10 mg/kg). A) Total distance after treatment with 3 and LD/CD. B) Vertical activity after treatment with compound 3 and LD/CD. C) Total distance after treatment with compound 4 and LD/CD. D) Vertical activity after treatment with compound 4 and LD/CD. E) Total distance after treatment with compound 5 and LD/CD. F) Vertical activity after treatment with compound 5 and LD/CD. G) Total distance after treatment with compound 7 and LD/CD. H) Vertical activity after treatment with compound 7 and LD/CD.
Figure 5:
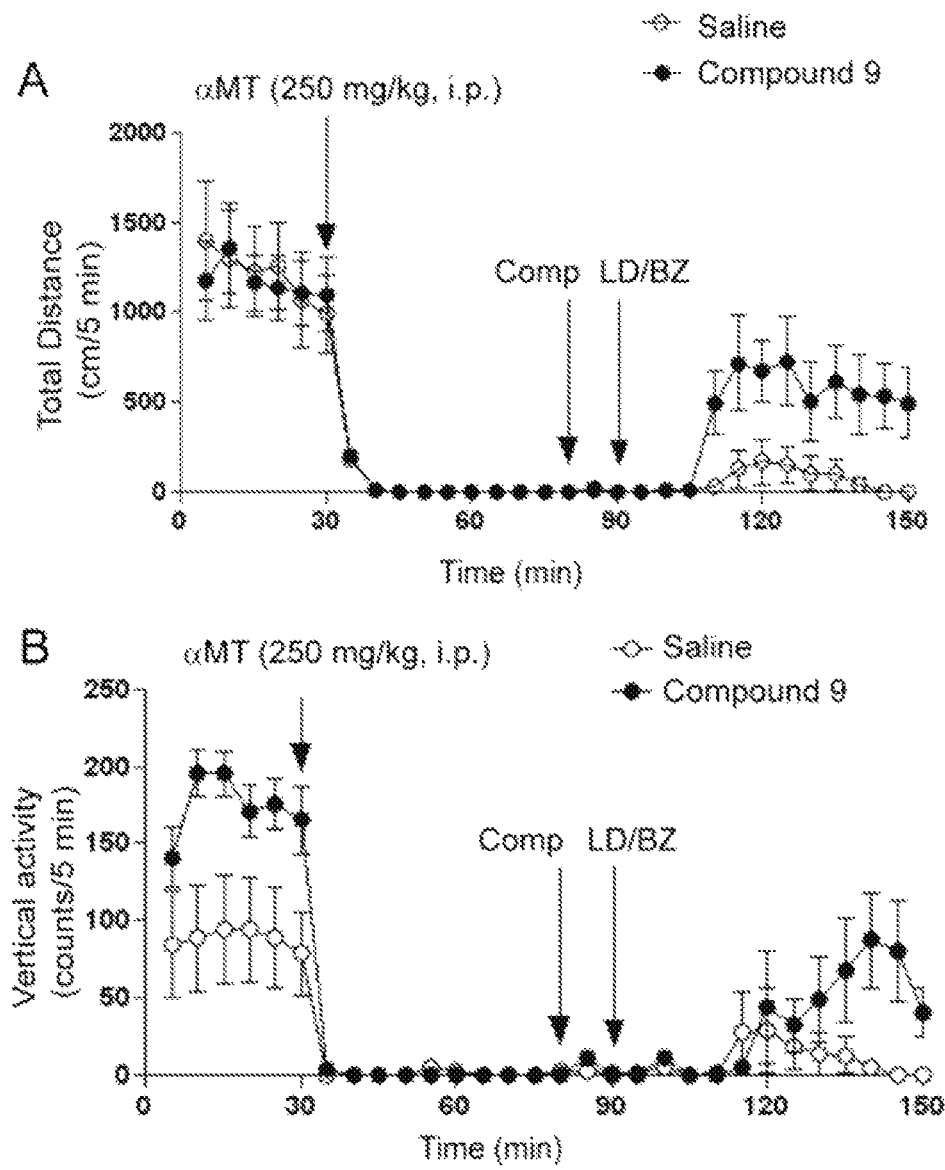
FIG. 5 illustrates results after treatment with compound 9 (5 mg/kg) with L-DOPA/Benserazide (LD/BZ, 10/10 mg/kg) in DDD mice (n=6). A) Total distance traveled. B) Vertical activity.
Figure 6:
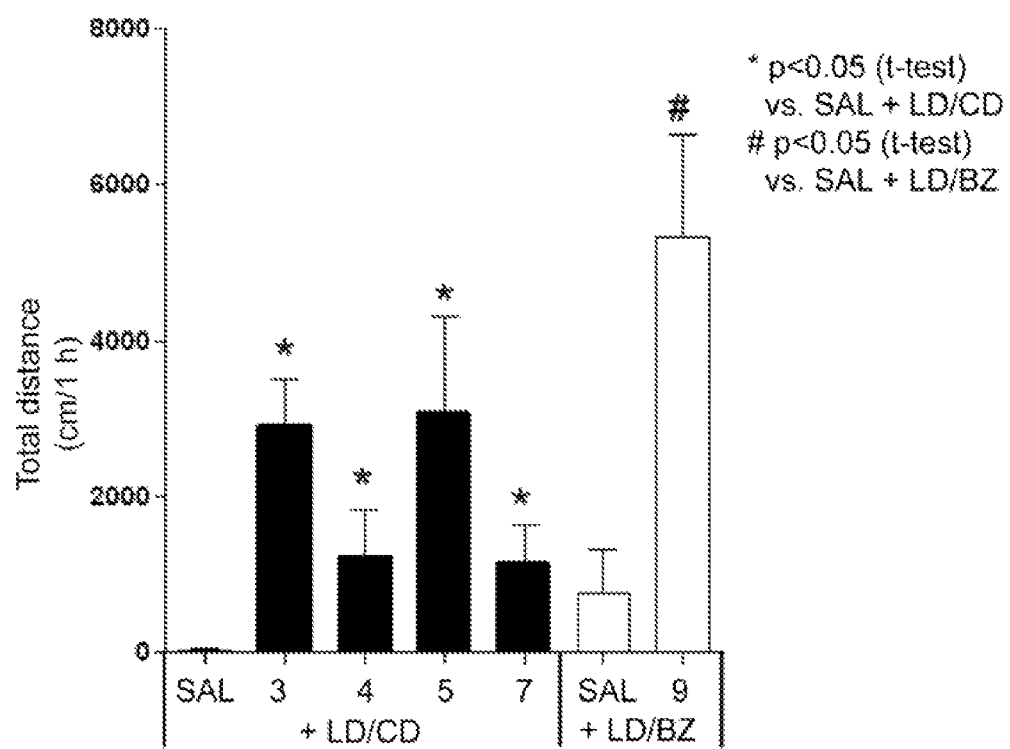
FIG. 6 illustrates results of enhancement of anti-Parkinsonian effects of phenylcyclopropylamines (5 mg/kg) and L-DOPA/Carbidopa (10/10 mg/kg) or L-DOPA/Benserazide (10/10 mg/kg) in DDD mice.

Several compounds (3, 4, 5, and 7) were also synergistic with L-DOPA/Carbiodopa treatment (FIG. 4). These compounds enhanced the low concentration of L-DOPA effects and induced locomotion and vertical activity. Compound 9 was tested collectively with L-DOPA/Benserazide and the mice had increased locomotion and vertical activity (FIG. 5). The results from treatment with the compounds and L-DOPA are summarized in FIG. 6. This indicates that the compounds may have utility in dose-sparing L-DOPA, in turn preventing dyskinesias.

Data are presented as mean±SEM and analyzed using a two-tailed Student's t-test and one way analysis of variance (ANOVA).

Example 11

Evaluation of Compounds in 6-OHDA-Treated Rats

Intracerebral Injection of 6-OHDA.

Per published procedures (e.g., Heidenreich et al. (2004) *Exp Neurol* 186:145-157; Heidenreich et al. (1995) *J Pharmacol Exp Ther* 273:516-525; Turner et al. (2008) *Brain Struct Funct* 213:197-213; and Turner et al. (2002) *J Pharmacol Exp Ther* 301:371-381) desipramine (25 mg/kg ip)-pretreated, anesthetized rats will be stereotaxically injected with 6-hydroxydopamine-HBr (6-OHDA; 7.5 μg (salt)/2 μl/side, Sigma) or its vehicle (0.2% ascorbic acid solution, pH=5.0) into the dorsolateral striatum (1.0 mm A to bregma, ±3.4 mm from midline, 4.7 mm V from skull). All behavioral testing will be initiated three weeks post surgery, and lesion extent will be behaviorally indicated with the forelimb adjusting step task and post mortem verified with tyrosine hydroxylase immunohistochemistry in the striatum.

The forelimb adjusting step task measures the ability of the rat to adjust to body position shifts imposed by the experimenter and is the rat homolog of the akinesia seen in PD (Olsson et al. (1995) *J Neurosci* 15:3863-3875). Rats, held by the experimenter with one unrestrained paw touching a platform, will be moved in an abduction and adduction direction (0.9 m/5 sec), and the adjusting steps made by the unrestrained paw counted. Three stepping trials will be taken per session, and the average score used. Assessments will be made prior to the 6-OHDA treatment surgery (i.e., baseline performance), and immediate before and after each treatment with the compounds.

Dyskinesia Assessments.

Animals will be placed in clear Perspex boxes (22 cm×34 cm×20 cm) and allowed 30 min to habituate to the environment. L-DOPA methyl ester (6 mg/kg, i.p.) will be administered at 20 min time intervals. Each rat will be observed for 1 min every 20 min for 3 hr. A scoring system for the three subtypes of abnormal involuntary movements (AIMs) will be assessed.

Evaluation of Anti-Parkinsonian Efficacy Vs. Dyskinesia Side Effects.

We will assess the anti-Parkinsonian efficacy of test compounds. Rats treated with 6-OHDA will be assigned a treatment groups: (i) compound of interest, (ii) LD/CD (positive control; tested at an efficacious dose) and (iii) vehicle (negative control) (n=12/group; no shams are needed for this evaluation). Initial doses for test compounds will be approximately 1/10th of the efficacious dose observed in DDD mice (approximately 6 mg/kg) and the PD-like rats will be rated for improvement in forelimb stepping, and the appearance of dyskinesias. In DDD mice the maximal effects with test compounds were observed approximately 30 min after dosing; thus for the rats motor deficits and dyskinesias will be monitored 30, 60, 90 and 120 min after dosing to capture the maximal efficacy window. In rats, the rating interval will be based on the Cmax determined from the literature for tranylcypromine (Sherry et al. (2000) *J Affective Disorders* 61: 23-29). Tests will be conducted once a day for five consecutive days (Monday-Friday) at a given dosage level. Doses will then be increased by approximately ½ log order each week for up to 5 weeks. The highest dose of test compound that reduces forelimb stepping that had acceptable adverse effects will serve as a benchmark for subsequent studies.

Example 12

Evaluation of Compounds for Drug Abuse Liability

Motor deficit improvements resulting from treatments with test compounds will be determined in the same rats used to evaluate abuse liability. Three doses (with maximal dose selected from 2.4.2 outcomes) and saline each will be tested in both PD-like and sham control rats for both studies. One study will evaluate the abuse liability of compounds using condition place preference and motor sensitization. Another study will use intracranial self-stimulation. Extensive research over several decades has established the validity of each of these assays for predicting an important component of abuse liability. Together, they provide a framework for informed regulatory and medical decision making regarding the abuse potential of compounds.

Condition Place Preference (CPP) refers to the capacity of a conditioned stimulus (e.g., environmental context) to acquire the salience of an unconditioned stimulus (e.g., a drug reward). Thus, CPP manifests reward-mediated associative learning as demonstrated by the rats' tendency to spend more time in the environmental context that was previously paired with the drug reward. CPP expression is thought to reflect aspects of drug seeking Rats with 6-OHDA-induced lesions within the striatum can acquire and express methamphetamine-induced CPP (Napier et al. *Movement Disorders* 25(7):S283, 2010.); this demonstrates the utility of this task to ascertain abuse liability in PD-like rats. The D3 receptor preferring agonist, pramipexole, in doses that reversed 6-OHDA-induced motor deficits (i.e., the severe reductions in the forelimb adjusting task) were sufficient to induce place preference and motor sensitization in these same rats (Id.). The same protocol can be used with arylcyclopropylamine compounds.

Per prior publications (e.g., Dallimore et a. (2006) *Behav Neurosci* 120:1103-1114; Shen et al. (2006) *J Neurosci* 26:11041-11051; Herrold et al. (2009) *Drug Alcohol Depend* 99:231-239; Herrold et al. (2011) *Synapse* 65:1333-4343; Voigt et al. (2011) *Behav Neurosci* 125:261-267; Voigt et al. (2011) *Behav Brain Res* 216:419-423; Voigt et al. (2011) *Behav Brain Res* 225:91-96), CPP testing will be done in a rodent activity apparatus (AccuScan Instruments, Inc., Columbus, Ohio) (63 cm×30 cm×30 cm) that consists of two larger end chambers (25 cm) separated by a small center chamber (13 cm). Each chamber has distinct but neutral visual and tactile cues. Motor activity and time spent in each chamber will be recorded via 24 photobeams. The CPP task consists of three phases: pretest, conditioning, and post-test. For the pretest, rats will be placed into the center chamber, and allowed access to the entire apparatus for 3 min. Time spent in each context will be recorded. The activity box configurations do not impose an inherit bias for the group, but individual rats show slight side deviations; thus, these data will be used to assign treatment groups such that the pretest time spent in each chamber is approximately equal across the all conditioning treatment groups. Conditioning procedures, initiated two days later, will consist of treating the rats and immediately placing them in the assigned side for 45 min. Treatment pairings will be alternated with saline; e.g., drug conditioning may occur on days 1, 3, 5 and 7, and with the saline vehicle on days 2, 4, 6 and 8 rats. Saline-conditioned rats will receive saline on all 8 days. One day after the last conditioning session, rats will be given a post-test using the same procedures described for the pretest. Time spent in the drug-paired chamber will be compared for the pretest and post-test to determine whether shifts in chamber preference occurred as a consequence of conditioning. Place preference is revealed by an increase in time spent in the drug-paired chamber during the post-test compared to the same chamber during the pretest.

Motor Sensitization.

Repeated intermittent administration of abused psychoactive drugs (e.g., amphetamine, MDMA, etc.) in rodents causes a progressive increase in drug-induced motor activity that is higher in magnitude compared to that induced by a single injection. Motor sensitization reflects neuronal adaptations that recapitulate aspects of those seen in addicted humans. Thus, the emergence of motor sensitization in rodents treated with a novel compound indicates potential abuse liability of the compound. The condition place preference protocol allows simultaneous assessment of motor sensitization (Shen et al. (2006) *Neurosci* 26:11041-11051). To do so, motor activity will be monitored throughout the 45 min conditioning periods, and sensitization is verified by a within subjects comparisons of the first and last treatment.

Intracranial Self Stimulation.

ICSS experiments will be conducted in operant chambers (Med-Associates, St. Albans, Vt.) outfitted with a chamber light, and two retractable levers each under a stimulus light. Electrical brain stimulation (EBS) will be delivered by a programmable stimulator via bipolar leads connected to commutators mounted above the chamber. As has been published (Rokosik et al. (2011) *J Neurosci Methods* 198: 260-269) and shown to be effective in rat models of PD (Rokosik et al. (2010) *Movement Disorder* s25(7):5285), the rats will be trained to press a lever using a standardized EBS (200 μs biphasic square wave pulses, applied at 100 Hz for 500 ms). The initial current intensity (100 μA) will be adjusted for each rat until stable ICSS is reached in a fixed ratio-1 (FR-1) reinforcement schedule for a 30 min session. Rats then will be pseudo-randomly presented with one of 16 different current frequencies tested in 10 Hz increments, ranging from 10-160 Hz. For each frequency, rats will have access to the lever for 2 min and lever presses will be recorded. The lever then will be retracted for 10 sec. In each session, a lever pressing rate vs. ICSS current frequency (i.e., Rate-Frequency Function) will be collected and the maximal (Emax) number of lever presses determined using a non-linear regression. Once stable, an average of three curves will used to determine ICSS frequencies that produced 90%, 60% and 10% of Emax (termed 'effective current' (ECur); $ECur_{90}$, $ECur_{60}$ and $ECur_{10}$, respectively. A reduction in the $ECur_{60}$ or an increase in the $ECur_{10}$ during treatment with a compound would indicate an enhancement in ICSS-mediated reward and thus indicate an abuse liability.

Alternative approaches can be implemented should a compound or a dose show abuse potential in one of the planned tasks but not the others, with the idea that converging evidence from a large set of more diverse tasks would be useful in this instance. Moreover, this aids in establishing the breadth of conditions under which a compound may be abused. For example, rats can be trained to self-administer cocaine (or another drug of abuse) by lever pressing in an operant box similar to that used for ICSS. Once rats exhibit stable drug intake, the training drug can be substituted by an experimental compound. If the experimental drug is self-administered this indicates potential drug abuse liability. In such a case, drug-naïve rats can then be tested to assess whether the compound is self-administered in subjects that have no prior drug experience, providing stronger evidence for the abuse liability of the novel compound. Drug discrimination protocols could be implemented. In this task, rats are trained to discriminate between a drug of abuse (e.g., cocaine and MDMA) and vehicle in a two-lever food-reinforced procedure. Following training, rats are tested with an experimental drug to determine whether generalization ('substitution') to the drug of abuse cue occurs, indicative of potential abuse liability and a shared pharmacological target. Alternatively, rats could be trained to discriminate between an experimental compound and vehicle, and substitution tests with various drugs of abuse (MDMA, cocaine, amphetamine, etc.) could be run for generalization.

Example 13

Assessment of L-DOPA Dose-Sparing and Anti-Dyskinesia Activities

Studies will also ascertain the capacity of the compounds to enhance the motoric efficacy of LDOPA in lesioned rats. 6-OHDA-treated rats will be assigned to one of four treatment groups (n=12/group). Rats in Group B and C will receive either a dose of the test compounds that is less than the minimal efficacious dose observed in earlier studies.

In addition to the test compounds, rats will be given an ascending dose regimen of LD/CD. A comparator group will be treated with test compound vehicle plus the same ascending dose regimen of LD/CD. The dose of test compound administered to Group B (*) will be either (a) a dose at less than the minimum efficacious dose (based on stepping deficit assessments), or (b) the maximally tolerated dose (based on dyskinesia assessments) observed in Study 1. LD/CD doses of less than 8/2 mg/kg are not expected to exhibit anti-Parkinsonian or pro-dyskinetic effects in rats. Thus, these experiments are designed to determine if the test compounds enhance the effects of sub-therapeutic doses of LD/CD. L-DOPA sparing activity will be identified by enhanced efficacy on improving stepping deficits with sub-therapeutic doses of L-DOPA. The dosing of test compound and LD/CD will be done so that Cmax and maximal therapeutic effect for both LD and the test compound occurs within the same time frame. Cmax will be determined experimentally, but it is of note that previous PK data are available for tranylcypromine (Sherry, 2000), and thus may serve as a starting point for these studies.

The results of these studies should demonstrate whether or not the administration of test compounds at low efficacious or sub-efficacious doses will produce enhance efficacy of LD/CD. Importantly, these studies will also test whether or not the combination of either of the two test compounds with LD/CD alters the pro-dyskinetic and/or anti-Parkinsonian effects of LD. Dyskinesias are consistently observed in animals given LD/CD at 8/2 mg/kg so it should be possible to compare the effects of LD/CD alone at this dose with the combined effects of LD/CD and the test compound.

Example 14

Evaluation of Compounds in MPTP-Lesioned Monkey Models of PD

Squirrel monkeys made Parkinsonian by injections of MPTP will be used. Animals will be drawn from a cohort of MPTP-lesioned animals that have shown stable Parkinsonism scores over a period of more than 8 months. Animals will be rated according to standardized rating scales by two independent raters, blinded to the treatment.

The efficacy of test compounds will be assessed. Four groups of animals (n=5-6/group) matched for gender and Parkinsonian disability will be dosed with either vehicle (Group A), increasing doses of test compounds (Groups B & C) or an efficacious dose of LD/CD (8/2 mg/kg, Group D). Baseline ratings for animals are obtained on Mondays and animals are dosed on Tuesday-Friday and rated daily. Initial doses for test compounds will be approximately 1/10th of the efficacious dose observed in DDD mice (approximately 6 mg/kg) and animals will be rated for improvement in PD scores, the appearance of dyskinesias and closely monitored for other adverse effects. In DDD mice the maximal effects with test compounds were observed approximately 30 minutes after dosing. In monkeys, the rating interval will be based on the Cmax determined from the literature for tranylcypromine. Animals will be rated for Parkinsonism and dyskinesias at additional intervals around the Cmax (e.g. 30, 60, 90 and 120 minutes after dosing) in order to capture the maximal efficacy window. Animals will be dosed for up to four consecutive days (Tuesday-Friday) at a given dosage level. Doses will then be increased by approximately ½ log order each week for up to 5 weeks. The lowest dose of test compound that produces reductions in Parkinsonism will be used as a benchmark for the next phase of the studies (see below). If no dose is found that reduces Parkinsonism than the highest dose that had acceptable adverse effects will be used. Select plasma levels will be drawn and concentrations of test compounds assayed to establish basic PK parameters (Cmax and exposure) for these compounds to guide efficacy evaluations.

Animals from the above studies will be "washed out" for two weeks with continued daily ratings for Parkinsonism and dyskinesia. Based on our previous experience, LD/CD treated animals will return to their pre-treatment baseline values during this period. After washout, animals in Group B and C will receive either a dose that is less than the minimal efficacious dose observed in the above experiment or if no anti-Parkinsonian efficacy is observed, the maximally tolerated dose. In addition to the test compound, animals will be given an ascending dose regimen of LD/CD. A comparator group (Group D) will be treated with vehicle plus the same ascending dose regimen of LD/CD.

The dose of test compound administered to Group B (*) will be either (a) a dose at less than the minimum efficacious dose or (b) the maximally tolerated dose observed in the Phase 1 study. In our experience LD/CD doses of less than 8/2 mg/kg do not result in anti-Parkinsonian or pro-dyskinetic effects in monkeys. Thus, these experiments are designed to determine if the test compounds enhance the effects of sub-therapeutic doses of LD/CD. L-DOPA sparing activity will be identified by enhanced efficacy with sub-therapeutic doses of L-DOPA. The dosing of test compound and LD/CD will be done so that Cmax and maximal therapeutic effect for both LD and the test compound occurs within the same time frame. Relative dosing intervals will be based on PK values obtained in these animals. The results of these studies should demonstrate whether or not the administration of test compounds at low efficacious or subefficacious doses will produce enhance efficacy of LD/CD. Importantly, these studies will also test whether or not the combination of either of the 2 test compounds with LD/CD enhances the pro-dyskinetic as well as anti-Parkinsonian effects of LD. Finally, the results of these studies could point to an anti-dyskinetic effect for the compound. We consistently observe dyskinesias in animals given LD/CD at 8/2 mg/kg so it will be possible to compare the effects of LD/CD alone at this dose with the combined effects of LD/CD and the test compound.

Although the disclosure above has been described in terms of various aspects and specific embodiments, it is not so limited. A variety of suitable alterations and modifications for operation under specific conditions will be apparent to those skilled in the art. It is therefore intended that the following claims be interpreted as covering all such alterations and modifications as fall within the spirit and scope of the invention.

All patents, publications and references cited herein are hereby fully incorporated by reference. In case of conflict between the present disclosure and incorporated patents, publications and references, the present disclosure should control.

The invention claimed is:

1. A method of treating Parkinson's disease in a subject in need of treatment, comprising administering to the subject an effective amount of a compound of formula (I):

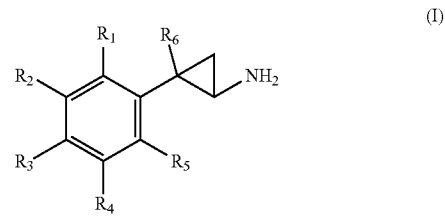

wherein $R_2$, $R_4$ and $R_5$ are hydrogen;
wherein $R_3$ is selected from $C_{5-20}$ aryloxy, $C_{1-7}$ alkoxy, $C_{1-7}$ haloalkyl, and halo; and
$R_6$ is hydrogen and; or an isomer, or pharmaceutically acceptable salt thereof.

2. The method of claim 1, wherein the compound of formula (I) is selected from the group consisting of:
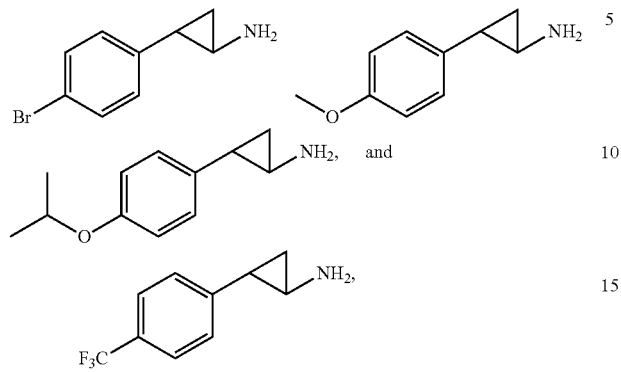
or a pharmaceutically acceptable salt thereof.
* * * * *